US012620473B2

(12) United States Patent
Booth et al.

(10) Patent No.: US 12,620,473 B2
(45) Date of Patent: *May 5, 2026

(54) METHOD AND DOSING CONTROLLER FOR ADMINISTERING A CORRECTION DOSE OF INSULIN

(71) Applicant: Aseko, Inc., Greenville, SC (US)

(72) Inventors: Robert C. Booth, Greer, SC (US);
Harry Hebblewhite, Atlanta, GA (US)

(73) Assignee: Glytec, LLC, Greenville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/324,140

(22) Filed: May 25, 2023

(65) Prior Publication Data

US 2023/0298732 A1     Sep. 21, 2023

Related U.S. Application Data

(63) Continuation of application No. 17/305,658, filed on Jul. 12, 2021, now Pat. No. 11,694,785, which is a continuation of application No. 15/496,419, filed on Apr. 25, 2017, now Pat. No. 11,081,226, which is a continuation-in-part of application No. 14/922,763, filed on Oct. 26, 2015, now Pat. No. 9,892,234.

(60) Provisional application No. 62/069,195, filed on Oct. 27, 2014.

(51) Int. Cl.
| | |
|---|---|
| *G16H 20/60* | (2018.01) |
| *A61B 5/00* | (2006.01) |
| *A61B 5/145* | (2006.01) |
| *A61M 5/172* | (2006.01) |
| *G16H 10/40* | (2018.01) |
| *G16H 10/60* | (2018.01) |
| *G16H 20/17* | (2018.01) |
| *G16H 40/63* | (2018.01) |
| *G16H 40/67* | (2018.01) |

(52) U.S. Cl.
CPC ........... *G16H 20/60* (2018.01); *A61B 5/0022* (2013.01); *A61B 5/14532* (2013.01); *A61B 5/4839* (2013.01); *A61B 5/7475* (2013.01); *A61M 5/1723* (2013.01); *G16H 10/40* (2018.01); *G16H 10/60* (2018.01); *G16H 20/17* (2018.01); *G16H 40/63* (2018.01); *G16H 40/67* (2018.01); *A61B 5/14503* (2013.01); *A61B 5/7239* (2013.01); *A61B 5/7405* (2013.01); *A61M 2205/3303* (2013.01)

(58) Field of Classification Search
None
See application file for complete search history.

(56) References Cited

U.S. PATENT DOCUMENTS

| | | | |
|---|---|---|---|
| 561,422 | A | 6/1896 | Minnis |
| 4,055,175 | A | 10/1977 | Clemens et al. |
| 4,151,845 | A | 5/1979 | Clemens |
| 4,206,755 | A | 6/1980 | Klein |
| 4,403,984 | A | 9/1983 | Ash et al. |
| 4,464,170 | A | 8/1984 | Clemens et al. |
| 4,731,726 | A | 3/1988 | Allen, III |
| 4,850,959 | A | 7/1989 | Findl |
| 4,911,168 | A | 3/1990 | Davis |
| 4,947,845 | A | 8/1990 | Davis |
| 4,981,779 | A | 1/1991 | Wagner |
| 5,091,190 | A | 2/1992 | Kuczynski et al. |
| 5,216,597 | A | 6/1993 | Beckers |
| 5,251,126 | A | 10/1993 | Kahn et al. |
| 5,822,715 | A | 10/1998 | Worthington et al. |
| 5,956,501 | A | 9/1999 | Brown |
| 5,998,363 | A | 12/1999 | Forse et al. |
| 6,024,699 | A | 2/2000 | Surwit et al. |
| 6,186,145 | B1 | 2/2001 | Brown |
| 6,233,539 | B1 | 5/2001 | Brown |
| 6,379,301 | B1 | 4/2002 | Worthington et al. |
| 6,428,825 | B2 | 8/2002 | Sharma et al. |
| 6,472,366 | B2 | 10/2002 | Kishino et al. |
| 6,540,672 | B1 | 4/2003 | Simonsen et al. |
| 6,544,212 | B2 | 4/2003 | Galley et al. |
| 6,560,471 | B1 | 5/2003 | Heller et al. |
| 6,572,542 | B1 | 6/2003 | Houben et al. |
| 6,575,905 | B2 | 6/2003 | Knobbe et al. |
| 6,605,039 | B2 | 8/2003 | Houben et al. |
| 6,615,081 | B1 | 9/2003 | Boveja |
| 6,669,663 | B1 | 12/2003 | Thompson |

(Continued)

FOREIGN PATENT DOCUMENTS

| | | |
|---|---|---|
| AU | 199460325 A | 8/1994 |
| AU | 2009283013 A1 | 2/2010 |

(Continued)

OTHER PUBLICATIONS

Baghdadi et al. (29th Annual International Conference of the IEEE Engineering in Medicine and Biology Society, 2007, pp. 3216-3219) (Year: 2007).*

(Continued)

*Primary Examiner* — Pablo S Whaley
(74) *Attorney, Agent, or Firm* — Honigman LLP; Brett A. Krueger; Grant Griffith

(57) ABSTRACT

A method of administering insulin includes receiving scheduled glucose time intervals and obtaining glucose data of a patient that includes glucose measurements, glucose times, and insulin dosages previously administered by the patient. The method also includes applying a set of filters to identify which of the glucose measurements associated with at least one of the scheduled time intervals are usable and which of the glucose measurements associated with the at least one scheduled time interval are unusable. The method also includes aggregating the glucose measurements associated with the at least one scheduled time interval identified as usable to determine a representative aggregate glucose measurement and determining a next recommended insulin dosage for the patient based on the representative aggregate glucose measurement and the insulin dosages previously administered by the patient.

20 Claims, 46 Drawing Sheets

(56) References Cited

U.S. PATENT DOCUMENTS

| | | | |
|---|---|---|---|
| 6,740,072 B2 | 5/2004 | Starkweather et al. |
| 6,808,703 B2 | 10/2004 | Park et al. |
| 6,890,568 B2 | 5/2005 | Pierce et al. |
| 6,927,246 B2 | 8/2005 | Noronha et al. |
| 7,025,425 B2 | 4/2006 | Kovatchev et al. |
| 7,039,560 B2 | 5/2006 | Kawatahara et al. |
| 7,060,059 B2 | 6/2006 | Keith et al. |
| 7,108,680 B2 | 9/2006 | Rohr et al. |
| 7,137,951 B2 | 11/2006 | Pilarski |
| 7,167,818 B2 | 1/2007 | Brown |
| 7,204,823 B2 | 4/2007 | Estes et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,404,796 B2 | 7/2008 | Ginsberg |
| 7,498,318 B1 | 3/2009 | Stahl et al. |
| 7,509,156 B2 | 3/2009 | Flanders |
| 7,553,281 B2 | 6/2009 | Hellwig et al. |
| 7,651,845 B2 | 1/2010 | Doyle, III et al. |
| 7,704,226 B2 | 4/2010 | Mueller, Jr. et al. |
| 7,734,323 B2 | 6/2010 | Blomquist et al. |
| 7,806,886 B2 | 10/2010 | Kanderian, Jr. et al. |
| 7,824,333 B2 | 11/2010 | Otto et al. |
| 7,837,622 B2 | 11/2010 | Itoh et al. |
| 7,853,455 B2 | 12/2010 | Brown |
| 7,877,271 B2 | 1/2011 | Brown |
| 7,901,625 B2 | 3/2011 | Brown |
| 7,904,310 B2 | 3/2011 | Brown |
| 7,912,688 B2 | 3/2011 | Brown |
| 7,920,998 B2 | 4/2011 | Brown |
| 7,949,507 B2 | 5/2011 | Brown |
| 7,985,848 B2 | 7/2011 | Woo et al. |
| 8,088,731 B2 | 1/2012 | Knudsen et al. |
| 8,117,020 B2 | 2/2012 | Abensour et al. |
| 8,185,412 B1 | 5/2012 | Harpale |
| 8,198,320 B2 | 6/2012 | Liang et al. |
| 8,204,729 B2 | 6/2012 | Sher |
| 8,206,340 B2 | 6/2012 | Arefieg |
| 8,257,300 B2 | 9/2012 | Budiman et al. |
| 8,257,735 B2 | 9/2012 | Lau et al. |
| 8,318,221 B2 | 11/2012 | Miller et al. |
| 8,329,232 B2 | 12/2012 | Cheng et al. |
| 8,333,752 B2 | 12/2012 | Veit et al. |
| 8,370,077 B2 | 2/2013 | Bashan et al. |
| 8,398,616 B2 | 3/2013 | Budiman |
| 8,420,125 B2 | 4/2013 | Webster et al. |
| 8,420,621 B2 | 4/2013 | Lai et al. |
| 8,457,901 B2 | 6/2013 | Beshan et al. |
| 8,527,208 B2 | 9/2013 | Prud'homme et al. |
| 8,532,933 B2 | 9/2013 | Duke et al. |
| 8,548,544 B2 | 10/2013 | Kircher, Jr. et al. |
| 8,571,801 B2 | 10/2013 | Anfinsen et al. |
| 8,579,879 B2 | 11/2013 | Palerm et al. |
| 8,600,682 B2 | 12/2013 | Bashan et al. |
| 8,635,054 B2 | 1/2014 | Brown |
| 8,679,016 B2 | 3/2014 | Mastrototaro et al. |
| 8,690,934 B2 | 4/2014 | Boyden et al. |
| 8,700,161 B2 | 4/2014 | Harel et al. |
| 8,703,183 B2 | 4/2014 | Lara |
| 8,718,949 B2 | 5/2014 | Blomquist et al. |
| 8,755,938 B2 | 6/2014 | Weinert et al. |
| 8,766,803 B2 | 7/2014 | Bousamra et al. |
| 8,828,390 B2 | 9/2014 | Herrera et al. |
| 8,834,367 B2 | 9/2014 | Laan et al. |
| 8,870,807 B2 | 10/2014 | Mantri et al. |
| 8,911,367 B2 | 12/2014 | Brister et al. |
| 8,919,180 B2 | 12/2014 | Gottlieb et al. |
| 8,992,464 B2 | 3/2015 | Bashan et al. |
| 10,733,154 B2 * | 8/2020 | Bousamra .......... A61B 5/14532 |
| 2001/0002269 A1 | 5/2001 | Zhao |
| 2003/0028089 A1 * | 2/2003 | Galley .............. A61B 5/14532 |
| | | 600/365 |
| 2003/0050621 A1 | 3/2003 | Lebel et al. |
| 2003/0199445 A1 | 10/2003 | Knudsen et al. |
| 2003/0208110 A1 | 11/2003 | Mault et al. |

| | | | |
|---|---|---|---|
| 2003/0208113 A1 * | 11/2003 | Mault ................... G16H 40/63 |
| | | 600/316 |
| 2004/0042272 A1 | 3/2004 | Kurata |
| 2004/0044272 A1 | 3/2004 | Moerman et al. |
| 2004/0054263 A1 | 3/2004 | Moerman et al. |
| 2005/0020681 A1 | 1/2005 | Takayama et al. |
| 2005/0049179 A1 | 3/2005 | Davidson et al. |
| 2005/0054818 A1 | 3/2005 | Brader et al. |
| 2005/0055010 A1 | 3/2005 | Pettis et al. |
| 2005/0096637 A1 | 5/2005 | Heruth |
| 2005/0171503 A1 | 8/2005 | Van Den Berghe et al. |
| 2005/0176621 A1 | 8/2005 | Brader et al. |
| 2005/0177398 A1 | 8/2005 | Watanabe et al. |
| 2005/0187749 A1 | 8/2005 | Singley |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0267195 A1 | 12/2005 | Mikoshiba et al. |
| 2005/0272640 A1 | 12/2005 | Doyle et al. |
| 2006/0040003 A1 | 2/2006 | Needleman et al. |
| 2006/0078593 A1 | 4/2006 | Strozier et al. |
| 2006/0160722 A1 | 7/2006 | Green et al. |
| 2006/0173260 A1 | 8/2006 | Gaoni et al. |
| 2006/0188995 A1 | 8/2006 | Ryan et al. |
| 2006/0224109 A1 | 10/2006 | Steil et al. |
| 2006/0264895 A1 | 11/2006 | Flanders |
| 2007/0036872 A1 | 2/2007 | Tsuboi et al. |
| 2007/0060796 A1 | 3/2007 | Kim |
| 2007/0078314 A1 | 4/2007 | Grounsell et al. |
| 2007/0078818 A1 | 4/2007 | Zivitz et al. |
| 2007/0160678 A1 | 7/2007 | Guimberteau et al. |
| 2007/0168224 A1 | 7/2007 | Letzt et al. |
| 2007/0179434 A1 * | 8/2007 | Weinert ................. G16H 20/10 |
| | | 600/504 |
| 2007/0249916 A1 | 10/2007 | Pesach et al. |
| 2007/0282186 A1 | 12/2007 | Gilmore |
| 2007/0293742 A1 | 12/2007 | Simonsen et al. |
| 2008/0097289 A1 | 4/2008 | Steil et al. |
| 2008/0119421 A1 | 5/2008 | Tuszynski et al. |
| 2008/0119705 A1 | 5/2008 | Patel et al. |
| 2008/0139511 A1 | 6/2008 | Friesen |
| 2008/0139907 A1 | 6/2008 | Rao et al. |
| 2008/0172030 A1 | 7/2008 | Blomquist |
| 2008/0188796 A1 | 8/2008 | Steil et al. |
| 2008/0214919 A1 | 9/2008 | Harmon et al. |
| 2008/0228056 A1 * | 9/2008 | Blomquist .......... A61M 5/1723 |
| | | 600/365 |
| 2008/0234943 A1 | 9/2008 | Ray et al. |
| 2008/0255707 A1 | 10/2008 | Hebblewhite et al. |
| 2008/0269585 A1 | 10/2008 | Ginsberg |
| 2008/0299079 A1 | 12/2008 | Meezan et al. |
| 2008/0306353 A1 | 12/2008 | Douglas et al. |
| 2009/0006061 A1 * | 1/2009 | Thukral ................. G16H 50/20 |
| | | 703/11 |
| 2009/0029933 A1 | 1/2009 | Velloso et al. |
| 2009/0036753 A1 * | 2/2009 | King ................... A61B 5/14532 |
| | | 600/301 |
| 2009/0054753 A1 | 2/2009 | Robinson et al. |
| 2009/0069636 A1 | 3/2009 | Zivitz et al. |
| 2009/0099438 A1 | 4/2009 | Flanders |
| 2009/0110752 A1 | 4/2009 | Shang et al. |
| 2009/0157430 A1 | 6/2009 | Rule et al. |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0240127 A1 | 9/2009 | Ray |
| 2009/0242399 A1 | 10/2009 | Kamath et al. |
| 2009/0247982 A1 | 10/2009 | Krulevitch et al. |
| 2009/0253970 A1 | 10/2009 | Bashan et al. |
| 2009/0253973 A1 | 10/2009 | Bashan et al. |
| 2009/0281519 A1 | 11/2009 | Rao et al. |
| 2009/0299152 A1 | 12/2009 | Taub et al. |
| 2009/0312250 A1 | 12/2009 | Ryu et al. |
| 2010/0016700 A1 | 1/2010 | Sieh et al. |
| 2010/0035795 A1 | 2/2010 | Boss et al. |
| 2010/0137788 A1 | 6/2010 | Braithwaite et al. |
| 2010/0145725 A1 | 6/2010 | Alferness et al. |
| 2010/0160740 A1 | 6/2010 | Cohen et al. |
| 2010/0161236 A1 | 6/2010 | Cohen et al. |

(56)  References Cited

U.S. PATENT DOCUMENTS

| | | | |
|---|---|---|---|
| 2010/0161346 A1 | 6/2010 | Getschmann et al. |
| 2010/0168660 A1 | 7/2010 | Galley et al. |
| 2010/0198142 A1 | 8/2010 | Sloan et al. |
| 2010/0256047 A1 | 10/2010 | Sieh et al. |
| 2010/0262434 A1* | 10/2010 | Shaya ................. A61B 5/7475 |
| | | 705/3 |
| 2010/0286601 A1 | 11/2010 | Yodfat et al. |
| 2010/0305545 A1 | 12/2010 | Kanderian, Jr. et al. |
| 2010/0324382 A1 | 12/2010 | Cantwell et al. |
| 2010/0331652 A1 | 12/2010 | Groll et al. |
| 2010/0331654 A1 | 12/2010 | Jerdonek et al. |
| 2010/0332142 A1 | 12/2010 | Shadforth et al. |
| 2011/0021894 A1 | 1/2011 | Mohanty et al. |
| 2011/0071365 A1 | 3/2011 | Lee et al. |
| 2011/0071464 A1 | 3/2011 | Palerm |
| 2011/0098548 A1 | 4/2011 | Budiman et al. |
| 2011/0115894 A1 | 5/2011 | Burnett |
| 2011/0119081 A1 | 5/2011 | Vespasiani |
| 2011/0152830 A1 | 6/2011 | Ruchti et al. |
| 2011/0178008 A1 | 7/2011 | Arai et al. |
| 2011/0213332 A1 | 9/2011 | Mozayeny |
| 2011/0217396 A1 | 9/2011 | Oldani |
| 2011/0218489 A1 | 9/2011 | Mastrototaro et al. |
| 2011/0229602 A1 | 9/2011 | Aymard et al. |
| 2011/0286984 A1 | 11/2011 | Huang |
| 2011/0305771 A1 | 12/2011 | Sampalis |
| 2011/0313674 A1 | 12/2011 | Duke et al. |
| 2011/0319322 A1 | 12/2011 | Bashan et al. |
| 2012/0003339 A1 | 1/2012 | Minacapelli |
| 2012/0022353 A1 | 1/2012 | Bashan et al. |
| 2012/0046606 A1 | 2/2012 | Arefieg |
| 2012/0053222 A1 | 3/2012 | Gorrell et al. |
| 2012/0058942 A1 | 3/2012 | Dupre |
| 2012/0065482 A1 | 3/2012 | Robinson et al. |
| 2012/0095311 A1 | 4/2012 | Ramey et al. |
| 2012/0123234 A1 | 5/2012 | Atlas et al. |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0232520 A1 | 9/2012 | Sloan et al. |
| 2012/0238853 A1 | 9/2012 | Arefieg |
| 2012/0244096 A1 | 9/2012 | Xie et al. |
| 2012/0295985 A1 | 11/2012 | Miller et al. |
| 2013/0022592 A1 | 1/2013 | Vaughn et al. |
| 2013/0030358 A1 | 1/2013 | Yodfat et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0158503 A1 | 6/2013 | Kanderian, Jr. et al. |
| 2013/0165901 A1 | 6/2013 | Ruchti et al. |
| 2013/0172707 A1* | 7/2013 | Galley ............... A61B 5/14532 |
| | | 600/365 |
| 2013/0190583 A1 | 7/2013 | Grosman et al. |
| 2013/0225683 A1 | 8/2013 | Gagnon et al. |
| 2013/0233727 A1 | 9/2013 | Tsai et al. |
| 2013/0245547 A1 | 9/2013 | El-Khatib et al. |
| 2013/0267796 A1 | 10/2013 | Enric Monte Moreno |
| 2013/0281796 A1 | 10/2013 | Pan |
| 2013/0282301 A1 | 10/2013 | Rush |
| 2013/0289883 A1 | 10/2013 | Bashan et al. |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0338630 A1* | 12/2013 | Agrawal ............. A61M 5/1723 |
| | | 604/504 |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0024907 A1 | 1/2014 | Howell et al. |
| 2014/0037749 A1 | 2/2014 | Shea et al. |
| 2014/0057331 A1 | 2/2014 | Tajima et al. |
| 2014/0066735 A1 | 3/2014 | Engelhardt et al. |

| | | | |
|---|---|---|---|
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0296943 A1 | 10/2014 | Maxik et al. |
| 2014/0303466 A1 | 10/2014 | Fitzpatrick et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |
| 2014/0349256 A1 | 11/2014 | Connor |
| 2014/0349257 A1 | 11/2014 | Connor |
| 2014/0356420 A1 | 12/2014 | Huang |
| 2014/0363794 A1 | 12/2014 | Angelides |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |
| 2015/0025903 A1 | 1/2015 | Mueller-Wolf |
| 2015/0031053 A1 | 1/2015 | Moerman |
| 2015/0037406 A1 | 2/2015 | Bernabeu Martinez et al. |

FOREIGN PATENT DOCUMENTS

| | | | |
|---|---|---|---|
| AU | 2010330746 A1 | 7/2012 |
| CA | 2519249 A1 | 10/2004 |
| CA | 2670512 A1 | 7/2008 |
| CA | 2720302 A1 | 12/2009 |
| CA | 2720304 A1 | 12/2009 |
| CA | 2733593 A1 | 2/2010 |
| CA | 2752637 A1 | 9/2010 |
| CA | 2761647 A1 | 12/2010 |
| CA | 2766944 A1 | 1/2011 |
| CA | 2784143 A1 | 6/2011 |
| CN | 102016855 A | 4/2011 |
| CN | 102016906 A | 4/2011 |
| CN | 102300501 A | 12/2011 |
| CN | 102395310 A | 3/2012 |
| CN | 102481101 A | 5/2012 |
| CN | 102946804 A | 2/2013 |
| DE | 1082412 T1 | 10/2001 |
| EP | 461207 A1 | 12/1991 |
| EP | 483595 A2 | 5/1992 |
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1082412 A2 | 3/2001 |
| EP | 1115389 A1 | 7/2001 |
| EP | 483595 | 12/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1610758 A2 | 1/2006 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 1921981 A2 | 5/2008 |
| EP | 2114491 A1 | 11/2009 |

(56) References Cited

FOREIGN PATENT DOCUMENTS

| | | | |
|---|---|---|---|
| EP | 2129277 | A2 | 12/2009 |
| EP | 2139393 | A2 | 1/2010 |
| EP | 2170430 | A2 | 4/2010 |
| EP | 2257218 | A2 | 12/2010 |
| EP | 2260423 | A2 | 12/2010 |
| EP | 2260462 | A2 | 12/2010 |
| EP | 2276405 | A1 | 1/2011 |
| EP | 2300046 | A2 | 3/2011 |
| EP | 2328608 | A2 | 6/2011 |
| EP | 2352456 | A1 | 8/2011 |
| EP | 2355669 | A2 | 8/2011 |
| EP | 2377465 | A1 | 10/2011 |
| EP | 2384750 | A1 | 11/2011 |
| EP | 2393419 | A1 | 12/2011 |
| EP | 2400882 | A1 | 1/2012 |
| EP | 2418972 | A1 | 2/2012 |
| EP | 2442719 | A2 | 4/2012 |
| EP | 2448432 | A1 | 5/2012 |
| EP | 2448468 | A1 | 5/2012 |
| EP | 2448469 | A2 | 5/2012 |
| EP | 2482712 | A1 | 8/2012 |
| EP | 2516671 | A1 | 10/2012 |
| EP | 2518655 | A2 | 10/2012 |
| EP | 2525863 | A1 | 11/2012 |
| EP | 2535831 | A1 | 12/2012 |
| EP | 2552313 | A2 | 2/2013 |
| EP | 2582297 | A1 | 4/2013 |
| EP | 2585133 | A1 | 5/2013 |
| EP | 2590559 | A2 | 5/2013 |
| EP | 2596448 | A1 | 5/2013 |
| EP | 2603133 | A1 | 6/2013 |
| EP | 2605819 | A1 | 6/2013 |
| EP | 2640373 | A1 | 9/2013 |
| EP | 2641084 | A1 | 9/2013 |
| EP | 2644088 | A1 | 10/2013 |
| EP | 2654777 | A2 | 10/2013 |
| EP | 2659407 | A1 | 11/2013 |
| EP | 2666369 | A1 | 11/2013 |
| EP | 2685895 | A1 | 1/2014 |
| EP | 2720713 | A2 | 4/2014 |
| EP | 2736404 | A1 | 6/2014 |
| EP | 2742447 | A2 | 6/2014 |
| EP | 2742449 | A2 | 6/2014 |
| EP | 2745225 | A2 | 6/2014 |
| EP | 2760335 | A1 | 8/2014 |
| EP | 2763722 | A2 | 8/2014 |
| EP | 2798548 | A1 | 11/2014 |
| EP | 2822647 | A1 | 1/2015 |
| JP | 2004024699 | A | 1/2004 |
| JP | 2008524591 | A | 7/2008 |
| JP | 4594731 | B2 | 12/2010 |
| JP | 04800928 | B2 | 10/2011 |
| JP | 2012210366 | A | 11/2012 |
| KR | 100527154 | B1 | 11/2005 |
| KR | 1020090095073 | | 9/2009 |
| KR | 2011052664 | A | 5/2011 |
| KR | 2012047841 | A | 5/2012 |
| RU | 2011109016 | A | 9/2012 |
| WO | 1992019260 | A1 | 11/1992 |
| WO | 1996009823 | A1 | 4/1996 |
| WO | 1999044496 | A1 | 9/1999 |
| WO | 1999063101 | A2 | 12/1999 |
| WO | 2002036139 | | 5/2002 |
| WO | 2003024468 | | 3/2003 |
| WO | 2003077895 | | 9/2003 |
| WO | 2003094927 | | 11/2003 |
| WO | 2004084820 | A2 | 10/2004 |
| WO | 2005041022 | A1 | 5/2005 |
| WO | 2005081119 | A2 | 9/2005 |
| WO | 2005081170 | A2 | 9/2005 |
| WO | 2005081171 | A2 | 9/2005 |
| WO | 2005081173 | A1 | 9/2005 |
| WO | 2005110222 | A1 | 11/2005 |
| WO | 2006022619 | A2 | 3/2006 |
| WO | 2006022629 | A1 | 3/2006 |
| WO | 2006022633 | A1 | 3/2006 |
| WO | 2006022634 | A1 | 3/2006 |
| WO | 2006022636 | A1 | 3/2006 |
| WO | 2006022638 | A1 | 3/2006 |
| WO | 2006044556 | A2 | 4/2006 |
| WO | 2003101177 | | 7/2006 |
| WO | 2006079124 | A2 | 7/2006 |
| WO | 2006091918 | A2 | 8/2006 |
| WO | 2006130901 | A1 | 12/2006 |
| WO | 2007116226 | A2 | 10/2007 |
| WO | 2007149533 | A2 | 12/2007 |
| WO | 2008005761 | A2 | 1/2008 |
| WO | 2008013324 | A1 | 1/2008 |
| WO | 2008057213 | A2 | 5/2008 |
| WO | 2008057384 | A2 | 5/2008 |
| WO | 2008067245 | A2 | 6/2008 |
| WO | 2008088490 | A1 | 7/2008 |
| WO | 2008112078 | A2 | 9/2008 |
| WO | 2008124478 | A1 | 10/2008 |
| WO | 2009002455 | A1 | 12/2008 |
| WO | 2009005960 | A2 | 1/2009 |
| WO | 2009075925 | A1 | 6/2009 |
| WO | 2009139846 | A1 | 11/2009 |
| WO | 2009146119 | A2 | 12/2009 |
| WO | 2009146121 | A2 | 12/2009 |
| WO | 2010021879 | A2 | 2/2010 |
| WO | 2010056718 | A2 | 5/2010 |
| WO | 2010075350 | A1 | 7/2010 |
| WO | 2010089304 | A1 | 8/2010 |
| WO | 2010089305 | A1 | 8/2010 |
| WO | 2010089306 | A1 | 8/2010 |
| WO | 2010089307 | A1 | 8/2010 |
| WO | 2010091102 | A1 | 8/2010 |
| WO | 2010097796 | A1 | 9/2010 |
| WO | 2010135646 | A1 | 11/2010 |
| WO | 2010147659 | A2 | 12/2010 |
| WO | 2011008520 | A2 | 1/2011 |
| WO | 2011037607 | A2 | 3/2011 |
| WO | 2011075687 | A1 | 6/2011 |
| WO | 2011089600 | A1 | 7/2011 |
| WO | 2011094352 | A1 | 8/2011 |
| WO | 2011157402 | A1 | 12/2011 |
| WO | 2012023964 | A1 | 2/2012 |
| WO | 2012047800 | A1 | 4/2012 |
| WO | 2012065556 | A1 | 5/2012 |
| WO | 2012097064 | A1 | 7/2012 |
| WO | 2012122520 | A1 | 9/2012 |
| WO | 2012148252 | A2 | 11/2012 |
| WO | 2012161670 | A2 | 11/2012 |
| WO | 2012177963 | A1 | 12/2012 |
| WO | 2013040712 | A1 | 3/2013 |
| WO | 2013050309 | A1 | 4/2013 |
| WO | 2013086372 | A1 | 6/2013 |
| WO | 2013096769 | A1 | 6/2013 |
| WO | 2013108262 | A1 | 7/2013 |
| WO | 2013134548 | A2 | 9/2013 |
| WO | 2013172833 | A1 | 11/2013 |
| WO | 2013177565 | A1 | 11/2013 |
| WO | 2014011488 | A2 | 1/2014 |
| WO | 2014012084 | A1 | 1/2014 |
| WO | 2014023834 | A2 | 2/2014 |
| WO | 2014024201 | A1 | 2/2014 |
| WO | 2014028607 | A1 | 2/2014 |
| WO | 2014068007 | A1 | 5/2014 |
| WO | 2014075135 | | 5/2014 |
| WO | 2014075135 | A1 | 5/2014 |
| WO | 2014099829 | | 6/2014 |
| WO | 2014099829 | A1 | 6/2014 |
| WO | 2014106263 | A2 | 7/2014 |
| WO | 2014145049 | A2 | 9/2014 |
| WO | 2014149535 | | 9/2014 |
| WO | 2014149535 | A1 | 9/2014 |
| WO | 2014149781 | A1 | 9/2014 |
| WO | 2014152704 | A1 | 9/2014 |
| WO | 2014162549 | A1 | 10/2014 |
| WO | 2014164226 | A2 | 10/2014 |
| WO | 2014179171 | A1 | 11/2014 |
| WO | 2014187812 | A1 | 11/2014 |
| WO | 2014190231 | A1 | 11/2014 |

(56) References Cited

FOREIGN PATENT DOCUMENTS

WO          2014202024  A1      12/2014
WO          2014209630  A2      12/2014
WO          2014209634  A1      12/2014

OTHER PUBLICATIONS

Kim, Sarah et al., Hyperglycemia control of the Nil per os patient in the intensive care unit: Introduction of a simple subcutaneous insulin algorithm, Journal of Diabetes Science and Technology, Nov. 2012, vol. 6, Issue 6, pp. 1413-1419.
Vaidya, Anand et al., "Improving the management of diabetes in hospitalized patients: The result of a computer-based house staff training program", Diabetes Technology & Therapeutics, 2012, vol. 14, No. 7, pp. 610-618.

Lee, Joshua et al., "Indication-based ordering: A new paradigm for glycemic control in hospitalized inpatients", Journal of Diabetes Science and Technology, May 2008, vol. 2, Issue 3, pp. 349-356.
Nau, Konrad C. et al, "Glycemic Control in hospitalized patients not in intensive care: Beyond sliding-scale insulin", American Family Physician, May 1, 2010, vol. 81, No. 9, pp. 1130-1133.
International Search Report and Written Opinion for Application No. PCT/US2015/011559 dated Apr. 29, 2015.
International Search Report and Written Opinion for Application No. PCT/US2015/011086 dated Apr. 29, 2015.
International Search Report and Written Opinion for Application No. PCT/US2015/011574 dated Apr. 24, 2015.
International Search Report and Written Opinion for Application No. PCT/US2016/047806 dated Nov. 25, 2016.
Japanese Office Action for the related Application No. 2016-549782 dated May 16, 2019.

* cited by examiner

208a 116,146

216

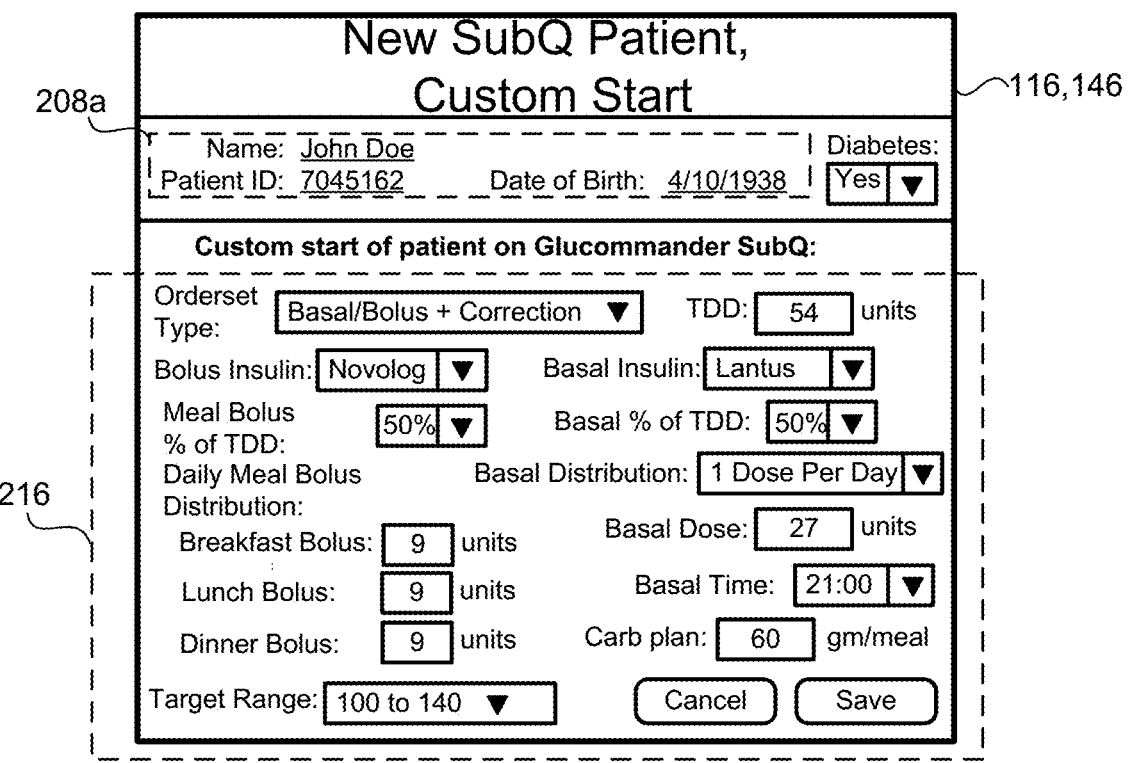

New SubQ Patient, Custom Start

Name: John Doe

Patient ID: 7045162        Date of Birth: 4/10/1938

Diabetes: Yes ▼

Custom start of patient on Glucommander SubQ:

Orderset Type: Basal/Bolus + Correction ▼        TDD: 54 units

Bolus Insulin: Novolog ▼        Basal Insulin: Lantus ▼

Meal Bolus % of TDD: 50% ▼        Basal % of TDD: 50% ▼

Daily Meal Bolus Distribution:        Basal Distribution: 1 Dose Per Day ▼

Breakfast Bolus: 9 units        Basal Dose: 27 units

Lunch Bolus: 9 units        Basal Time: 21:00 ▼

Dinner Bolus: 9 units        Carb plan: 60 gm/meal

Target Range: 100 to 140 ▼        Cancel        Save

Figure 2F:
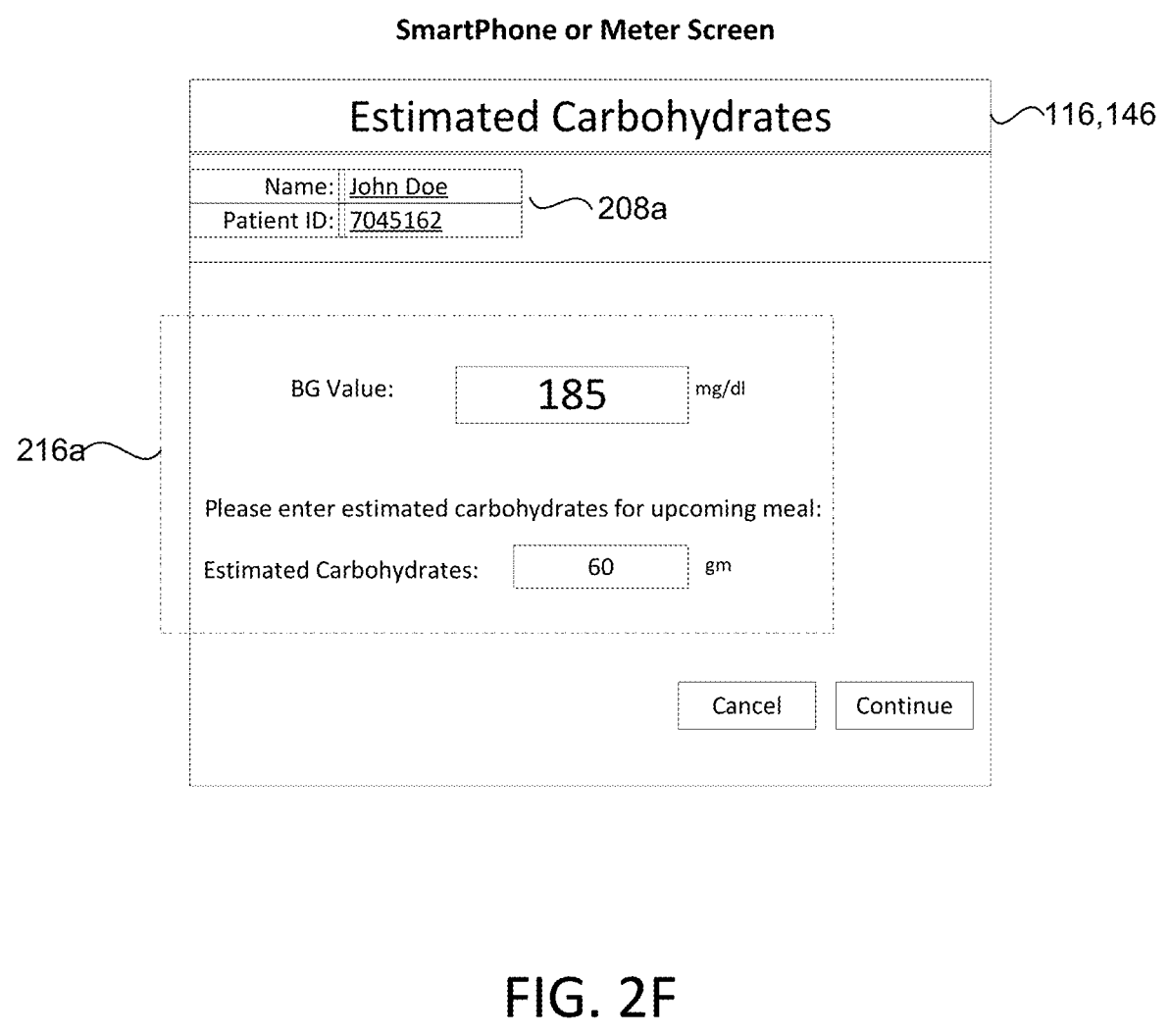

SmartPhone or Meter Screen

Estimated Carbohydrates          ⟋116,146

| Name: | John Doe |
|---|---|
| Patient ID: | 7045162 |

⟋208a

BG Value:          185          mg/dl

216a

Please enter estimated carbohydrates for upcoming meal:

Estimated Carbohydrates:          60          gm

Cancel          Continue

Figure 2G:
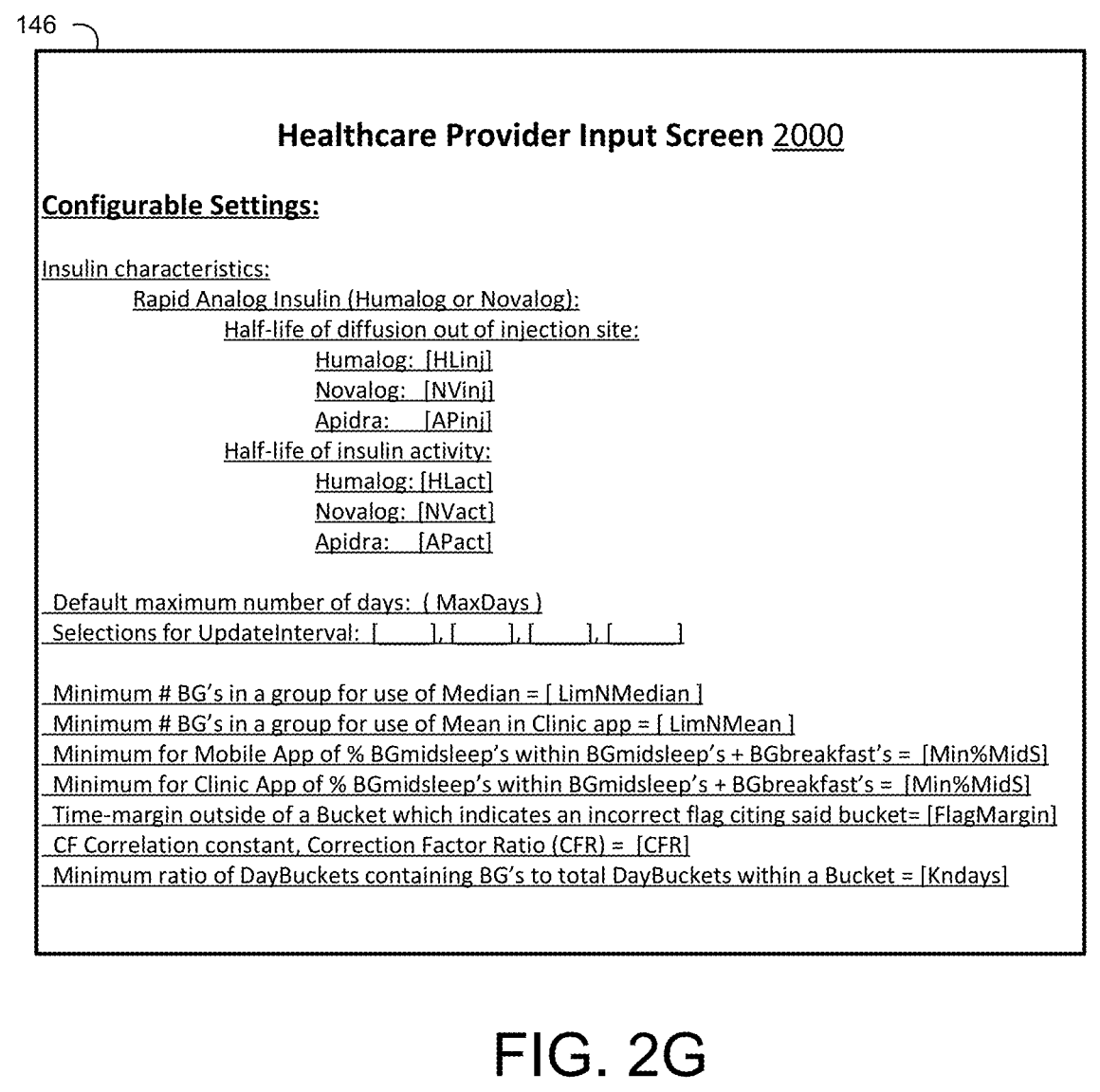

Healthcare Provider Input Screen 2000

Configurable Settings:

Insulin characteristics:
        Rapid Analog Insulin (Humalog or Novalog):
                Half-life of diffusion out of injection site:
                        Humalog: [HLinj]
                        Novalog:  [NVinj]
                        Apidra:    [APinj]
                Half-life of insulin activity:
                        Humalog: [HLact]
                        Novalog: [NVact]
                        Apidra:    [APact]

Default maximum number of days: ( MaxDays )
 Selections for UpdateInterval: [     ], [     ], [     ], [     ]

Minimum # BG's in a group for use of Median = [ LimNMedian ]
 Minimum # BG's in a group for use of Mean in Clinic app = [ LimNMean ]
 Minimum for Mobile App of % BGmidsleep's within BGmidsleep's + BGbreakfast's = [Min%MidS]
 Minimum for Clinic App of % BGmidsleep's within BGmidsleep's + BGbreakfast's = [Min%MidS]
 Time-margin outside of a Bucket which indicates an incorrect flag citing said bucket= [FlagMargin]
 CF Correlation constant, Correction Factor Ratio (CFR) = [CFR]
 Minimum ratio of DayBuckets containing BG's to total DayBuckets within a Bucket = [Kndays]

FIG. 2G 116,146

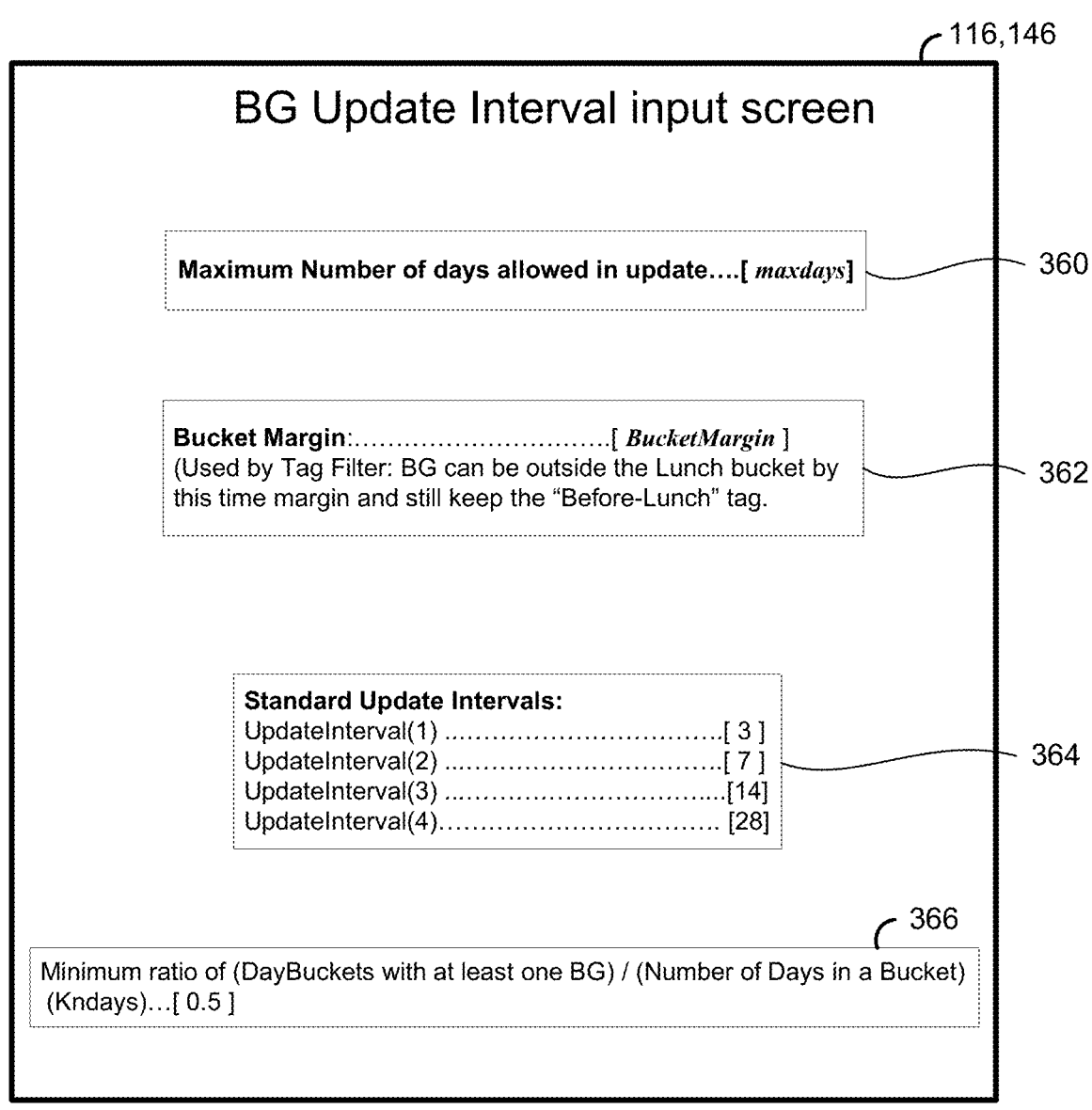

BG Update Interval input screen

Maximum Number of days allowed in update....[ *maxdays*]      360

Bucket Margin:............................[ *BucketMargin* ]
(Used by Tag Filter: BG can be outside the Lunch bucket by
this time margin and still keep the "Before-Lunch" tag.      362

Standard Update Intervals:
UpdateInterval(1) ....................................[ 3 ]
UpdateInterval(2) ....................................[ 7 ]
UpdateInterval(3) ....................................[14]
UpdateInterval(4)....................................[28]      364

366

Minimum ratio of (DayBuckets with at least one BG) / (Number of Days in a Bucket)
(Kndays)...[ 0.5 ]

BG Filtering & Aggregation Options

|  | ON | OFF |
|---|---|---|
| Tag Filter | ⦿ | ○ |
| Bolus-Time Filter | ⦿ | ○ |
| Ideal Mealtime Filter | ⦿ | ○ |
| Whole Bucket Filter | ○ | ⦿ |

⌒ 370

DayBucket Aggregation Method:

Minimum of filtered BG's in DayBucket........ ⦿
Earliest of filtered BG's in DayBucket.......... ○
Mean of filtered BG's in DayBucket............ ○
Median of filtered BG's in DayBucket...... ○

⌒ 372

Bucket Aggregation Method:

Fewest & Lowest DayBuckets...................... ⦿

Mean of DayBucket Aggregates........................... ○

Median of DayBucket Aggregates (not available for 3-day update interval) ..................................................... ○

Automatic Mean or Median.................................. ⦿

⌒ 374

TimeMealBolus Selector

Time of Earliest Bolus............................. ⦿
(BolTimeType=0)

Time of Largest Bolus................. ○
(BolTimeType=1)

TimeMealBolus Selection Process

300

380 — From Block 376 (FIG. 2J)

BolTimeType (0,1)

382 — BolTimeType=0

YES

NO

384 — TimeMealBolus=[time of earliest bolus in the daybucket]

386 — TimeMealBolus=[time of largest bolus in daybucket]

388 — Bolus Time Filter 1600d (FIG. 16D)

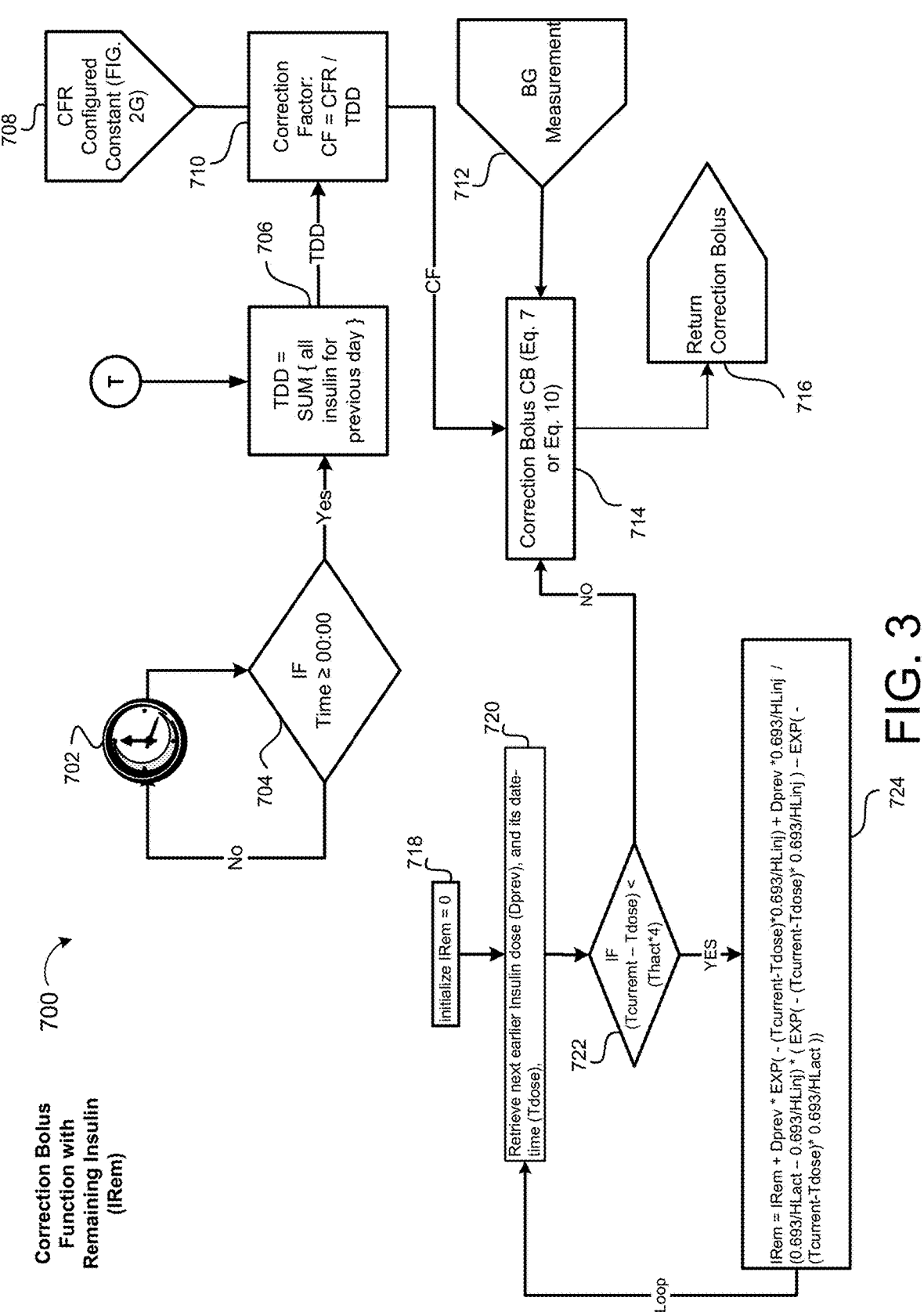

Correction Bolus Function with Remaining Insulin (IRem)

700

702

704 — IF Time ≥ 00:00 — No

706 — TDD = SUM { all insulin for previous day } — TDD

708 — CFR Configured Constant (FIG. 2G)

710 — Correction Factor: CF = CFR / TDD — CF

712 — BG Measurement

714 — Correction Bolus CB (Eq. 7 or Eq. 10)

716 — Return Correction Bolus

718 — Initialize IRem = 0

720 — Retrieve next earlier insulin dose (Dprev), and its date-time (Tdose).

722 — IF (Tcurrent – Tdose) < (Thact*4) — NO / YES

724 — IRem = IRem + Dprev * EXP( - (Tcurrent-Tdose)*0.693/HLinj ) + Dprev * 0.693/HLinj / (0.693/HLact – 0.693/HLinj) * ( EXP( - (Tcurrent-Tdose)* 0.693/HLinj ) – EXP( - (Tcurrent-Tdose)* 0.693/HLact )) — Loop Yes

FIG. 3

Where the values of the BG limits and Adjustment Factors (AF) are in accordance with Fig 4A, and the values for AF are currently configured at:
    AF1=0.8,  AF2=0.9,  AF3=1.0,  AF4=1.1,  AF5=1.2,  AF6=1.3

Adjustment Factor (AF) Function

Smart Meter

Smart Meter with Correction dose calculator

Limits on Age of Data for Adjustment

Flag Corrector Process

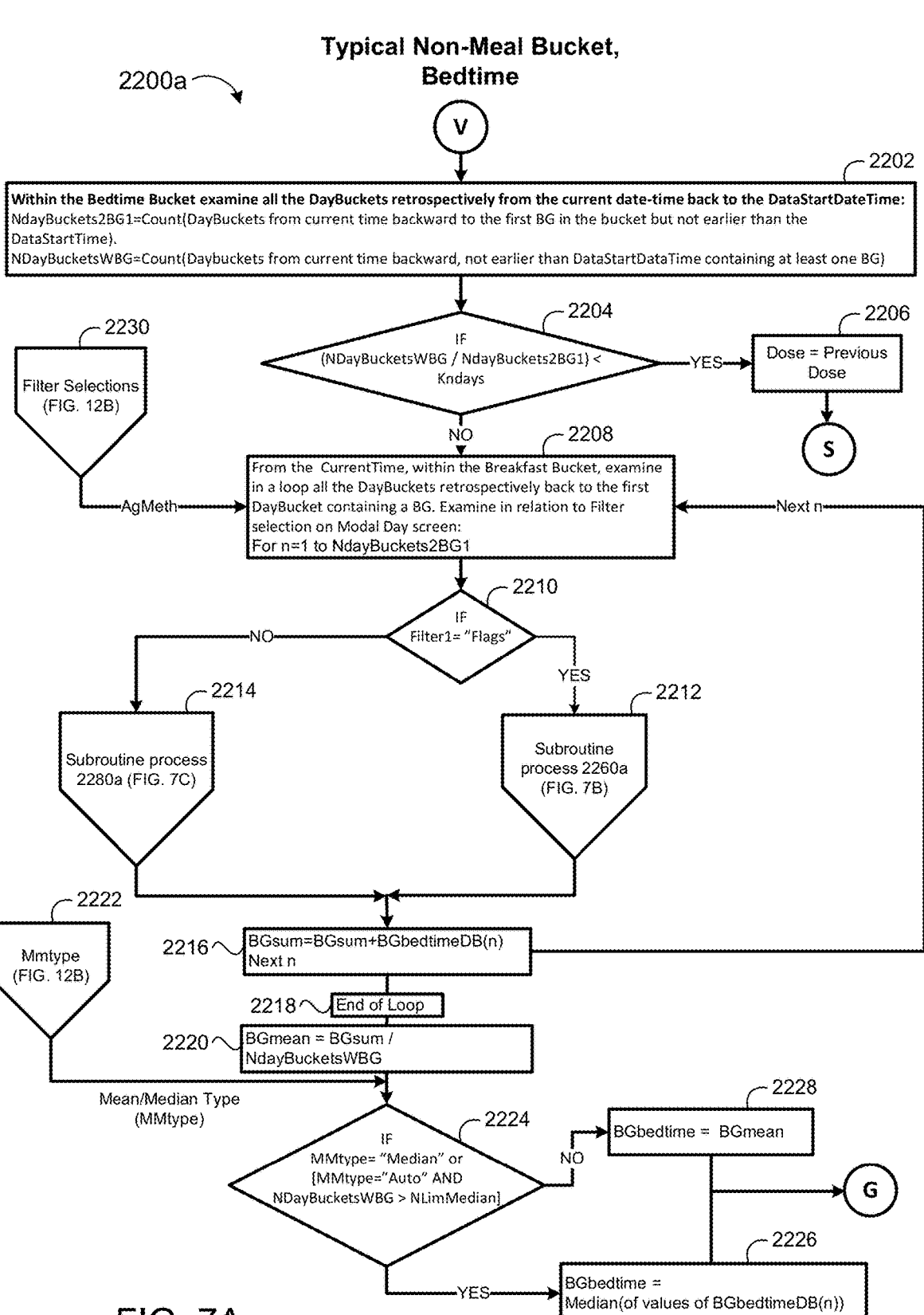

Typical Non-Meal Bucket, Bedtime

2200a ( V )

2202

Within the Bedtime Bucket examine all the DayBuckets retrospectively from the current date-time back to the DataStartDateTime:
NdayBuckets2BG1=Count(DayBuckets from current time backward to the first BG in the bucket but not earlier than the DataStartTime).
NDayBucketsWBG=Count(Daybuckets from current time backward, not earlier than DataStartDataTime containing at least one BG)

2204
IF
(NDayBucketsWBG / NdayBuckets2BG1) < Kndays

2206
YES → Dose = Previous Dose
( S )

2230
Filter Selections (FIG. 12B)

NO

2208
From the CurrentTime, within the Breakfast Bucket, examine in a loop all the DayBuckets retrospectively back to the first DayBucket containing a BG. Examine in relation to Filter selection on Modal Day screen:
For n=1 to NdayBuckets2BG1

←AgMeth→                                   ←Next n→

2210
IF
Filter1= "Flags"

NO                    YES

2214
Subroutine process 2280a (FIG. 7C)

2212
Subroutine process 2260a (FIG. 7B)

2222
Mmtype (FIG. 12B)

2216
BGsum=BGsum+BGbedtimeDB(n)
Next n

2218  End of Loop

2220
BGmean = BGsum / NdayBucketsWBG

Mean/Median Type (MMtype)

2224
IF
MMtype= "Median" or
{MMtype="Auto" AND
NDayBucketsWBG > NLimMedian}

2228
NO → BGbedtime = BGmean ( G )

2226
YES → BGbedtime = Median(of values of BGbedtimeDB(n))

FIG. 7A

**Typical Non-Meal Bucket,
Bedtime**

**Typical Non-Meal Bucket,
Bedtime**

Figure 7F:
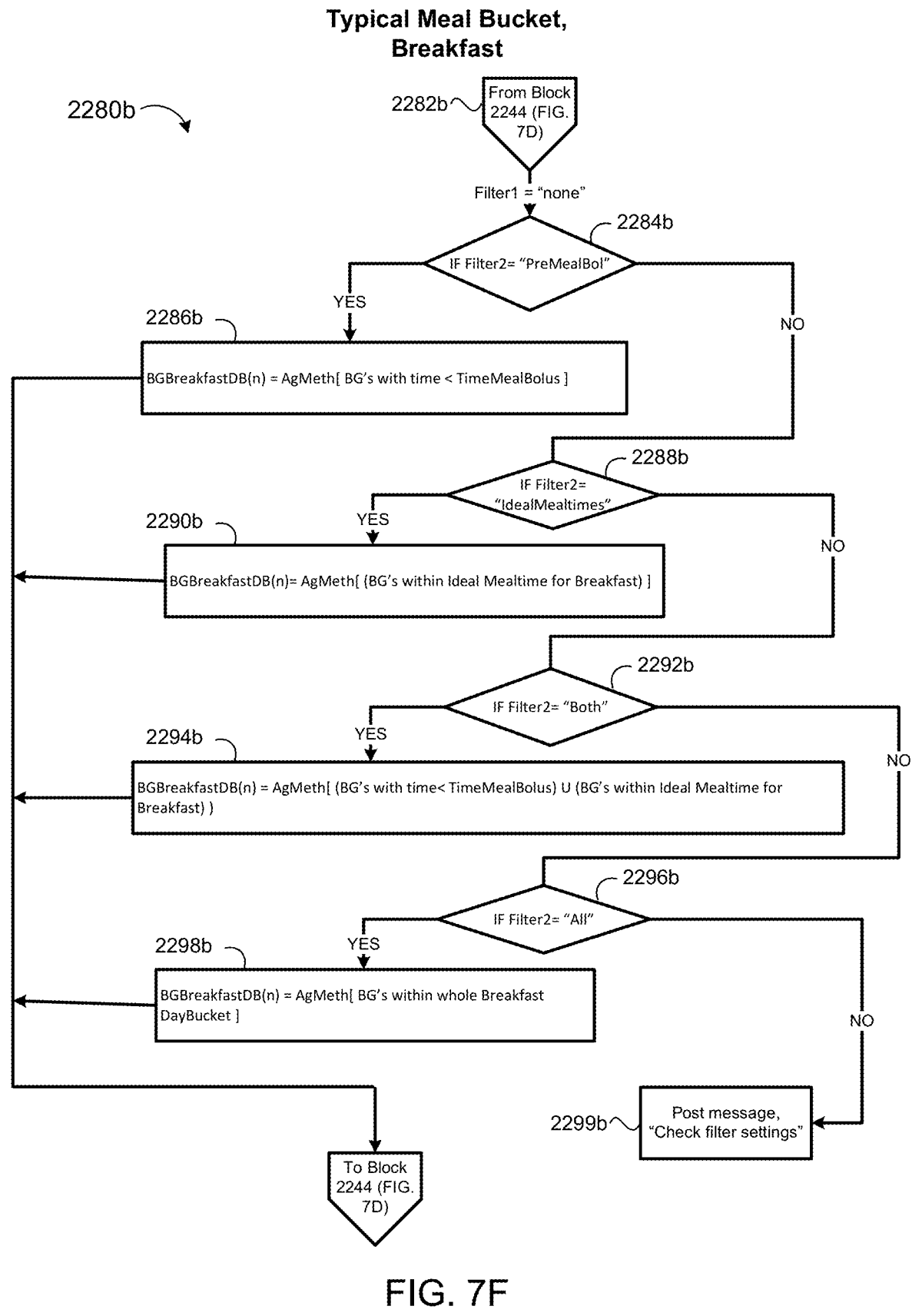

**Typical Meal Bucket,
Breakfast**

2280b

2282b — From Block 2244 (FIG. 7D)

Filter1 = "none"

2284b

IF Filter2= "PreMealBol"

YES / NO

2286b — BGBreakfastDB(n) = AgMeth[ BG's with time < TimeMealBolus ]

2288b

IF Filter2= "IdealMealtimes"

YES / NO

2290b — BGBreakfastDB(n)= AgMeth[ (BG's within Ideal Mealtime for Breakfast) ]

2292b

IF Filter2= "Both"

YES / NO

2294b — BGBreakfastDB(n) = AgMeth[ (BG's with time< TimeMealBolus) U (BG's within Ideal Mealtime for Breakfast) ]

2296b

IF Filter2= "All"

YES / NO

2298b — BGBreakfastDB(n) = AgMeth[ BG's within whole Breakfast DayBucket ]

2299b — Post message, "Check filter settings"

To Block 2244 (FIG. 7D)

RECEIVING SUBCUTANEOUS INFOMRATION FOR A PATIENT AT A COMPUTING DEVICE

1402

EXECUTING A SUBCUTANEOUS OUTPATIENT PROGRAM AT THE COMPUTING DEVICE

1404

OBTAINING BLOOD GLUCOSE DATA OF THE PATIENT FROM A GLUCOMETER

1406

DETERMINING A NEXT RECOMMENDED INSULIN DOSAGE FOR THE PATIENT

1408

Tag Filter

Erroneous BG Filter

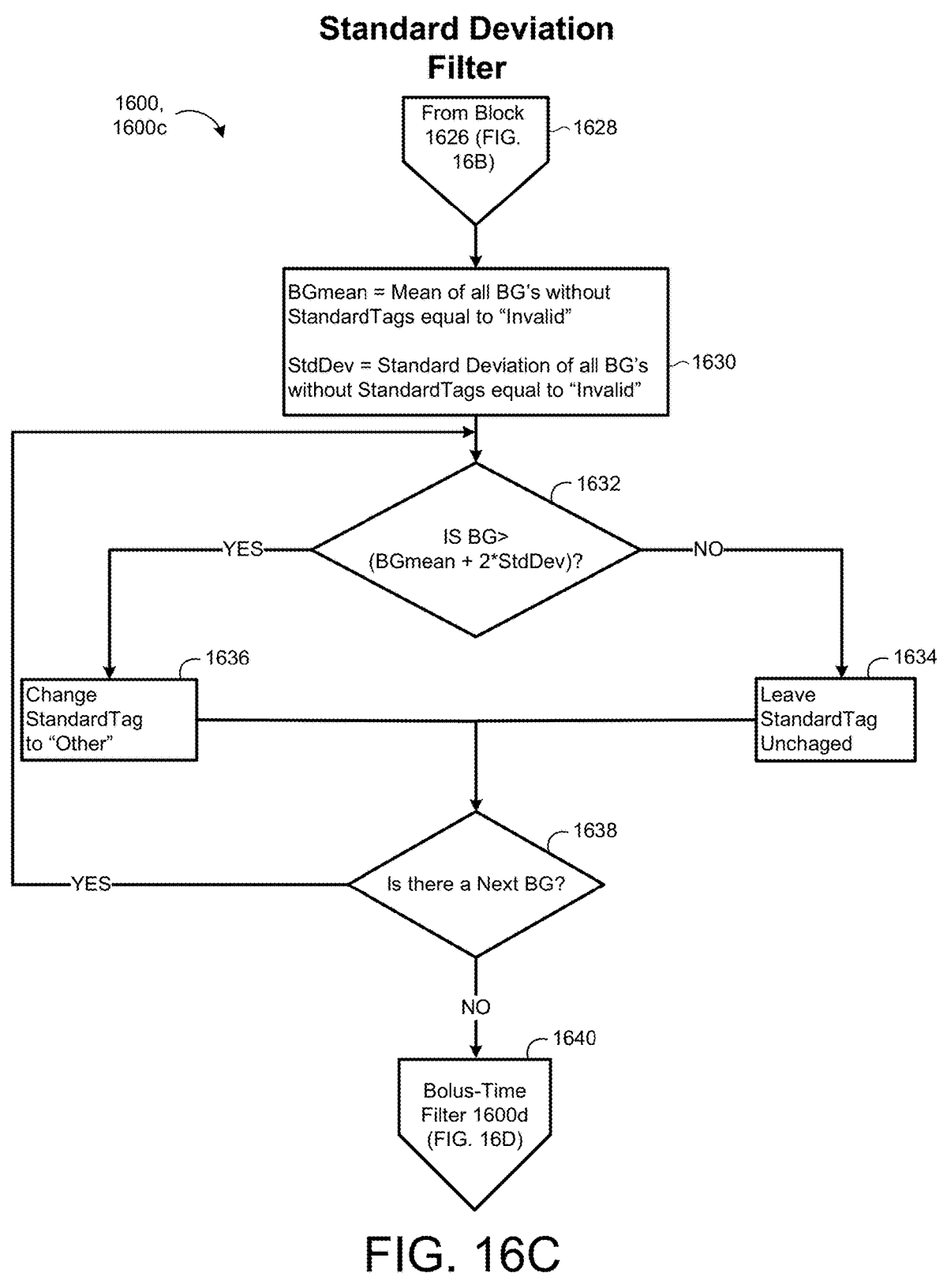

Standard Deviation Filter

1600, 1600c

From Block 1626 (FIG. 16B) — 1628

BGmean = Mean of all BG's without StandardTags equal to "Invalid"

StdDev = Standard Deviation of all BG's without StandardTags equal to "Invalid" — 1630

— 1632

IS BG> (BGmean + 2*StdDev)?

YES

NO

— 1636
Change StandardTag to "Other"

— 1634
Leave StandardTag Unchaged

— 1638
Is there a Next BG?

YES

NO

— 1640
Bolus-Time Filter 1600d (FIG. 16D)

FIG. 16C

Bolus-Time Filter

1600,
1600d

Ideal Mealtime Filter

Whole Bucket Filter

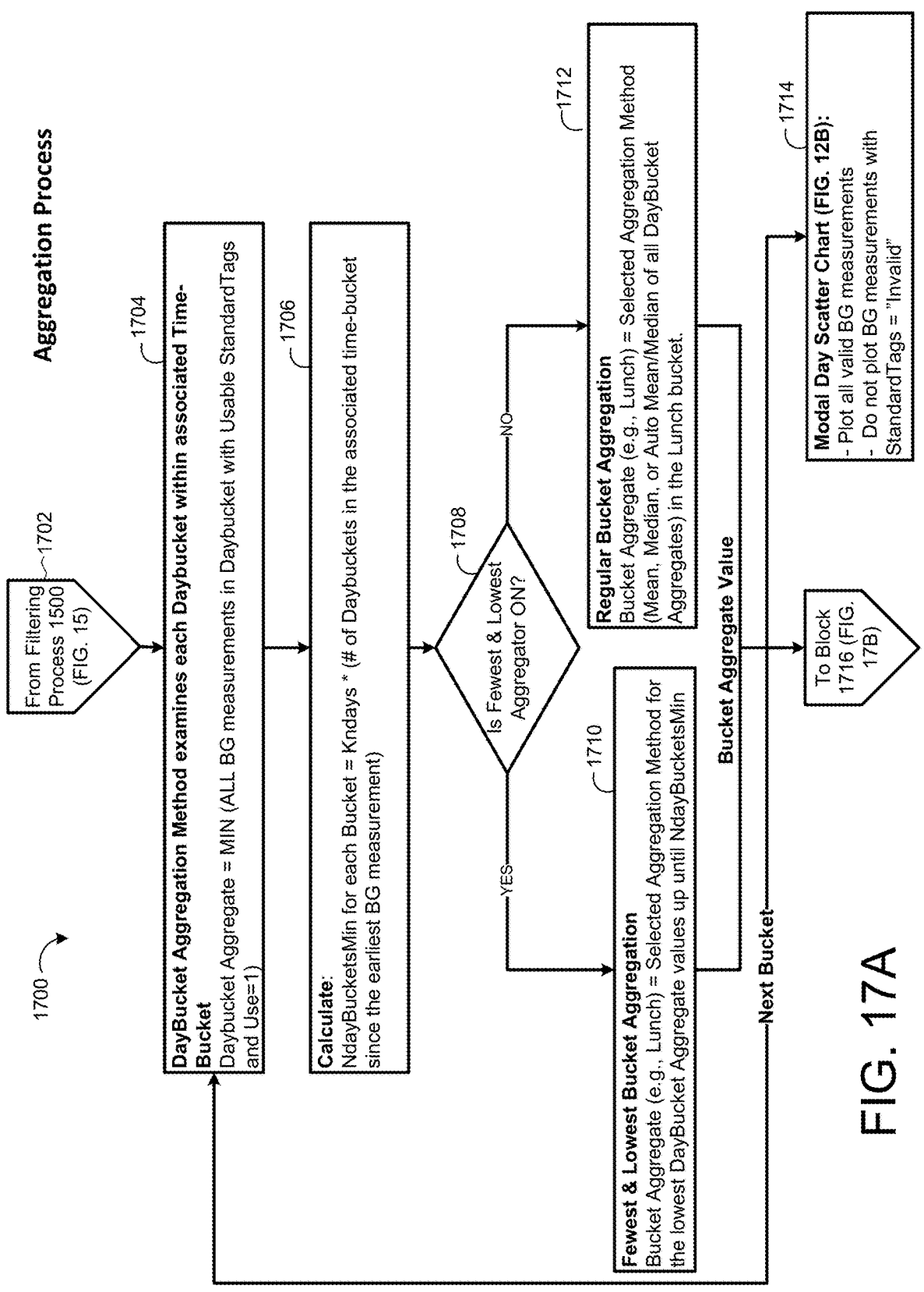

Aggregation Process

1700

From Filtering Process 1500 (FIG. 15)  1702

DayBucket Aggregation Method examines each Daybucket within associated Time-Bucket

Daybucket Aggregate = MIN (ALL BG measurements in Daybucket with Usable StandardTags and Use=1)  1704

Calculate:

NdayBucketsMin for each Bucket = Kndays * (# of Daybuckets in the associated time-bucket since the earliest BG measurement)  1706

Is Fewest & Lowest Aggregator ON?  1708

NO →

Regular Bucket Aggregation

Bucket Aggregate (e.g., Lunch) = Selected Aggregation Method (Mean, Median, or Auto Mean/Median of all DayBucket Aggregates) in the Lunch bucket.  1712

YES →

Fewest & Lowest Bucket Aggregation

Bucket Aggregate (e.g., Lunch) = Selected Aggregation Method for the lowest DayBucket Aggregate values up until NdayBucketsMin  1710

Modal Day Scatter Chart (FIG. 12B):
- Plot all valid BG measurements
- Do not plot BG measurements with StandardTags = "Invalid"  1714

Bucket Aggregate Value

To Block 1716 (FIG. 17B)

Next Bucket

FIG. 17A

METHOD AND DOSING CONTROLLER FOR ADMINISTERING A CORRECTION DOSE OF INSULIN

CROSS REFERENCE TO RELATED APPLICATIONS

This U.S. patent application is a continuation of, and claims priority under 35 U.S.C. § 120 from, U.S. application Ser. No. 17/305,658, filed on Jul. 12, 2021, which is a continuation of U.S. application Ser. No. 15/496,419, filed on Apr. 25, 2017, which is a continuation-in-part of, and claims priority under 35 U.S.C. § 120 from, U.S. application Ser. No. 14/922,763, filed on Oct. 26, 2015, which claims priority under 35 U.S.C. § 119(e) to U.S. Provisional Application No. 62/069,195, filed on Oct. 27, 2014. The disclosures of these prior applications are considered part of the disclosure of this application and are hereby incorporated by reference in their entireties.

TECHNICAL FIELD

This disclosure relates to a system for managing insulin administration or insulin dosing.

BACKGROUND

Managing diabetes requires calculating insulin doses for maintaining blood glucose measurements within desired ranges. Managing diabetes requires calculating insulin doses for maintaining blood glucose measurements within desired ranges. Manual calculation may not be accurate due to human error, which can lead to patient safety issues. Different institutions use multiple and sometimes conflicting protocols to manually calculate an insulin dosage. Moreover, the diabetic population includes many young children or elderly persons whom have difficulty understanding calculations for insulin doses.

SUMMARY

One aspect of the disclosure provides a method for subcutaneous outpatient management. The method includes receiving, at data processing hardware, scheduled blood glucose time intervals for a patient. Each scheduled blood glucose time interval is associated with a corresponding time boundary within a day that does not overlap time boundaries associated with the other scheduled blood glucose time intervals. The method also includes obtaining, at the data processing hardware, blood glucose data of the patient from a glucometer in communication with the data processing hardware. The blood glucose data includes blood glucose measurements of the patient. The blood glucose data also includes glucose times associated with a time of measuring a corresponding blood glucose measurement and insulin dosages previously administered by the patient and associated with the blood glucose measurements. The method also includes applying, by the data processing hardware, a set of filters to identify which of the blood glucose measurements associated with at least one of the scheduled blood glucose time intervals are usable and which of the blood glucose measurements associated with the at least one scheduled blood glucose time interval are unusable. The method further includes aggregating, by the data processing hardware, the blood glucose measurements associated with the at least one scheduled blood glucose time interval identified as usable by the set of filters to determine a representative aggregate blood glucose measurement associated with the at least one scheduled blood glucose time interval. The method further includes determining, by the data processing hardware, a next recommended insulin dosage for the patient based on the representative aggregate blood glucose measurement and the insulin dosages previously administered by the patient. The method also includes transmitting the next recommended insulin dosage from the data processing hardware to a portable device associated with the patient. The portable device displays the next recommended insulin dosage.

Implementations of the disclosure may include one or more of the following optional features. In some implementations, the method includes transmitting the next recommended insulin dosage to an administration in communication with the data processing hardware. The administration device may include a doser and an administration computing device in communication with the doser. The administration computing device may be configured to cause the doser to administer the next recommended insulin dosage to the patient. In some examples, obtaining the blood glucose data includes one or more of: receiving the blood glucose data from a remote computing device in communication with the data processing hardware during a batch download process; receiving the blood glucose data from the glucometer upon measuring the blood glucose measurement; receiving the blood glucose data from a meter manufacturer computing device in communication with the data processing hardware during the batch download process, the meter manufacturer receiving the blood glucose data from the glucometer; and receiving the blood glucose data from a patient device in communication with the data processing hardware and the glucometer. The remote computing device may execute a download program for downloading the blood glucose data from the glucometer. The patient device may receive the blood glucose data from the glucometer.

In some implementations, applying the set of filters to the blood glucose includes applying an erroneous blood glucose value filter and applying a standard deviation filter. The erroneous blood glucose value filter may be configured to: identify each blood glucose measurement as invalid and unusable when the corresponding blood glucose measurement corresponds to one of a numerical value less than or equal to zero; and identify each blood glucose measurement as valid when the corresponding blood glucose measurement corresponds to a positive integer less than the maximum limit associated with the glucometer. The numerical value may be greater than or equal to a maximum limit associated with the glucometer, or text. The standard deviation filter may be configured to identify each blood glucose measurement identified as valid by the erroneous blood glucose value filter as unusable when the corresponding blood glucose measurement exceeds a threshold value based on a mean of the blood glucose measurements and a standard deviation of the blood glucose measurements.

In some examples, applying the set of filters to the blood glucose measurements includes applying at least one of the following: a bolus-time filter; an ideal mealtime filter; and a whole bucket filter. For instance, the bolus-time filter and the ideal mealtime filter may be applied, or the bolus-time filter and the whole bucket filter may be applied. The bolus-time filter may be configured to identify each blood glucose measurement associated with the at least one scheduled blood glucose time interval as usable when the associated blood glucose time is at or before a meal bolus time associated with the scheduled blood glucose time interval. The ideal mealtime filter may be configured to identify each blood glucose measurement associated with the at least one scheduled blood glucose time interval as usable when at least one of the associated blood glucose time is at or before an end of an ideal mealtime associated with the scheduled blood glucose time interval, or the corresponding blood glucose measurement is less than or equal to an upper limit of a target blood glucose range for the patient. The whole bucket filter may be configured to identify each blood glucose measurement associated with the at least one scheduled blood glucose time interval as usable when the associated blood glucose time is within the time boundary associated with the scheduled blood glucose time interval.

The method may also include receiving, at the data processing hardware, a specified data range from a remote healthcare provider computing device in communication with the data processing hardware. The method may also include aggregating, by the data processing hardware, one or more of the blood glucose measurements associated with a selected time interval to determine a daily aggregate blood glucose measurement for each day within the specified date range. The method may further include aggregating, by the data processing hardware, one or more of the daily aggregate values associated with the selected time interval to determine a representative aggregate blood glucose measurement associated with the selected time interval. One or more of the daily aggregate values associated with the selected time interval may include calculating a minimum number of available daily aggregate values (NdaysBucketMin) by multiplying the total number of days (NdayBucket) within the specified date range by a configurable set point equal (Kndays) to a value between zero and one. The method may also include aggregating the daily aggregate values associated with the lowest values up until the minimum number of available daily aggregate values to determine the representative aggregate blood glucose measurement associated with the selected time interval.

In some examples, the method includes determining, by the data processing hardware, whether the total number of daily aggregate values associated with the selected time interval (# of DayBucket aggregate values for Bucket) is greater than or equal to the minimum number of available daily aggregate values (NdayBucketsMin). The method may also include preventing, by the data processing hardware, adjustments to a previous recommended insulin dosage governed by the selected time interval when the total number of daily aggregate values associated with the selected time interval is less than the minimum number of available daily aggregate values. When the total number of daily aggregate values associated with the selected time interval is greater than or equal to the minimum number of available daily aggregate values, the method may include adjusting, by the data processing hardware, the previous recommended insulin dosage governed by the selected time interval based on the representative aggregate blood glucose measurement associated with the selected time interval.

In some implementations, the method includes selecting, by the data processing hardware, a governing blood glucose measurement as the representative aggregate blood glucose measurement associated with the selected time interval. The method may also include determining, by the data processing hardware, an adjustment factor for adjusting a next recommended meal bolus governed by the selected time interval based on the selected governing blood glucose measurement. The method may further include obtaining, at the data processing hardware, a previous day recommended meal bolus governed by the selected time interval and determining, by the data processing hardware, the next recommended meal bolus by multiplying the adjustment factor times the previous day recommended meal bolus. The selected time interval may include one of a lunch blood glucose time interval, a dinner blood glucose time interval, or a bedtime blood glucose time interval.

In some examples, the method includes aggregating, by the data processing hardware, one or more of the blood glucose measurements associated with a breakfast blood glucose time interval to determine a representative aggregate breakfast blood glucose measurement and aggregating, by the data processing hardware, one or more of the blood glucose measurements associated with a midsleep blood glucose time interval to determine a representative aggregate midsleep blood glucose measurement. The method may also include selecting, by the data processing hardware, a governing blood glucose measurement as a lesser one of the representative aggregate midsleep blood glucose measurement or the representative aggregate breakfast blood glucose measurement and determining, by the data processing hardware, an adjustment factor for adjusting a next recommended basal dosage based on the selected governing blood glucose measurement. The method may further include obtaining, at the data processing hardware, a previous day recommended basal dosage and determining, by the data processing hardware, the next recommended basal dosage by multiplying the adjustment factor times the previous day recommended basal dosage. Each scheduled blood glucose time interval may correlate to an associated blood glucose type including one of a pre-breakfast blood glucose measurement, a pre-lunch blood glucose measurement, a pre-dinner blood glucose measurement, a bedtime blood glucose measurement, and a midsleep blood glucose measurement.

In some examples, the method includes determining, using the data processing hardware, the blood glucose type for each of the blood glucose measurements. The blood glucose type may be tagged by the patient when measuring the blood glucose measurement. The method may include determining, using the data processing hardware, whether the blood glucose time associated with each blood glucose type tagged by the patient is one of within the associated scheduled blood glucose time period or outside the associated scheduled blood glucose time period by an amount not exceeding an acceptable margin. When the blood glucose time associated with the blood glucose type is outside the associated scheduled blood glucose time period by an amount exceeding the acceptable margin, the method may include removing, by the data processing hardware, the blood glucose type tagged by the patient for the associated blood glucose measurement. The representative aggregate blood glucose measurement may include a mean blood glucose value or a medial blood glucose value for the associated scheduled blood glucose time interval.

Another aspect of the disclosure provides a dosing controller including data processing hardware and memory hardware in communication with the data processing hardware. The memory hardware stores instructions for a subcutaneous outpatient program that when executed on the data processing hardware causes the data processing hardware to perform operations. The operations include receiving scheduled blood glucose time intervals for a patient. Each scheduled blood glucose time interval is associated with a corresponding time boundary within a day that does not overlap time boundaries associated with the other scheduled blood glucose time intervals. The operations also include obtaining blood glucose data of the patient from a glucometer in communication with the data processing hardware. The blood glucose data includes blood glucose measurements of the patient, blood glucose times, and insulin dosages previously administered by the patient and associated with the blood glucose measurements. The blood glucose times are each associated with a time of measuring a corresponding blood glucose measurement and. The operations further include applying a set of filters to identify which of the blood glucose measurements associated with at least one of the scheduled blood glucose time intervals are usable and which of the blood glucose measurements associated with the at least one scheduled blood glucose time interval are unusable. The operations also include aggregating the blood glucose measurements associated with the at least one scheduled blood glucose time interval identified as usable by the set of filters to determine a representative aggregate blood glucose measurement associated with the at least one scheduled blood glucose interval. The operations further include determining a next recommended insulin dosage for the patient based on the representative aggregate blood glucose measurement and the insulin dosages previously administered by the patient. The operations also include transmitting the next recommended insulin dosage to a portable device associated with the patient. The portable device displays the next recommended insulin dosage.

This aspect may include one or more of the following optional features. In some implementations, the operations include transmitting the next recommended insulin dosage to an administration device in communication with the dosing controller. The administration device includes a doser and an administration computing device in communication with the doser. The administration computing device may be configured to cause the doser to administer the next recommended insulin dosage to the patient. Obtaining the blood glucose data may include one or more of: receiving the blood glucose data from a remote computing device in communication with the dosing controller during a batch download process; receiving the blood glucose data from the glucometer upon measuring the blood glucose measurement; receiving the blood glucose data from a meter manufacturer computing device in communication with the dosing controller during the batch download process, the meter manufacturer receiving the blood glucose data from the glucometer; and receiving the blood glucose data from a patient device in communication with the dosing controller and the glucometer, the patient device receiving the blood glucose data from the glucometer. The remote computing device may execute a download program for downloading the blood glucose data from the glucometer.

In some examples, applying the set of filters to the blood glucose measurements includes applying an erroneous blood glucose value filter and a standard deviation filter. The erroneous blood glucose value filter may be configured to identify each blood glucose measurement as invalid and unusable when the corresponding blood glucose measurement corresponds to one of a numerical value less than or equal to zero, a numerical value greater than or equal to a maximum limit associated with the glucometer, or text. The erroneous blood glucose value filter may also be configured to identify each blood glucose measurement as valid when the corresponding blood glucose measurement corresponds to a positive integer less than the maximum limit associated with the glucometer. The standard deviation filter is configured to identify each blood glucose measurement identified as valid by the erroneous blood glucose value filter as unusable when the corresponding blood glucose measurement exceeds a threshold value based on a mean of the blood glucose measurements and a standard deviation of the blood glucose measurements.

Applying the set of filters to the blood glucose measurements may include applying at least one of the following: a bolus-time filter; an ideal mealtime filter; and a whole bucket filter. The bolus-time filter may be configured to identify each blood glucose measurement associated with the at least one scheduled blood glucose time interval as usable when the associated blood glucose time is at or before a meal bolus time associated with the scheduled blood glucose time interval. The ideal mealtime filter may be configured to identify each blood glucose measurement associated with the at least one scheduled blood glucose time interval as usable when at least one of the associated blood glucose time is at or before an end of an ideal mealtime associated with the scheduled blood glucose time interval, or the corresponding blood glucose measurement is less than or equal to an upper limit of a target blood glucose range for the patient. The whole bucket filter may be configured to identify each blood glucose measurement associated with the at least one scheduled blood glucose time interval as usable when the associated blood glucose time is within the time boundary associated with the scheduled blood glucose time interval.

In some examples, the operations include receiving a specified date range from a remote healthcare provider computing device in communication with the data processing hardware. The operations may also include aggregating one or more of the blood glucose measurements associated with a selected time interval to determine a daily aggregate blood glucose measurement for each day within the specified date range and aggregating one or more of the daily aggregate values associated with the selected time interval to determine a representative aggregate blood glucose measurement associated with the selected time interval. In some configurations, the aggregating the one or more of the daily aggregate values associated with the selected time interval includes calculating a minimum number of available daily aggregate values (NdayBucketsMin) and aggregating the daily aggregate values associated with the lowest values up until the minimum number of available daily aggregate values to determine the representative aggregate blood glucose measurement. In these configurations, the minimum number of available daily aggregate values (NdayBucketsMin) is calculated by multiplying the total number of days within the specified date range (NdayBucket) by a configurable set point (Kndays) equal to a value between zero and one. For instance, Kndays may be equal to 0.5. In some implementations, the operations include determining whether the total number of daily aggregate values associated with the selected time interval is greater than or equal to the minimum number of available daily aggregate values. The operations may also include preventing adjustments to a previous recommended insulin dosage governed by the selected time interval when the total number of daily aggregate values associated with the selected time interval is less than the minimum number of available daily aggregate values.

When the total number of daily aggregate values associated with the selected time interval is greater than or equal to the minimum number of available daily aggregate values, the method may include adjusting the previous recommended insulin dosage governed by the selected time interval based on the representative aggregate blood glucose measurement associated with the selected time interval. In some examples, the operations include selecting a governing blood glucose measurement as the representative aggregate blood glucose measurement associated with the selected time interval and determining an adjustment factor for adjusting a next recommended meal bolus governed by the selected time interval based on the selected governing blood glucose measurement. The operations may also include obtaining a previous day recommended meal bolus governed by the selected time interval and determining the next recommended meal bolus by multiplying the adjustment factor times the previous day recommended meal bolus. The selected time interval may include one of a lunch blood glucose time interval, a dinner blood glucose time interval, or a bedtime blood glucose time interval.

In some implementations, the operations include selecting a governing blood glucose measurement as the representative aggregate blood glucose measurement associated with the selected time interval and determining an adjustment factor for adjusting a next recommended carbohydrate-to-insulin ratio governed by the selected time interval based on the selected governing blood glucose measurement. The operations may also include obtaining a previous day recommended carbohydrate-to-insulin ratio governed by the selected time interval and determining the next recommended carbohydrate-to-insulin ratio by multiplying the adjustment factor times the previous day recommended meal bolus. The selected time interval may include one of a lunch blood glucose time interval, a dinner blood glucose time interval, or a bedtime blood glucose time interval. In some examples, the operations include aggregating one or more of the blood glucose measurements associated with a breakfast blood glucose time interval to determine a representative aggregate breakfast blood glucose measurement and aggregating one or more of the blood glucose measurements associated with a midsleep blood glucose time interval to determine a representative aggregate midsleep blood glucose measurement. The operations may further include selecting a governing blood glucose measurement as a lesser one of the representative aggregate midsleep blood glucose measurement or the representative aggregate breakfast blood glucose measurement and determining an adjustment factor for adjusting a next recommended basal dosage based on the selected governing blood glucose measurement. In some examples, the operations include obtaining a previous day recommended basal dosage and determining the next recommended basal dosage by multiplying the adjustment factor times the previous day recommended basal dosage.

In some implementations, each scheduled blood glucose time interval correlates to an associated blood glucose type including one of a pre-breakfast blood glucose measurement, a pre-lunch blood glucose measurement, a pre-dinner blood glucose measurement, a bedtime blood glucose measurement and a midsleep blood glucose measurement. In some examples, the operations include determining the blood glucose type for each of the blood glucose measurements and determining whether the blood glucose time associated with each blood glucose type tagged by the patient is one of within the associated scheduled blood glucose time period or outside the associated scheduled blood glucose time period by an amount not exceeding an acceptable margin. The blood glucose type may be tagged by the patient when measuring the blood glucose measurement. When the blood glucose time associated with the blood glucose type is outside the associated scheduled blood glucose time period for an amount exceeding the acceptable margin, the operations may include removing the blood glucose type tagged by the patient for the associated blood glucose measurement. The representative aggregate blood glucose measurement may include a mean blood glucose value or a medial blood glucose value for the associated scheduled blood glucose time interval.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2C-2F are schematic views of an example display for inputting SubQ information relating to the patient.

FIG. 2G is a schematic view of an example input screen for inputting configurable constants.

FIG. 2I is a schematic view of an example input screen for inputting blood glucose update intervals.

FIG. 2J is a schematic view of an example input screen for inputting options for filtering and aggregating blood glucose measurements.

FIG. 3 is a schematic view of an example correction boluses process.

FIGS. 7A-7C are schematic views of an example blood glucose aggregation process for time intervals when a patient is not consuming meals.

FIGS. 7D-7F are schematic views of an example blood glucose aggregation process for time intervals when a patient is consuming meals.

FIGS. 16A-16F are schematic views of example filters of the blood glucose filtering process of FIG. 15 for filtering out past blood glucose data.

FIG. 17A is a schematic view of an example blood glucose aggregation process for determining a bucket aggregate value for an associated time-bucket.

Like reference symbols in the various drawings indicate like elements.

DETAILED DESCRIPTION

Diabetic outpatients must manage their blood glucose level within desired ranges by using insulin therapy that includes injection dosages of insulin corresponding to meal boluses and basal dosages. Meal boluses without meals cause hypoglycemia; meals without meal boluses cause hyperglycemia. Different providers may use different methods of adjusting doses: some may use formulas of their own; some may use paper protocols that are complex and difficult for the outpatient to follow, leading to a high incidence of human error; and some may use heuristic methods. Therefore, it is desirable to have a clinical support system 100 (FIGS. 1A and 1B) that monitors outpatients' blood glucose level.

Figure 1A:
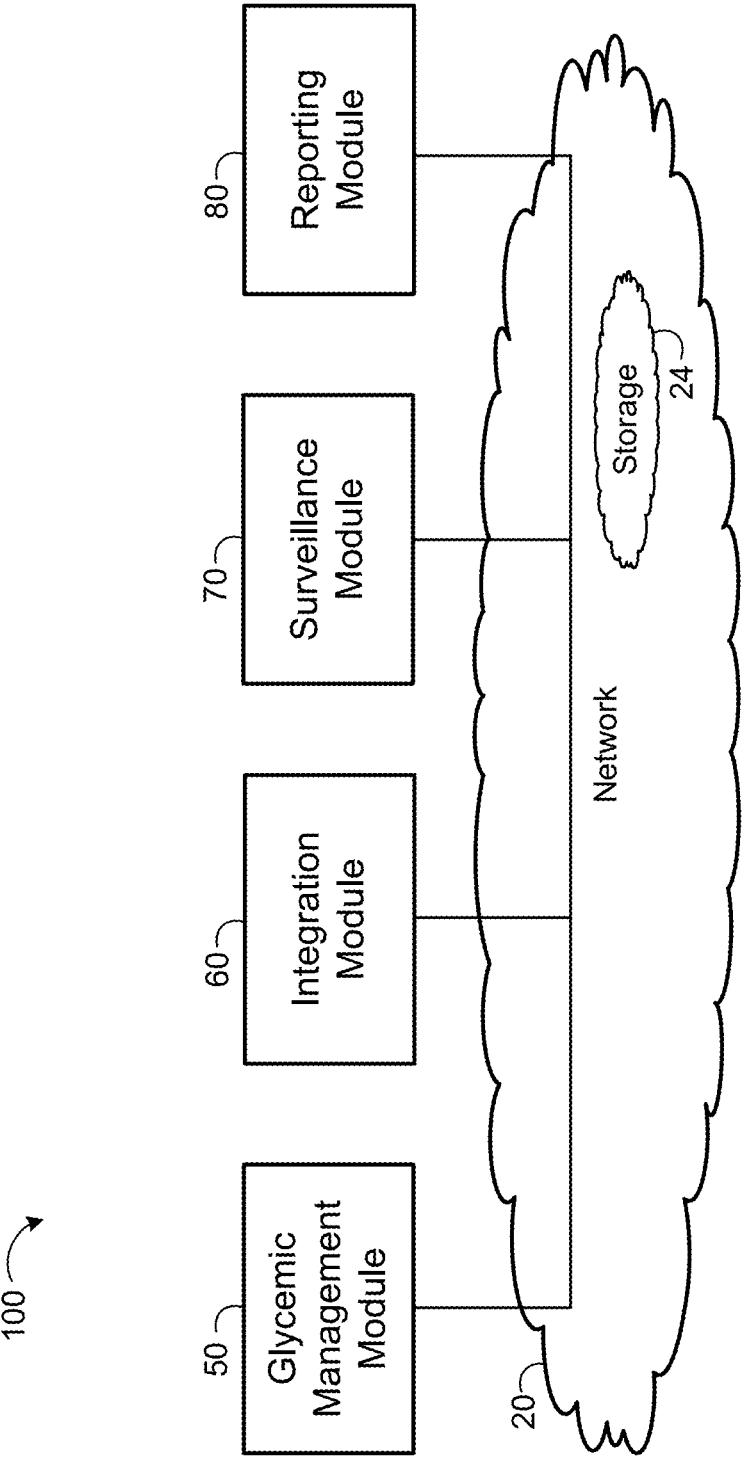
FIG. 1A is a schematic view of an example system for monitoring blood glucose level of a patient.

Referring to FIGS. 1A and 1*i*, in some implementations, a clinical decision support system 100 analyzes inputted patient condition parameters for an outpatient 10 and calculates a personalized dose of insulin to bring and maintain the patient's blood glucose level into a target range $BG_{TR}$. As used herein, the patient 10 refers to an outpatient that may be located at some remote location, such as the patient's 10 residence or place of employment. As used herein, the term "clinical" may refer to a hospital call center. Moreover, the system 100 monitors the glucose levels of a patient 10 and calculates a recommended subcutaneous insulin dose to bring the patient's blood glucose into the preferred target range $BG_{TR}$ over a recommended period of time. A qualified and trained healthcare professional 40 may use the system 100 along with clinical reasoning to determine the proper dosing administered to a patient 10. Therefore, the system 100 is a glycemic management tool for evaluation a patient's current and cumulative blood glucose value BG while taking into consideration the patient's information such as age, weight, and height. The system 100 may also consider other information such as carbohydrate content of meals, insulin doses being administered to the patient 10, e.g., long-acting insulin doses for basal insulin and rapid-acting insulin doses for meal boluses and correction boluses. Based on those measurements (that may be stored in non-transitory memory 24, 114, 144), the system 100 recommends a subcutaneous basal and bolus insulin dosing recommendation or prescribed dose to adjust and maintain the blood glucose level towards a configurable (based on the patient's information) physician's determined blood glucose target range $BG_{TR}$. The system 100 also considers a patient's insulin sensitivity or improved glycemic management and outcomes. The system 100 may take into account pertinent patient information such as demographics and previous results, leading to a more efficient use of healthcare resources. Finally, the system 100 provides a reporting platform for reporting the recommendations or prescribed dose(s) to the user 40 and the patient 10. In addition, the system 100 provides faster, more reliable, and more efficient insulin administration than a human monitoring the insulin administration. The system 100 reduces the probability of human error and insures consistent treatment, due to the system's capability of storing and tracking the patient's blood glucose levels BG, which may be used for statistical studies. The system 100 provides a meal-by-meal adjustment of Meal Boluses without carbohydrate counting, by providing a dedicated subprogram that adjusts meal boluses based on the immediately preceding meal bolus and the BG that followed it. The system 100 provides a meal-by-meal adjustment of Meal Boluses with carbohydrate counting by providing a dedicated subprogram that adjusts meal boluses based a Carbohydrate-to-Insulin Ratio (CTR) that is adjusted at each meal, based on the CIR used at the immediately preceding meal bolus and the BG that followed it.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's blood glucose level is below a preferred target. Appropriate management of blood glucose levels for critically ill patients reduces co-morbidities and is associated with a decrease in infection rates, length of hospital stay, and death. The treatment of hyperglycemia may differ depending on whether or not a patient has been diagnosed with Type 1 diabetes mellitus, Type 2 diabetes mellitus, gestational diabetes mellitus, or non-diabetic stress hyperglycemia. The blood glucose target range $BG_{TR}$ is defined by a lower limit, i.e., a low target $BG_{TRL}$ and an upper limit, i.e., a high target $BG_{TRH}$.

Diabetes Mellitus has been treated for many years with insulin. Some recurring terms and phrases are described below:

Injection: Administering insulin by means of manual syringe or an insulin "pen," with a portable syringe named for its resemblance to the familiar writing implement.

Infusion: Administering insulin in a continuous manner by means of an insulin pump for subcutaneous insulin apparatus 123*a* capable of continuous administration.

Basal-Bolus Therapy: Basal-bolus therapy is a term that collectively refers to any insulin regimen involving basal insulin and boluses of insulin.

Basal Insulin: Insulin that is intended to metabolize the glucose released by a patient's the liver during a fasting state. Basal insulin is administered in such a way that it maintains a background level of insulin in the patient's blood, which is generally steady but may be varied in a programmed manner by an insulin pump 123*a*. Basal insulin is a slow, relatively continuous supply of insulin throughout the day and night that provides the low, but present, insulin concentration necessary to balance glucose consumption (glucose uptake and oxidation) and glucose production (glucogenolysis and gluconeogenesis). A patient's Basal insulin needs are usually about 10 to 15 mU/kg/hr and account for 30% to 50% of the total daily insulin needs; however, considerable variation occurs based on the patient 10.

Bolus Insulin: Insulin that is administered in discrete doses. There are two main types of boluses, Meal Bolus and Correction Bolus.

Meal Bolus: Taken just before a meal in an amount which is proportional to the anticipated immediate effect of carbohydrates in the meal entering the blood directly from the digestive system. The amounts of the Meal Boluses may be determined and prescribed by a physician 40 for each meal during the day, i.e., breakfast, lunch, and dinner. Alternatively, the Meal Bolus may be calculated in an amount generally proportional to the number of grams of carbohydrates in the meal. The amount of the Meal Bolus is calculated using a proportionality constant, which is a personalized number called the Carbohydrate-to-Insulin Ratio (CIR) and calculated as follows:

$$\text{Meal Insulin Bolus} = \{\text{grams of carbohydrates in the meal}\}/\text{CIR} \tag{1}$$

Correction Bolus CB: Injected immediately after a blood glucose measurement; the amount of the correction bolus is proportional to the error in the BG (i.e., the bolus is proportional to the difference between the blood glucose measurement BG and the patient's personalized Target blood glucose $BG_{Target}$). The proportionality constant is a personalized number called the Correction Factor, CF. The Correction Bolus is calculated as follows:

$$CB = (BG - BG_{Target})/CF \tag{2}$$

A Correction Bolus CB is generally administered in a fasting state, after the previously consumed meal has been digested. This often coincides with the time just before the next meal.

In some implementations, blood glucose measurements BG are aggregated using an exponentially-weighted moving average $EMA_t$ as a function for each modal day's time interval BG. The EMAt is calculated as follows:

$$EMA_t = \alpha(BG_t) + (1-\alpha)EMA_{t-1}, \tag{3}$$

wherein:

$$\alpha = 2/(n+1),$$

wherein n is the number of equivalent days averaged. In other embodiments, an arithmetic moving average is utilized that calculates the sum of all BG values in n days divided by a total count (n) of all values associated with the arithmetic average.

There are several kinds of Basal-Bolus insulin therapy including Insulin Pump therapy and Multiple Dose Injection therapy:

Insulin Pump Therapy: An insulin pump 123*a* is a medical device used for the administration of insulin in the treatment of diabetes mellitus, also known as continuous subcutaneous insulin infusion therapy. The device includes: a pump, a disposable reservoir for insulin, and a disposable infusion set. The pump 123*a* is an alternative to multiple daily injections of insulin by insulin syringe or an insulin pen and allows for intensive insulin therapy when used in conjunction with blood glucose monitoring and carbohydrate counting. The insulin pump 123*a* is a battery-powered device about the size of a pager. It contains a cartridge of insulin, and it pumps the insulin into the patient via an "infusion set", which is a small plastic needle or "canula" fitted with an adhesive patch. Only rapid-acting insulin is used.

Multiple Dose Injection (MDI): MDI involves the subcutaneous manual injection of insulin several times per day using syringes or insulin pens 123*b*. Meal insulin is supplied by injection of rapid-acting insulin before each meal in an amount proportional to the meal. Basal insulin is provided as a once, twice, or three time daily injection of a dose of long-acting insulin. Other dosage frequencies may be available. Advances continue to be made in developing different types of insulin, many of which are used to great advantage with MDI regimens:

Long-acting insulins are non-peaking and can be injected as infrequently as once per day. These insulins are widely used for Basal Insulin. They are administered in dosages that make them appropriate for the fasting state of the patient, in which the blood glucose is replenished by the liver to maintain a steady minimum blood glucose level.

Rapid-acting insulins act on a time scale shorter than natural insulin. They are appropriate for boluses.

The decision support system 100 includes a glycemic management module 50, an integration module 60, a surveillance module 70, and a reporting module 80. Each module 50, 60, 70, 80 is in communication with the other modules 50, 60, 70, 80 via a network 20. In some examples, the network 20 (discussed below) provides access to cloud computing resources that allows for the performance of services on remote devices instead of the specific modules 50, 60, 70, 80. The glycemic management module 50 executes a program 200 (e.g., an executable instruction set) on a processor 112, 132, 142 or on the cloud computing resources. The integration module 60 allows for the interaction of users 40 and patients 10 with the system 100. The integration module 60 receives information inputted by a user 40 and allows the user 40 to retrieve previously inputted information stored on a storage system (e.g., one or more of cloud storage resources 24, a non-transitory memory 144 of an electronic medical system 140 of a clinic 42 or hospital call center (e.g., Telemedicine facility), a non-transitory memory 114 of the patient device 110, a non-transitory memory 134 of the service provider's system 130, or other non-transitory storage media in communication with the integration module 60). Therefore, the integration module 60 allows for the interaction between the users 40, patients 10, and the system 100 via a display 116, 146. The surveillance module 70 considers patient information 208*a* received from a user 40 via the integration module 60 and information received from a glucometer 124 that measures a patient's blood glucose value BG and determines if the patient 10 is within a threshold blood glucose value $BG_{TH}$. In some examples, the surveillance module 70 alerts the user 40 if a patient's blood glucose values BG are not within a threshold blood glucose value $BG_{TH}$. The surveillance module 70 may be preconfigured to alert the user 40 of other discrepancies between expected values and actual values based on pre-configured parameters (discussed below). For example, when a patient's blood glucose value BG drops below a lower limit of the threshold blood glucose value $BG_{THL}$. The reporting module 80 may be in communication with at least one display 116, 146 and provides information to the user 40 determined using the glycemic management module 50, the integration module 60, and/or the surveillance module 70. In some examples, the reporting module 80 provides a report that may be displayed on a display 116, 146 and/or is capable of being printed.

The system 100 is configured to evaluate a glucose level and nutritional intake of a patient 10. Based on the evaluation and analysis of the data, the system 100 calculates an insulin dose, which is administered to the patient 10 to bring and maintain the blood glucose level of the patient 10 into the blood glucose target range $BG_{TR}$. The system 100 may be applied to various devices, including, but not limited to, subcutaneous insulin infusion pumps 123a, insulin pens 123b, glucometers 124, continuous glucose monitoring systems, and glucose sensors.

In some examples the clinical decision support system 100 includes a network 20, a patient device 110, a dosing controller 160, a service provider 130, and a meter manufacturer provider 190. The patient device 110 may include, but is not limited to, desktop computers 110a or portable electronic device 110b (e.g., cellular phone, smartphone, personal digital assistant, barcode reader, personal computer, or a wireless pad) or any other electronic device capable of sending and receiving information via the network 20. In some implementations, one or more of the patient's glucometer 124, insulin pump 123a, or insulin pen 123b are capable of sending and receiving information via the network 20.

The patient device 110a, 110b includes a data processor 112a, 112b (e.g., a computing device that executes instructions), and non-transitory memory 114a, 114b and a display 116a, 116b (e.g., touch display or non-touch display) in communication with the data processor 112. In some examples, the patient device 110 includes a keyboard 118, speakers 122, microphones, mouse, and a camera.

The glucometer 124, insulin pump 123a, and insulin pen 123b associated with the patient 10 include a data processor 112c, 112d, 112e (e.g., a computing device that executes instructions), and non-transitory memory 114c, 114d, 114e and a display 116c, 116d, 116e (e.g., touch display or non-touch display in communication with the data processor 112c, 112d, 112e.

The meter manufacturer provider 190 may include may include a data processor 192 in communication with non-transitory memory 194. The data processor 192 may execute a proprietary download program 196 for downloading blood glucose BG data from the memory 114c of the patient's glucometer 124. In some implementations, the proprietary download program 196 is implemented on the health care provider's 140 computing device 142 or the patient's 10 device 110a for downloading the BG data from memory 114c. In some examples, the download program 196 exports a BG data file for storage in the non-transitory memory 24, 114, 144. The data processor 192 may further execute a web-based application 198 for receiving and formatting BG data transmitted from one or more of the patient's devices 110a, 110b, 124, 123a, 123b and storing the BG data in non-transitory memory 24, 114, 144.

The service provider 130 may include a data processor 132 in communication with non-transitory memory 134. The service provider 130 provides the patient 10 with a program 200 (see FIG. 2) (e.g., a mobile application, a web-site application, or a downloadable program that includes a set of instructions) executable on a processor 112, 132, 142 of the dosing controller 160 and accessible through the network 20 via the patient device 110, health care provider electronic medical record systems 140, portable blood glucose measurement devices 124 (e.g., glucose meter or glucometer), or portable administration devices 123a, 123b.

Figure 2A:
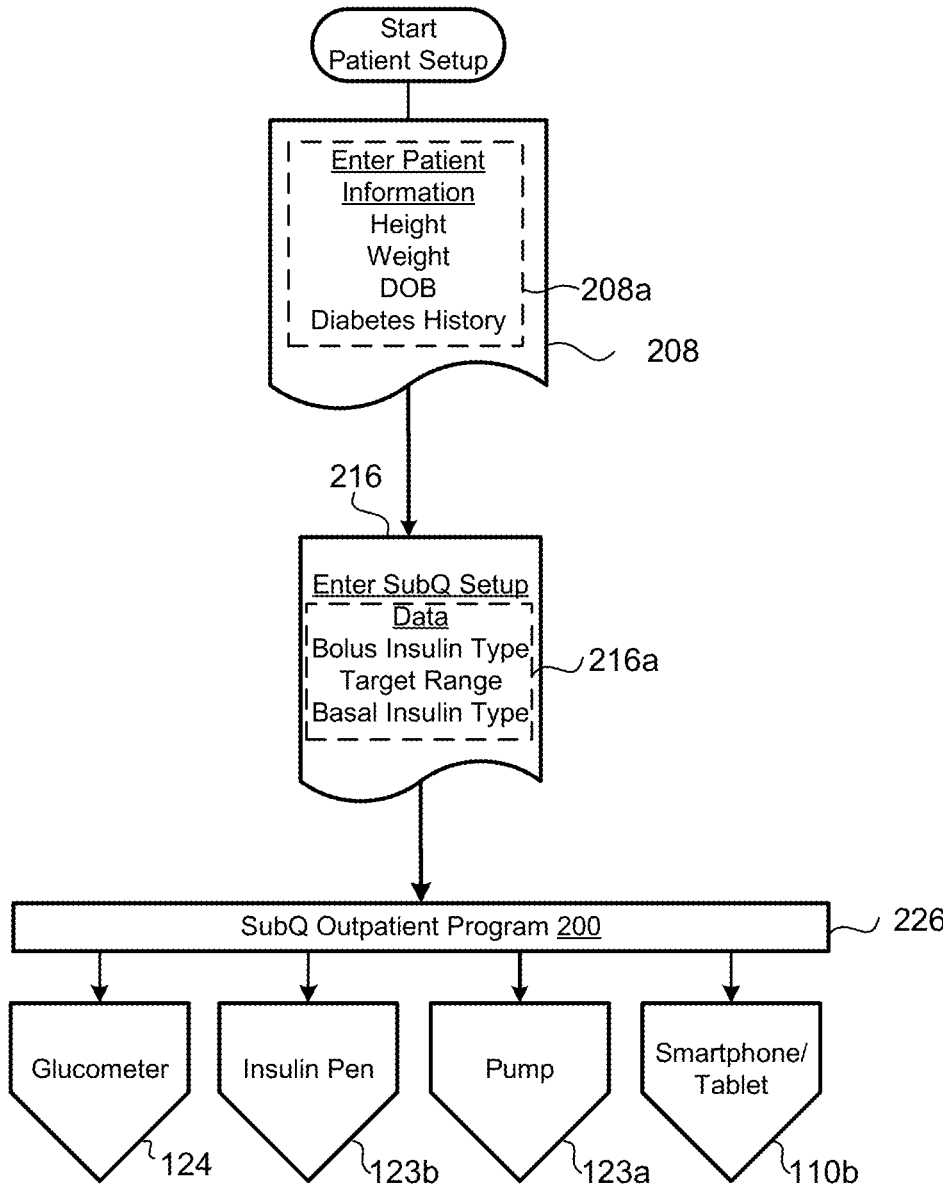
FIG. 2A is a schematic view of an example program for monitoring the blood glucose level of a patient.
Figure 2B:
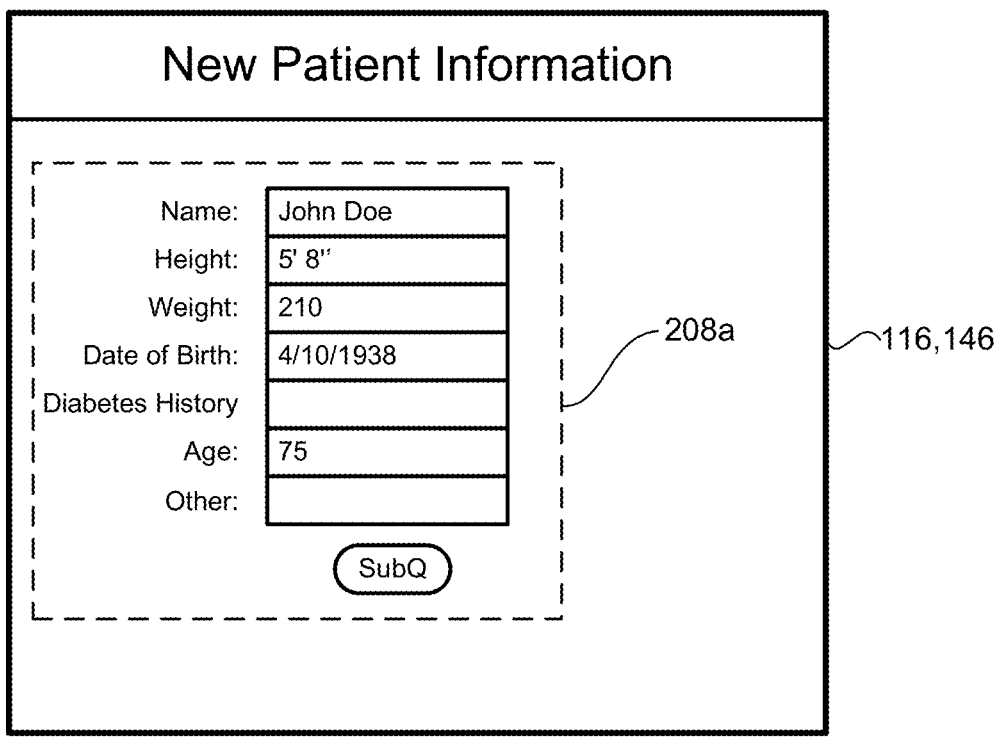
FIG. 2B is a schematic view of an example display for inputting patient information.

In some implementations, a health care provider medical record system 140 is located at a doctor's office, clinic 42, or a facility administered by a hospital (such as a hospital call center (HCP)) and includes a data processor 142, a non-transitory memory 144, and a display 146 (e.g., touch display or non-touch display). The non-transitory memory 144 and the display 146 are in communication with the data processor 142. In some examples, the health care provider electronic medical system 140 includes a keyboard 148 in communication with the data processor 142 to allow a user 40 to input data, such as patient information 208a (FIGS. 2A and 2B). The non-transitory memory 144 maintains patient records capable of being retrieved, viewed, and, in some examples, modified and updated by authorized hospital personal on the display 146.

The dosing controller 160 is in communication with the glucometer 124, insulin administration device 123a, 123b and includes a computing device 112, 132, 142 and non-transitory memory 114, 134, 144 in communication with the computing device 112, 132, 142. The dosing controller 160 executes the program 200. The dosing controller 160 stores patient related information retrieved from the glucometer 124 to determine insulin doses and dosing parameters based on the received blood glucose measurement BG.

Figure 1B:
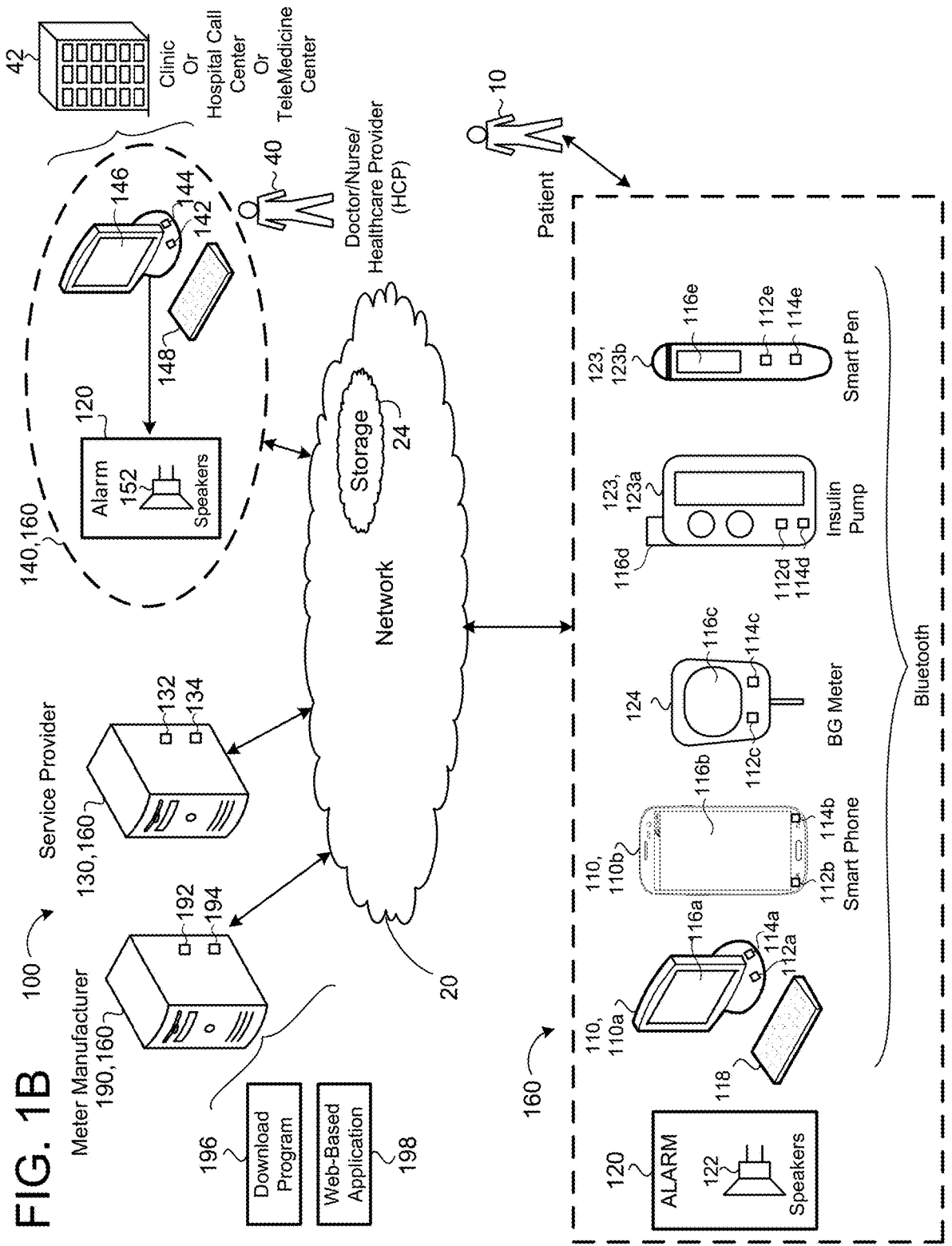
FIG. 1B is a schematic view of an example system for monitoring blood glucose level of a patient.
Figure 1C:
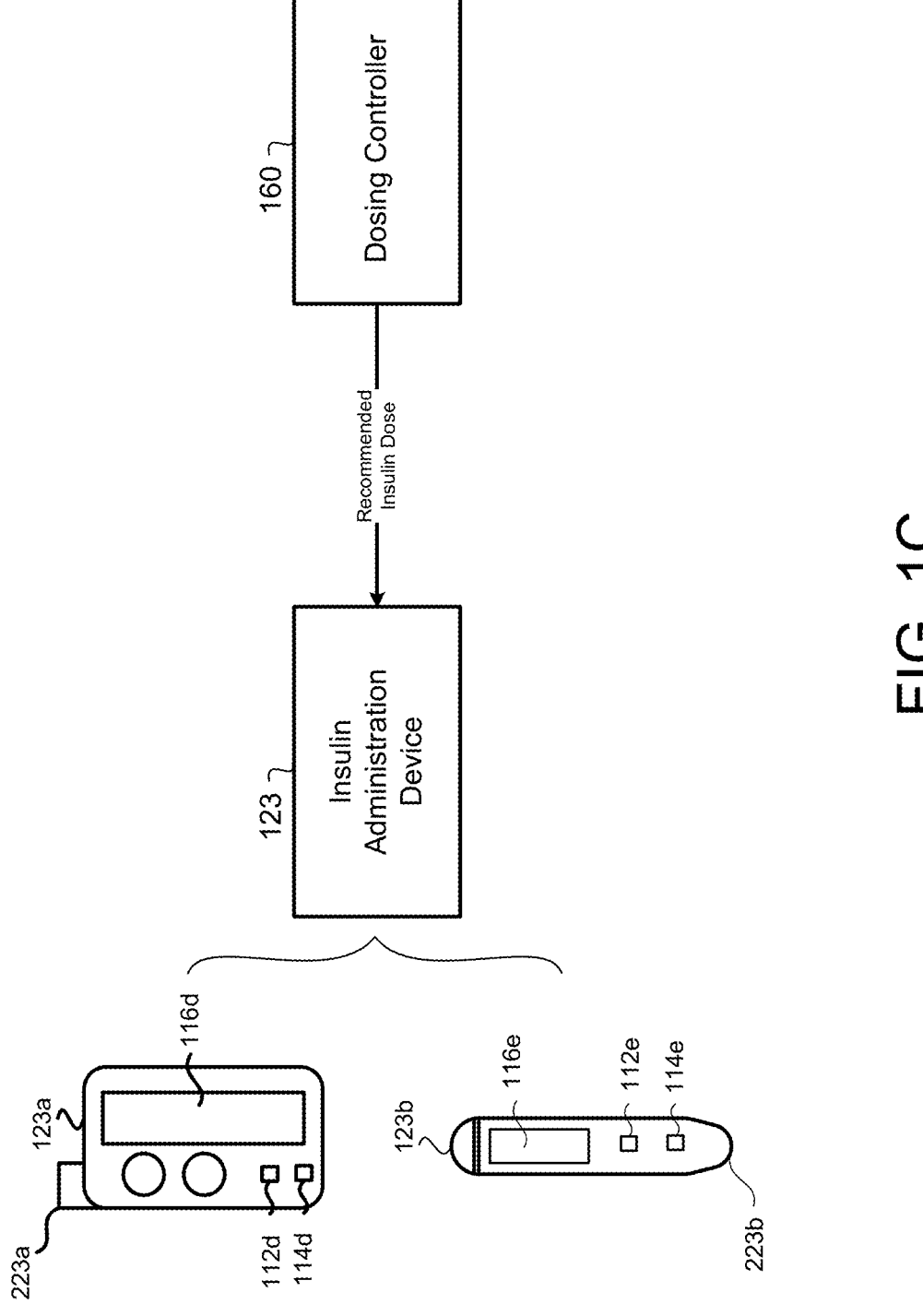
FIG. 1C is a schematic view of an example administration device in communication with a dosing controller.

Referring to FIG. 1C, in some implementations, the insulin device 123 (e.g., administration device), in communication with the dosing controller 160, capable of executing instructions for administering insulin according to a subcutaneous insulin treatment program selected by the dosing controller 160. The administration device 123 may include the insulin pump 123a or the pen 123b. The administration device 123 is in communication with the glucometer 124 and includes a computing device 112d, 112e and non-transitory memory 114d, 114e in communication with the computing device 112d, 112e. The administration device 123 includes a doser 223a, 223b in communication with the administration computing device 112d, 112e for administering insulin to the patient. For instance, the doser 223a of the insulin pump 123a includes an infusion set including a tube in fluid communication with an insulin reservoir and a cannula inserted into the patient's 10 body and secured via an adhesive patch. The doser 223b of the pen 123b includes a needle for insertion into the patients 10 for administering insulin from an insulin cartridge. The administration device 123 may receive a subcutaneous insulin treatment program selected by and transmitted from the dosing controller 160, while the administration computing device 112d, 112e may execute the subcutaneous insulin treatment program. By transmitting the insulin treatment program to the administration device 123 from the dosing controller 160, the administration computing device 112d, 112e need not be pre-programmed to execute various insulin treatment programs stored within memory 114d, 114e, thereby reducing memory usage while increasing processing speeds thereof. Executing the subcutaneous insulin treatment program by the administration computing device 112d, 112e causes the doser 223a, 223b to administer doses of insulin specified by the subcutaneous insulin treatment program. For instance, units for the doses of insulin may be automatically set or dialed in by the administration device 123a, 123b and administered via the doser 223a, 223b to the patient 10. Accordingly, the administration devices 123a, 123b may be "smart" administration devices capable of communicating with the dosing controller 160 to populate recommended doses of insulin for administering to the patient 10. In some examples, the administration devices 123a, 123b may execute the dosing controller 160 on the administration computing devices 112d, 112e to calculate the recommended doses of insulin for administering to the patient 10.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

Referring to FIGS. 1B and 2A-2F, the program 200 receives parameters (e.g., patient condition parameters) inputted via the client device 110, the service provider 130, and/or the clinic system 140, analyzes the inputted parameters, and determines a personalized dose of insulin to bring and maintain a patient's blood glucose level BG into a preferred target range $BG_{TR}$ for a SubQ outpatient program 200 (FIG. 2A).

In some implementations, before the program 200 begins to receive the parameters, the program 200 may receive a username and a password (e.g., at a login screen displayed on the display 116, 146) to verify that a qualified and trained healthcare professional 40 is initiating the program 200 and entering the correct information that the program 200 needs to accurately administer insulin to the patient 10. The system 100 may customize the login screen to allow a user 40 to reset their password and/or username. Moreover, the system 100 may provide a logout button (not shown) that allows the user 40 to log out of the system 100. The logout button may be displayed on the display 116, 146 at any time during the execution of the program 200.

The decision support system 100 may include an alarm system 120 that alerts a user 40 at the clinic 42 (or hospital call center) when the patient's blood glucose level BG is outside the target range $BG_{TR}$. The alarm system 120 may produce an audible sound via speaker 122 in the form of a beep or some like audio sounding mechanism. For instance, the alarm system 120 may produce an audible sound via a speaker 122 of the mobile device 110b. In some examples, the alarm system 120 displays a warning message or other type of indication on the display 116a-e of the patient device 110 to provide a warning message. The alarm system 120 may also send the audible and/or visual notification via the network 20 to the clinic system 140 (or any other remote station) for display on the display 146 of the clinic system 140 or played through speakers 152 of the clinic system 140.

For commencing a SubQ outpatient process 1800 (FIGS. 5A and 5B), the program 200 prompts a user 40 to input patient information 208a at block 208. The user 40 may input the patient information 208a, for example, via the user device 140 or via the health care provider medical record systems 140 located at a clinic 42 (or a doctor's office or HCP). The user 40 may input new patient information 208a as shown in FIG. 2B. The program 200 may retrieve the patient information 208a from the non-transitory memory 144 of the clinic's electronic medical system 140 or the non-transitory memory 114 of the patient device 110 (e.g., where the patient information 208a was previously entered and stored). The patient information 208a may include, but is not limited to, a patient's name, a patient's identification number (ID), a patient's height, weight, date of birth, diabetes history, physician name, emergency contact, hospital unit, diagnosis, gender, room number, and any other relevant information.

Referring to FIGS. 2A and 2C-2F, the program 200 at block 216 further requests the user 40 to enter SubQ information 216a for the patient 10, such as patient diabetes status, subcutaneous Orderset Type ordered for the patient 10 (e.g., "Fixed Carbs/meal" that is intended for patients on a consistent carbohydrate diet, total daily dosage (TDD), bolus insulin type (e.g., Novolog), basil insulin type (e.g., Lantus) and frequency of distribution (e.g., 1 dose per day, 2 doses per day, 3 doses per day, etc.), basil time, basal percentage of TDD, meal bolus percentage of TDD, daily meal bolus distribution (e.g., breakfast bolus, lunch bolus and dinner bolus), or any other relevant information. In some implementations, TDD is calculated following a period on Intravenous Insulin in accordance with equation:

$$TDD = QuickTransitionConstant*M_{Trans} \qquad (4A)$$

where QuickTransitionConstant is usually equal to 1000, and $M_{Trans}$ is the patient's multiplier at the time of initiation of the SubQ transition process. In other implementations, the TDD is calculated by a statistical correlation of TDD as a function of body weight. The following equation is the correlation used:

$$TDD = 0.5*Weight(kg) \qquad (4B)$$

In other implementations, the patient's total daily dose TDD is calculated in accordance with the following equation:

$$TDD = (BG_{Target} - K)*(M_{Trans})*24 \qquad (4C)$$

where $M_{Trans}$ is the patient's multiplier at the time of initiation of the SubQ transition process.

Figure 2D:
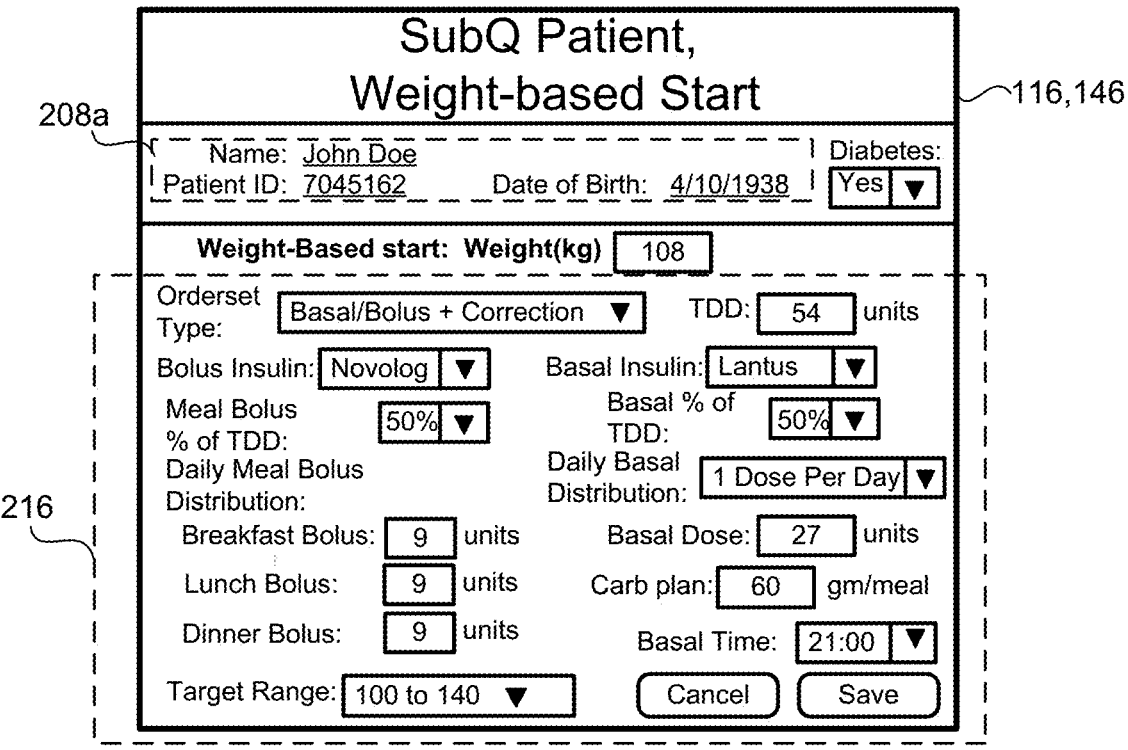
Figure 2E:
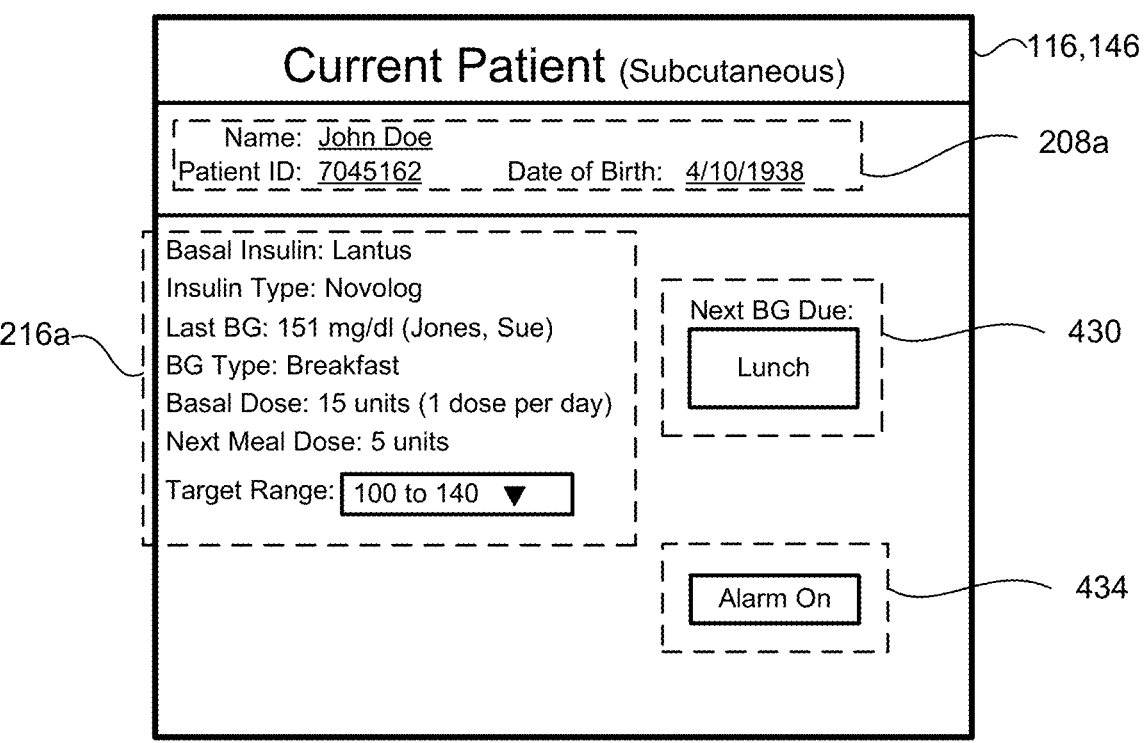
Figure 10:
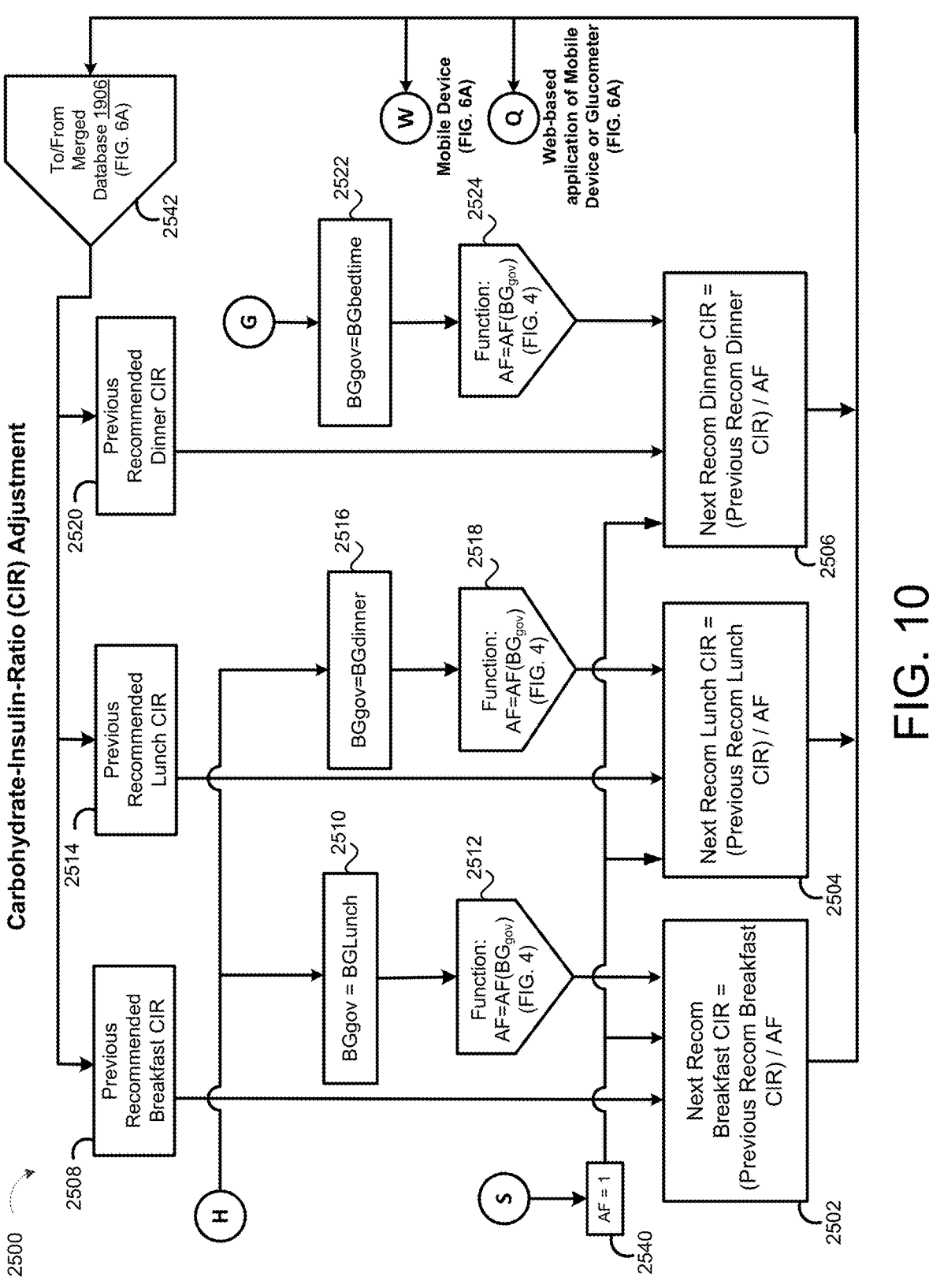
FIG. 10 is a schematic view of an example carbohydrate-insulin-ratio adjustment process.
Figure 13:
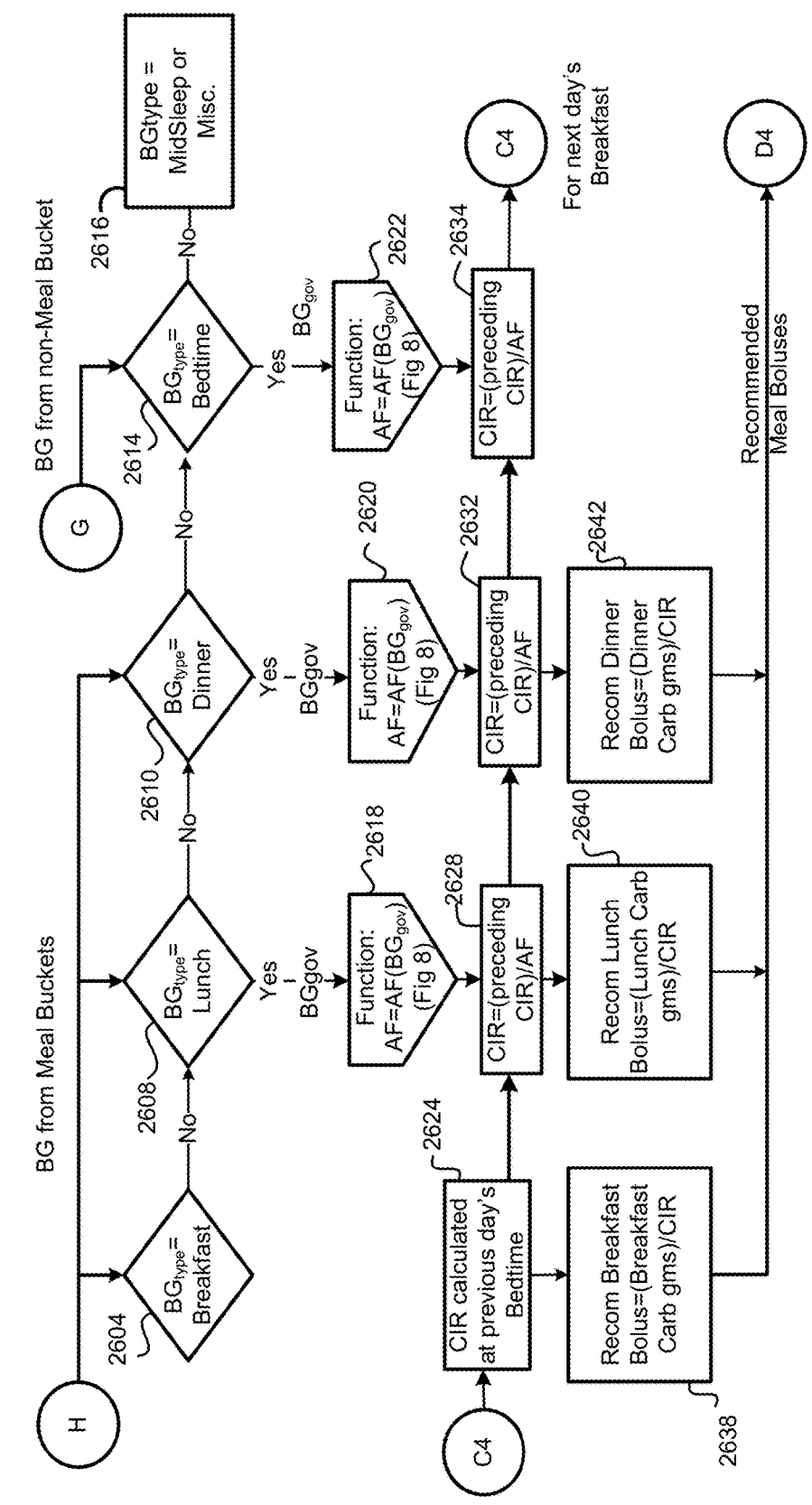
FIG. 13 is a schematic view of an example carbohydrate-insulin-ratio adjustment process on a meal-by-meal basis.

In some implementations, the patient SubQ information 216a is prepopulated with default parameters, which may be adjusted or modified. In some examples, portions of the patient SubQ information 216 are prepopulated with previously entered patient subcutaneous information 216a. The program 200 may prompt the request to the user 40 to enter the SubQ information 216a on the display 116 of the patient device 110. In some implementations, the subcutaneous insulin process 1800 prompts the request on the display 116 for a custom start of new SubQ patients (FIG. 2C) being treated with the SubQ outpatient process 1800. In some examples, the program 200 prompts the request on the display 116 for a weight-based start of SubQ patients being treated with the SubQ outpatient process 1800 as shown in FIG. 2D. For instance, the user 40 may input the weight (e.g., 108 kg) of the patient 10, and in some examples, the TDD is calculated using EQ. 4B based on the patient's weight. As shown in FIG. 2E, the user 40 may further enter a schedule for when blood glucose BG measurements are required 430 (e.g., Next BG Due: Lunch) for the patient 10 and whether or not an alarm 434 is to be activated. For instance, if a BG measurement is below a threshold value, or if the patient has not submitted a BG measurement during Lunch, the alarm system 120 may generate a warning sound via speakers 122 to alert the patient 10 that a BG measurement is required. The alarm may sound on one or more of the patient's portable devices 110a, 110b, 124, 123a, 123b. As shown in FIG. 2F, the patient 10 may enter a number of carbohydrates for the upcoming meal (e.g., 60) such that adjustment of Meal Boluses with carbohydrate counting can be calculated by EQ. 1 based upon the Carbohydrate-to-Insulin Ratio (CIR). In some implementations, the CIR is associated with the BGtype or Bucket, and adjusted on a daily basis by process 2500 (FIG. 10). In other implementations, the CIR is adjusted at each meal, based on the CIR used at the immediately preceding meal bolus and the BG measurement occurring after that meal bolus by process 2600 (FIG. 13).

The program 200 flows to block 216, where the user 40 enters patient subcutaneous information 216a, such as bolus insulin type, target range, basal insulin type and frequency of distribution (e.g., 1 dose per day, 2 doses per day, 3 doses per day, etc.), patient diabetes status, subcutaneous type ordered for the patient (e.g., Basal/Bolus and correction that is intended for patients on a consistent carbohydrate diet, frequency of patient blood glucose measurements, or any other relevant information. In some implementations, the patient subcutaneous information 216a is prepopulated with default parameters, which may be adjusted or modified. When the user 40 enters the patient subcutaneous information 216a, the user selects the program 200 to execute the SubQ outpatient process 1800 at block 226.

In some implementations, the user 40 selects to initiate a subcutaneous outpatient program 200 (FIG. 2A) executing on the dosing controller 160 to provide recommended insulin dosing (bolus/basal) for a patient 10 equipped with one or more portable devices 110a, 110b, 124, 123a, 123b. The user 40 may configure the subcutaneous outpatient program 200 by selecting the portable devices used by the patient 10. Selection of block 124 indicates information for the patient's glucometer 124, including communication capabilities with other devices and/or the network 20. Selection of block 123b indicates that the patient 10 uses an insulin pen 123b for administering insulin. Information for the pen 123b may be provided that includes communication capabilities with other devices and/or the network 20. In some examples, the pen 123b is a "smart" that may include an administration computing device 112e in communication with the dosing controller 160 for administering insulin to the patient 10. Selection of block 123a indicates that the patient 10 uses an insulin pump 123a for administering insulin. Information for the pump 123a may be provided that includes communication capabilities with other devices and/or the network 20. In some examples, the pen 123b is a "smart" pen that may include the administration computing device 112d in communication with the dosing controller 160 for administering insulin to the patient 10. Selection of block 110b indicates information for the patient's 10 smartphone 110b or tablet, including communication capabilities with the glucometer 124 and/or the insulin administration devices 123a, 123b, For instance, the smartphone 110b may communicate with the glucometer 124 via Bluetooth or other connection to download BG data from the memory 114c of the glucometer, and transmit the downloaded BG data through the network 20. In other examples, the smartphone 110b may receive recommended insulin doses over the network 20 from the dosing controller 160 and provide the recommended insulin doses to the glucometer 124 and/or insulin administration device 123a, 123b.

In some implementations, some functions or processes are used within the SubQ outpatient program 200 (FIG. 2) and SubQ outpatient process 1800 (FIGS. 5A and 5B) such as determining the general and pre-meal correction (FIG. 3), determining the adjustment factor AF (FIG. 4), and hypoglycemia treatment.

Referring to FIG. 3, correction boluses CB are used in the SubQ outpatient program 200 (FIG. 2) and process 1800 (FIG. 5A) (FIG. 5B); because of this, correction boluses CB may be incorporated into a function having variables such as the blood glucose measurement BG of a patient 10, a patient's personalized target blood glucose $BG_{Target}$, and a correction factor CF. Thus, correction boluses CB are described as a function of the blood glucose measurement BG, the target blood glucose $BG_{Target}$, and the correction factor CF (see EQ. 7 below). The process 700 calculates the correction bolus CB immediately after a blood glucose value BG of a patient 10 is measured. Once a calculation of the correction bolus CB is completed, the patient 10 administers the correction bolus CB to the patient 10, right after the blood glucose value BG is measured and used to calculate the correction bolus CB.

In some examples, the process 700 may determine the total daily dose TDD of insulin once per day, for example, every night at midnight or at the next opening of the given patient's record after midnight. Other times may also be available. In addition, the total daily dose TDD may be calculated more frequently during the day, in some examples, the total daily dose TDD is calculated more frequently and considers the total daily dose TDD within the past 24 hours. The process 700 provides a timer 702, such as a countdown timer 702, where the timer 702 determines the time the process 700 executes. The timer 702 may be a count up timer or any other kind of timer. When the timer 702 reaches its expiration or reaches a certain time (e.g., zero for a countdown timer 702), the timer 702 executes the process 700. The counter 702 is used to determine at what time the process 700, at block 704, calculates the total daily dose TDD. If the counter is set to 24 hours for example, then decision block 704 checks if the time has reached 24 hours, and when it does, then the process 700 calculates the total daily dose TDD of insulin. Block 706 may receive insulin dosing data from a merged database 1906 (FIG. 6A) within the non-transitory memory 24, 114, 144 via Entry Point T. The correction bolus process 700 determines a total daily dose of insulin TDD, based on the following equation:

$$TDD = \text{Sum over previous day(all basal+all meal boluses+all correction boluses)} \quad (5A)$$

For some configurations, the TDD is calculated as the sum of the latest recommended insulin doses:

$$\text{Alternate } TDD = \text{Sum of(latest recommended basal+} \\ \text{latest recommended Breakfast Bolus+Latest} \\ \text{Recommended Lunch Bolus+Latest Recom-} \\ \text{mended Dinner Bolus)} \quad (5B)$$

After the process 700 determines the total daily dose TDD of insulin at block 706, the process 700 determines a Correction Factor CF immediately thereafter at block 710, using the calculated total daily dose TDD from block 706 and EQ. 5. The correction factor CF is determined using the following equation:

$$CF = CFR/TDD \quad (6)$$

where CFR is a configurable constant stored in the non-transitory memory 24, 114, 144 of the system and can be changed from the setup screen (FIG. 2D). At block 708, the process 700 retrieves the configurable constant CFR value from the non-transitory memory 24, 114, 144 to calculate the correction factor CF at block 710. The configurable constant CFR is determined from a published statistical correlation and is configurable by the hospital, nurses and doctors. The flexibility of modifying the correction constant CF, gives the system 100 flexibility when a new published configurable constant CFR is more accurate than the one being used. In some examples, the configurable constant CFR is a configurable constant set to 1700, other values may also be available. In some examples, the total daily dose TDD and CF are determined once per day (e.g., at or soon after midnight).

Once the correction factor CF is determined in EQ. 6, the process 700 determines the correction bolus insulin dose at block 714 using the following equation:

$$CB=(BG-BG_{Target})/CF) \tag{7}$$

where BG is the blood glucose measurement of a patient 10 retrieved at block 712, $BG_{Target}$ is the patient's personalized Target blood glucose, and CF is the correction factor. The process 700 returns the correction bolus CB at block 716. Rapid-acting analog insulin is currently used for Correction Boluses because it responds quickly to a high blood glucose BG. Also rapid acting analog insulin is currently used for meal boluses; it is usually taken just before or with a meal (injected or delivered via a pump). Rapid-acting analog insulin acts very quickly to minimize the rise of patient's blood sugar which follows eating.

A Correction Bolus CB is calculated for a blood glucose value BG at any time during the program 200. Pre-meal Correction Boluses CB, are calculated using EQ. 7. In the Pre-meal Correction Bolus equation (7) there is no need to account for Remaining Insulin $I_{Rem}$ because sufficient time has passed for almost all of the previous meal bolus to be depleted. However, post-prandial correction boluses (after-meal correction boluses) are employed much sooner after the recent meal bolus and use different calculations that account for remaining insulin $I_{Rem}$ that remains in the patient's body after a recent meal bolus. Rapid-acting analog insulin is generally removed by a body's natural mechanisms at a rate proportional to the insulin remaining $I_{Rem}$ in the patient's body, causing the remaining insulin $I_{Rem}$ in the patient's body to exhibit a negative exponential time-curve. Manufacturers provide data as to the lifetime of their insulin formulations. The data usually includes a half-life or mean lifetime of the rapid-acting analog insulin. The half-life of the rapid-acting analog insulin may be converted to mean lifetime by the conversion formula:

$$mean\ lifetime=Half\text{-}life*ln(2) \tag{8A}$$

where ln(2) is the natural logarithm {base e} of two.

In some implementations, the process 700 accounts for post-prandial correction boluses by determining if there is any remaining insulin $I_{Rem}$ in the patient's body to exhibit a negative exponential time-curve. At block 718, process 700 initializes a loop for determining $I_{Rem}$ by setting $I_{Rem}$ equal to zero, and retrieves a next earlier insulin dose (Dprev) and the associated data-time ($T_{Dose}$) at block 720.

The brand of insulin being used is associated with two half-life parameters: the half-life of the insulin activity (HLact) and the half-life of the process of diffusion of the insulin from the injection site into the blood (HLinj). Since the manufacturers and brands of insulin are few, the program 200 maintains the two half-lives of each insulin brand as configurable constants. These configurable constants can be input by a healthcare provider using an input screen of FIG. 2G. For instance, the display 146 of the healthcare provider computing system 140 can display the input screen 2000 to enable the healthcare provider to input the configurable constants.

For a single previous dose of insulin Dprev, given at a time $T_{Dose}$, the insulin remaining in the patient's body at the current time $T_{current}$ refers to the Remaining Insulin $I_{Rem}$. The derivation of the equation for $I_{Rem}$ involves a time-dependent two-compartment model of insulin: The insulin in the injection site Iinj(t) and the "active" insulin in the blood and cell membrane, Iact(t). The differential equation for Iinj(t) is:

$$dIinj/dt=-(0.693/HLinj)*Iinj(t). \tag{8B}$$

The differential equation for Iact(t) is:

$$dIact(t)/dt=(0.693/HLinj)*Iinj(t)-(0.693/HLact)*Iact (t) \tag{8C}$$

Equations 8B and 8C are simultaneous linear first-order differential equations. The solutions must be added together to represent the total insulin remaining, $I_{Rem}$. The final result can be written as a time-dependent factor that can be multiplied by the initial dose Dprev to obtain the time-dependent total remaining insulin IRem.

Process 700 determines, at block 724, $I_{Rem}$ by multiplying the previous single dose of insulin Dprev {e.g. a Meal Bolus, Correction Bolus, or combined bolus} times a time-dependent factor as follows:

$$I_{Rem}(single\ dose)=Dprev*EXP(-(T_{current}-T_{Dose})*0.693/HLinj)+D0*0.693/HLinj/(0.693/HLact-0.693/HLinj)+Dprev*(EXP(-(T_{current}-T_{Dose})*0.693/HLinj)-EXP(-(T_{current}-T_{Dose})*0.693/HLact)) \tag{9A}$$

The Remaining Insulin $I_{Rem}$ may account for multiple previous doses occurring in a time window looking backwards within a lifetime of the insulin being used. For example, $I_{Rem}$ may be associated with a configurable constant within the range of 4 to 7 hours that represents the lifetime of rapid analog insulin. For example, $I_{Rem}$ may be determined as follows:

$$I_{Rem}=sum\ of\ [I_{Rem}(single\ dose)over\ all\ doses\ in\ the\ within\ the\ lifetime\ of\ the\ insulin\ being\ used] \tag{9B}$$

Process 700 iteratively determines $I_{Rem}$ in the loop until, at block 722, the difference between the current time $T_{current}$ and the time at which the bolus was administered $T_{Dose}$ is greater than a time related to the lifetime of the insulin used. Thus, when block 722 is "NO", process 700 calculates, at block 714, a post meal correction bolus CBpost that deducts the remaining insulin $I_{Rem}$ in the patient's body as follows:

$$CB_{post} = \frac{(BG - BG_{Target})}{CF} - I_{Rem} \tag{10}$$

In some examples, Post Meal Correction doses $CB_{Post}$ (EQ. 10) are taken into consideration only if they are positive (units of insulin), which means a negative value post meal correction bolus $CB_{Post}$ cannot be used to reduce the meal bolus portion of a new combined bolus.

Figure 4:
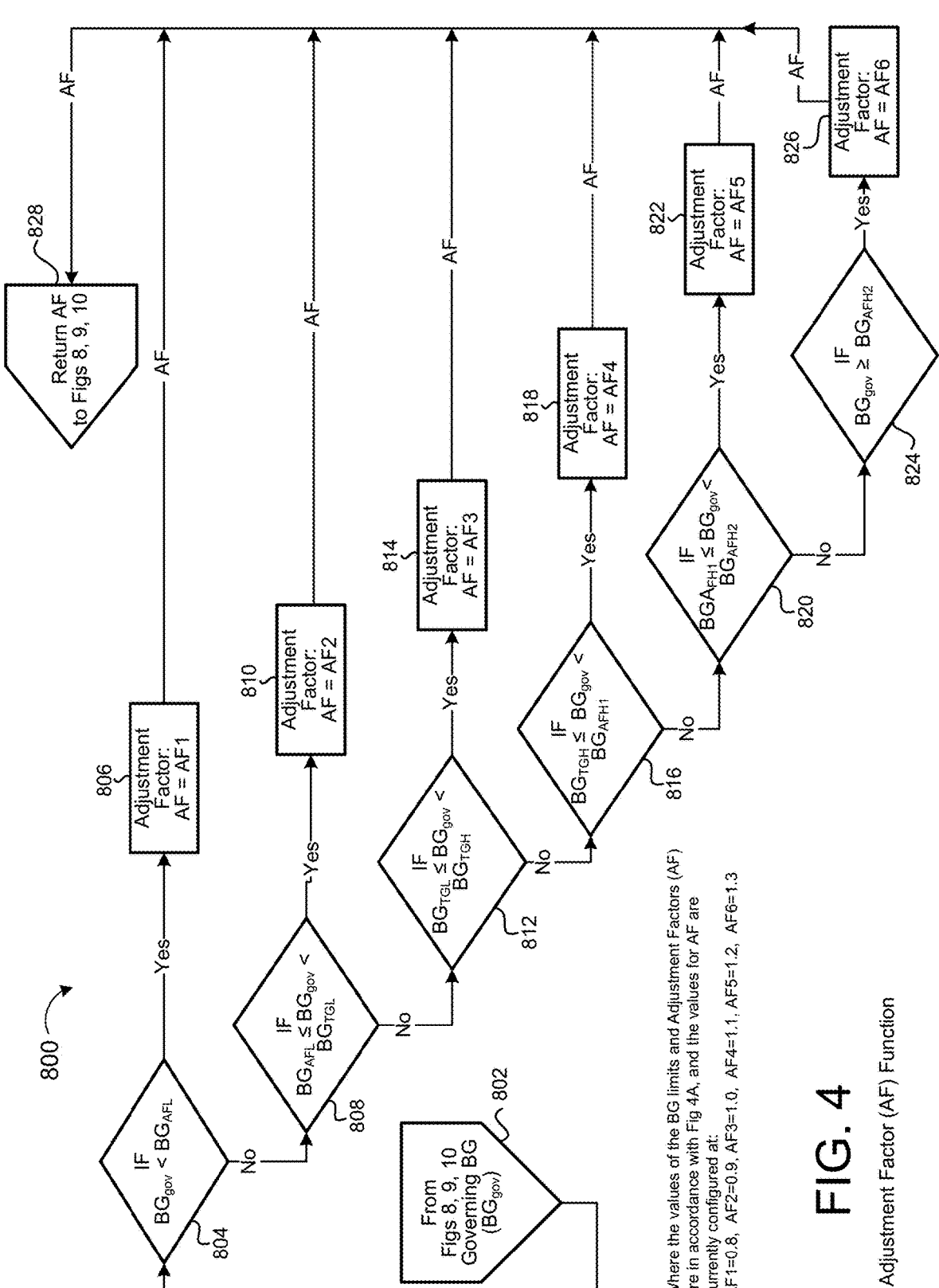
FIG. 4 is a schematic view of an example adjustment factor process.

Referring to FIG. 4, process 800 describes a function that determines an Adjustment Factor AF based on an input of a Governing Blood GlucoseBGgov. The Adjustment Factor AF is used by the SubQ outpatient process 1800 (FIGS. 5A and 5B) for calculating a next recommended basal dose using a basal adjustment process 2300 (FIG. 8), for calculating next recommended meal boluses (e.g., Breakfast, Lunch, and Dinner Boluses) using a meal bolus adjustment process 2400 (FIG. 9), and for calculating a next recommended Carbohydrate-Insulin-Ratio (CIR) using CIR adjustment process 2500 (FIG. 10). An insulin adjustment process 2300, 2400, applied to Basal doses and Meal Boluses, determines an adjusted Recommended Basal dose RecBasal, or a Recommended Meal Bolus RecMealBol, by applying a unit-less Adjustment Factor AF to the preceding recommendation of the same dose, RecBasal$_{prev}$, or RecMealBol$_{prev}$. All dose adjustments are governed by a Governing Blood Glucose value BG$_{gov}$. The Governing Blood Glucose values BG$_{gov}$ in the process are selected based on the criteria of preceding the previous occurrence of the dose to be adjusted by a sufficient amount of time for the effect (or lack of effect) of the insulin to be observable and measurable in the value of the BG$_{gov}$.

At block 802, the adjustment factor process 800 receives the Governing Glucose value BG$_{gov}$ from non-transitory memory 24, 114, 144, since the adjustment factor AF is determined using the Governing Glucose value BG$_{gov}$. To determine the adjustment factor AF, the adjustment factor process 800 considers the blood glucose target range BG$_{TR}$ (within which Basal doses and Meal Boluses, are not changed), which is defined by a lower limit, i.e., a low target BG$_{TRL}$ and an upper limit, i.e., a high target BG$_{TRH}$. As previously discussed, the target range BG$_{TR}$ is determined by a doctor 40 and entered manually (e.g., using the patient device 110 or the medical record system 140, via, for example, a drop down menu list displayed on the display 116, 146). Each target range BG$_{TR}$ is associated with a set of configurable constants including a first constant BG$_{AFL}$, a second constant BG$_{AFH1}$, and a third constant BG$_{AFH2}$ shown in the below table.

TABLE 1

| Target Range Settings | | | | | |
|---|---|---|---|---|---|
| Input Ranges | BG$_{AFL}$ | BG$_{TRL}$ | BG$_{TRH}$ | BG$_{AFH1}$ | BG$_{AFH2}$ |
| 70-100 | 70 | 70 | 100 | 140 | 180 |
| 80-120 | 80 | 80 | 120 | 160 | 200 |
| 100-140 | 70 | 100 | 140 | 180 | 220 |
| 120-160 | 90 | 120 | 160 | 200 | 240 |
| 140-180 | 110 | 140 | 180 | 220 | 260 |

The adjustment factor process 800 determines, at block 804, if the Governing Glucose value BG$_{gov}$ is less than or equal to the first constant BG$_{AFL}$ (BG$_{gov}$<=BG$_{AFL}$), if so then at block 806, the adjustment factor process 800 assigns the adjustment factor AF to a first pre-configured adjustment factor AF1 shown in Table 2.

If, at block 804, the Governing Glucose value BG$_{gov}$ is not less than the first constant BG$_{AFL}$, (i.e., BG$_{gov}$≥BG$_{AFL}$), then at block 808, the adjustment factor process 800 determines if the Governing Glucose value BG$_{gov}$ is greater than or equal to the first constant BG$_{AFL}$ and less than the low target BG$_{TRL}$ of the target range BG$_{TR}$ (BG$_{AFL}$≤BG$_{gov}$<BG$_{TRL}$). If so, then the adjustment factor process 800 assigns the adjustment factor AF to a second pre-configured adjustment factor AF2, at block 810. If not, then at block 812, the adjustment factor process 800 determines if the Governing Glucose value BG$_{gov}$ is greater than or equal to the low target BG$_{TRL}$ of the target range BG$_{TR}$ and less than the high target level BG$_{TRH}$ of the target range BG$_{TR}$ (BG$_{TRL}$≤BG$_{gov}$<BG$_{TRH}$). If so, then the adjustment factor AF to a third pre-configured adjustment factor AF3, at block 814. If not, then at block 816, the adjustment factor process 800 determines if the Governing Glucose value BG$_{gov}$ is greater than or equal to the high target level BG$_{TRH}$ of the target range BG$_{TR}$ and less than the second constant BG$_{AFH1}$ (BG$_{TRH}$≤BG$_{gov}$<BG$_{AFH1}$). If so, then the adjustment factor process 800 assigns the adjustment factor AF to a fourth pre-configured adjustment factor AF4, at block 818. If not, then at block 820, the adjustment process 800 determines if the Governing Glucose value BG$_{gov}$ is greater than or equal to the second constant BG$_{AFH1}$ and less than the third constant BG$_{AFH2}$ (BG$_{AFH1}$≤BG$_{gov}$<BG$_{AFH2}$). If so, then the adjustment factor process 800 assigns the adjustment factor AF to a fifth pre-configured adjustment factor AF5, at block 822. If not, then at block 824, the adjustment process 800 determines that the Governing Glucose value BG$_{gov}$ is greater than or equal to the third constant BG$_{AFH2}$ (BG$_{gov}$≥BG$_{AFH2}$); and the adjustment factor process 800 assigns the adjustment factor AF to a sixth pre-configured adjustment factor AF6, at block 826. After assigning a value to AF the adjustment factor process 800 returns the adjustment factor AF to the process requesting the adjustment factor AF at block 828 (e.g., the SubQ outpatient process 1800 (FIG. 5A) (FIG. 5B)).

TABLE 2

| Configurable values for Adjustment Factor AF | |
|---|---|
| AF1= | 0.8 |
| AF2= | 0.9 |
| AF3= | 1 |
| AF4= | 1.1 |
| AF5= | 1.2 |
| AF6= | 1.3 |

Figure 5A:
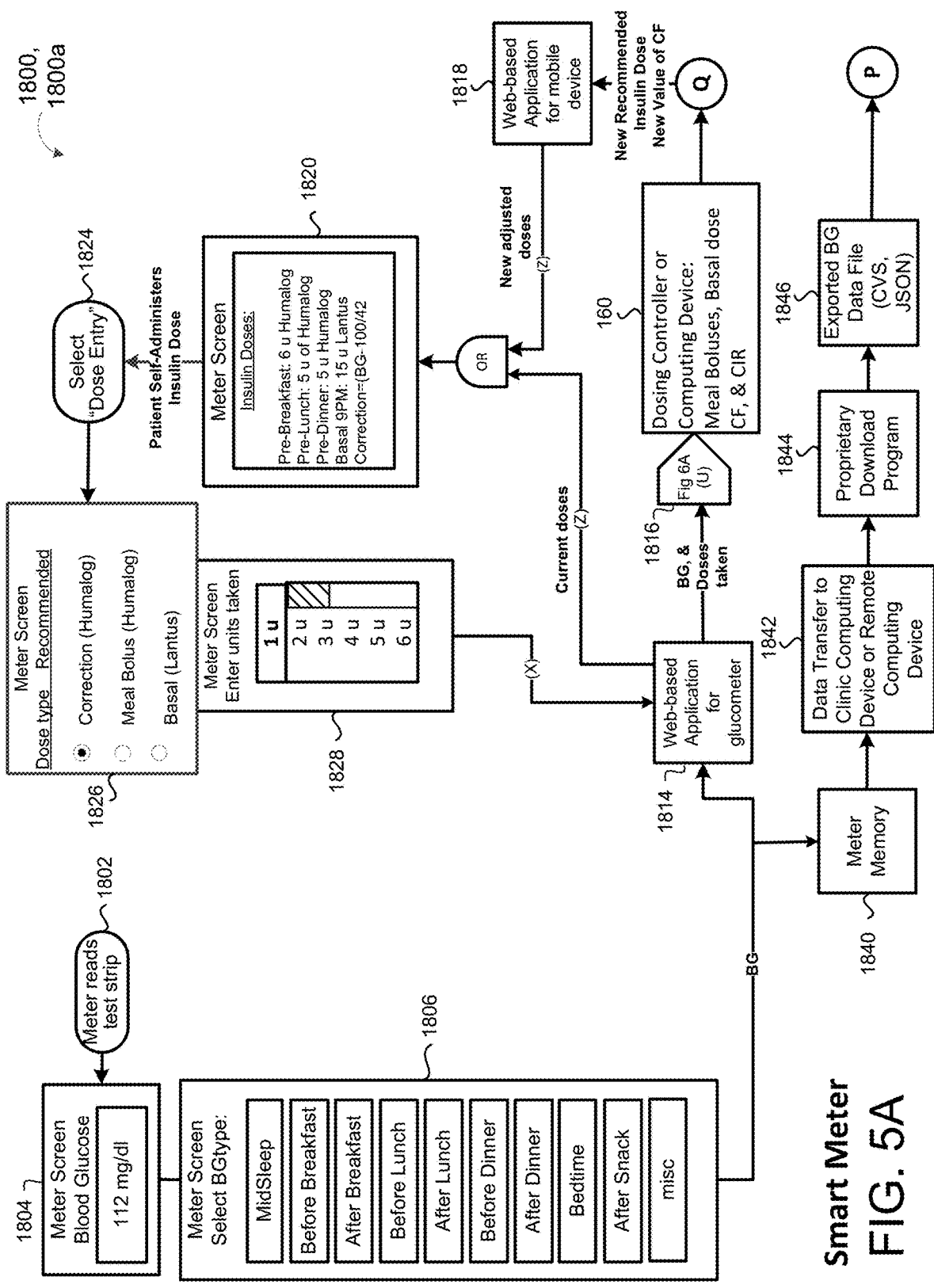
FIG. 5A is a schematic view of an example outpatient process using a mobile device capable of measuring blood glucose.
Figure 5B:
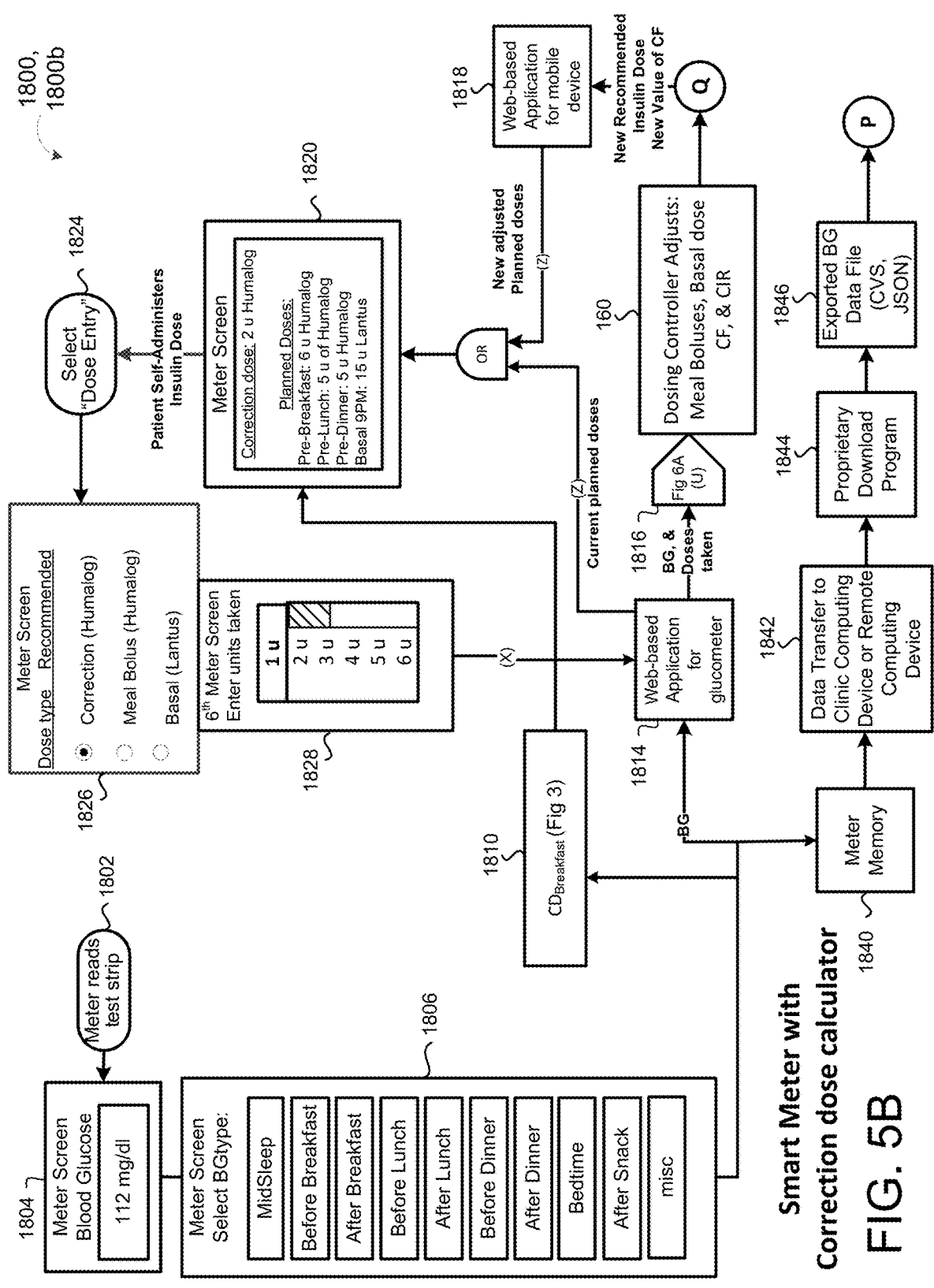
FIG. 5B is a schematic view of an example outpatient process using mobile device capable of measuring blood glucose and calculating a corrective bolus of insulin.

Referring to FIGS. 2A, 5A, and 5B, if the user 40 initiates a subcutaneous output patient process 1800 through selection of program 200 at block 226, the subcutaneous outpatient process 1800 utilizes the patient information 208a and the patient SubQ information 216a input by the user 40 or the patient 10, as shown in FIGS. 2B-2F.

Basal insulin is for the fasting insulin-needs of a patient's body. Therefore, the best indicator of the effectiveness of the basal dose is the value of the blood glucose BG after the patient 10 has fasted for a period of time. Meal Boluses are for the short-term needs of a patient's body following a carbohydrate-containing meal. Therefore, the best indicator of the effectiveness of the Meal Bolus is a blood glucose measurement BG tested about one mean insulin-lifetime iLifeRapid after the Meal Bolus, where the lifetime is for the currently-used insulin type. For rapid-acting analog insulin the lifetime is conveniently similar to the time between meals.

FIG. 5A and FIG. 5B show the SubQ outpatient process 1800a, 1800b, respectively, for a patient 10 using patient portable devices including the glucometer 124 and the patient device 110a or smartphone 110b for communicating with, or optionally executing, the dosing controller 160, based upon selection of blocks 110b and 124 of program 200 (FIG. 2A) The SubQ outpatient process 1800 may be similarly utilized for portable devices including the insulin pen 123b and the infusion pump 123a having "smart" capabilities for communicating with the dosing controller 160.

Referring to FIG. 5A the process 1800a executes by a blood glucose meter without a built-in correction dose calculator. The SubQ outpatient process 1800a begins with a patient's 18 manual entry of a blood glucose measurement BG at block 1802. The SubQ outpatient process 1800a, at block 1804, displays the result of the blood glucose measurement (e.g., 112 mg/dl) and prompts the patient 10 to select a BGtype from a dropdown list 1806. The selection list is provided so that the patient can choose the appropriate BGtype indicating which meal and whether the blood glucose measurement BG is "Before-Meal" or "After-Meal", and also listing other key blood glucose testing times such as Bedtime and MidSleep (generally about 03:00 AM). The BGtype is associated with a blood glucose time BGtime associated with a time of measuring the blood glucose measurement. In the example shown, the SubQ outpatient process 1800a allows the patient to select a pre-breakfast blood glucose measurement, a pre-lunch blood glucose measurement, a pre-dinner blood glucose measurement, a bedtime blood glucose measurement, or a midsleep blood glucose measurement.

In some implementations, the glucometer 124 may not be configured to display the BGtype selections as shown at block 1806, and instead, determines if the time at which the blood glucose BG was measured BGtime falls within one of a number of scheduled blood glucose time buckets, that are contiguous so as to cover the entire day with no gaps. Further, the BGtypes are provided with Ideal BG Time Intervals, where each ideal scheduled time is associated with an interval configured with a start time margin ($M_{start}$) and an end time margin ($M_{End}$). Moreover, each interval may be associated with a corresponding BGtype: pre-breakfast blood glucose measurement, a pre-lunch blood glucose measurement, a pre-dinner blood glucose measurement, a bedtime blood glucose measurement, or a midsleep blood glucose measurement Referring to FIG. 5B, the process 1800b uses a blood glucose meter having a built-in correction dose calculator. Using a processor of the glucometer 124, the SubQ outpatient process 1800, at block 1810, determines a Correction Dose of insulin for the selected (or determined) BGtype (e.g., pre-breakfast) using the following equation (based on EQ. 2):

$$CB_{Breakfast}=(BG_{Breakfast}-BG_{Target})/CF \qquad (11)$$

Additionally or alternatively, the Correction Dose may be determined using the Correction Dose Function of process 700 (FIG. 3). For example, when the blood glucose meter does not include a built-in correction dose calculator, process 1800a (FIG. 5A) may allow a healthcare provider, via the dosing controller 160, to load the Correction Factor (CF) upon the glucometer 124 based upon an immediately preceding BG measurement. In other examples, meters or other devices may use the correction dose formula of process 700 (FIG. 3), which may incorporate a deduction for the Remaining Insulin $I_{Rem}$.

The SubQ outpatient process 1800b (FIG. 5B), at block 1820, displays the Correction Dose for the BGtype determined at block 1810 on a Meter Screen of the glucometer display 116c. In some implementations, the SubQ outpatient process 1800a (FIG. 5A) stores blood glucose data BGdata, including the recent correction dose CD, the blood glucose measurement BG, the BGtype, and the $BG_{TIME}$, in the glucometer's 124 memory 114c at block 1840, and at a later time, the SubQ outpatient process 1800 uses a batch process, at blocks 1842-1846, for downloading the data from the glucometer 124 to the non-transitory 24, 114, 144 for the dosing controller 160 to retrieve for determining or adjusting recommended insulin doses for the patient 10. In some examples, the glucometer 124 transfers data to the computing device 112 or 142 at block 1842, and a proprietary download program 196 provided by the manufacturer of the glucometer 124 executes on the computing device 112 or 142 to download the data at block 1844. For instance, the patient 12 may connect the glucometer 124 to the computing device 142 when the patient 12 visits a clinic 42 during a regular check-up. The data transfer may be facilitated by connecting the glucometer 124 to the computing device 112 or 142 using Bluetooth, Infrared, near field communication (NFC), USB, or serial cable, depending upon the configuration of the glucometer 124. The SubQ outpatient process 1800a, at block 1846, exports the data downloaded by the proprietary download program 196 as a formatted data file for storage within the non-transitory 24, 114, 144 for the dosing controller 160 to retrieve when determining or adjusting insulin parameters for the patient 10 at entry point P. For example, the exported data file may be a CVS file or JSON file accessible to the computing devices 132, 142 of the dosing controller 160.

Referring back to block 1806, in some implementations, the SubQ outpatient process 1800a, 1800b provides the blood glucose BG data, including the recent correction dose CD, the blood glucose measurement BG, the BGtype, and the $BG_{TIME}$, in real time to a web-based application 198 of the manufacturer of the glucometer 124 at block 1814, and in turn, the web-based application 198 of the manufacturer via the network 20 may format a data file of the BG data for storage in the non-transitory memory 24, 114, 144 at block 1816. The glucometer 124 may sync the BG data with a mobile device, such as the smart phone 110b, to wirelessly transmit the BG data to the web-based application 198 at block 1814. The computing devices 132, 142 of the dosing controller 160 may retrieve the exported BD data file for calculating a next recommended insulin dose and a new value for the Correction Factor (CF) for the patient 10 at entry point Q. The next recommended insulin doses for adjusting the basal and the CF may be input to entry point Q using a basal adjustment process 2300 (FIG. 8), while recommended insulin doses for meal boluses may be input to entry point Q using a meal bolus adjustment process 2400 (FIG. 9). In some examples, the glucometer 124 is configured to connect to the network 20 and transmit the blood glucose data directly to the manufacturer's web-based application 198. In other examples, the glucometer 124 syncs with the smart phone or other mobile device 110b to connect to the network 20 and transmit the blood glucose data to the manufacturer's web-based application 198. In some examples, the glucometer 124 syncs with the smart insulin pump 123a or smart insulin pen 123b to connect to the network 20 and transmit the blood glucose data to the manufacturer's web-based application 198. The smart insulin pump 123a or smart insulin pen 123b including administration computing devices 112d or 112e configured to communicate the BG data to the dosing controller 160 and execute the SubQ outpatient program 200 transmitted from the dosing controller 160 causing a doser 223a, 223b to administer recommended insulin doses specified by the SubQ outpatient program 200.

The SubQ outpatient process 1800a, 1800b transmits via the network 20 the next recommended insulin dose and the new value for the CF for the patient 10 calculated at 1816 to the web-based application 198 of the meter manufacturer at block 1818, wherein the web-based application 198 of the meter manufacturer formats the next recommended insulin dose and the new value for the CF for the glucometer 124 to receive via the network 20. In some examples, the web-based application 198 transmits the next recommended dose and the new value for the CF to a mobile device, such as the smart phone 110b, via the network 20 the mobile device 110*b* syncs with the glucometer 124 (and/or smart pen 123*b*) to provide the next recommended dose and the new value for the CF to the glucometer 124 (and/or the smart pen 123*b*). For instance, the number of insulin units associated with the recommended dose may be automatically measured by the smart pen 123*b* or smart pump 123*a*. Next, the SubQ outpatient process 1800 displays the next recommended insulin dose for the breakfast meal bolus on a Meter Screen via display 116*c* at block 1820.

After the patient self-administers the insulin dose (or the dosing controller 160 executing the SubQ outpatient process 1800*a*, 1800*b* causes the doser 223*a*, 223*b* to administer the insulin dose), at block 1824, the process 1800*a*, 1800*b* determines that the patient 10 has selected a "Dose Entry" to record the administered dose. The SubQ outpatient Process 1800*a*, 1800*b* then prompts the patient 10 to select the insulin dose type on a Meter Screen via display 116*c* at block 1826. The Meter Screen permits the patient to simultaneously select "Correction" and "Meal Bolus" for when the patient 10 has administered a combined dose that the patient 10 would like to record. The selection of "Basal" may not be selected simultaneously with another selection but is operative to cancel out other selections. In response to the patient's selection, the SubQ outpatient process 1800*a*, 1800*b*, at block 1828, presents an insulin drop down menu of populated insulin doses on a Meter Screen via the display 116*c*. Here, the patient 10 may select the number of units of insulin recently administered by the patient 10.

In some implementations, as shown in FIG. 1C, when the patient 10 uses the smart pen 123*b* (or smart pump 123*a*), the SubQ outpatient process 1800 transmits via the network 20 the next recommended insulin dose and the new value for the CF for the patient 10 calculated at entry point Q directly to the smart pen 123*b*, wherein the smart pen 123*b* automatically dials in the recommended dose of insulin without manual input by the patient 10 and may display the dose via the smart pen 123*b* display 116*e*. In other implementations, the smart pen 123*b* syncs (e.g., Bluetooth connection) with the glucometer 124 to receive and automatically dial-in the recommended dose of insulin. In some examples, after the patient 10 administers the insulin dose, the smart pen 123*b* records the number of units of insulin administered by the patient which may be stored in the non-transitory memory 24, 114, 144 via the network 20.

Figure 6A:
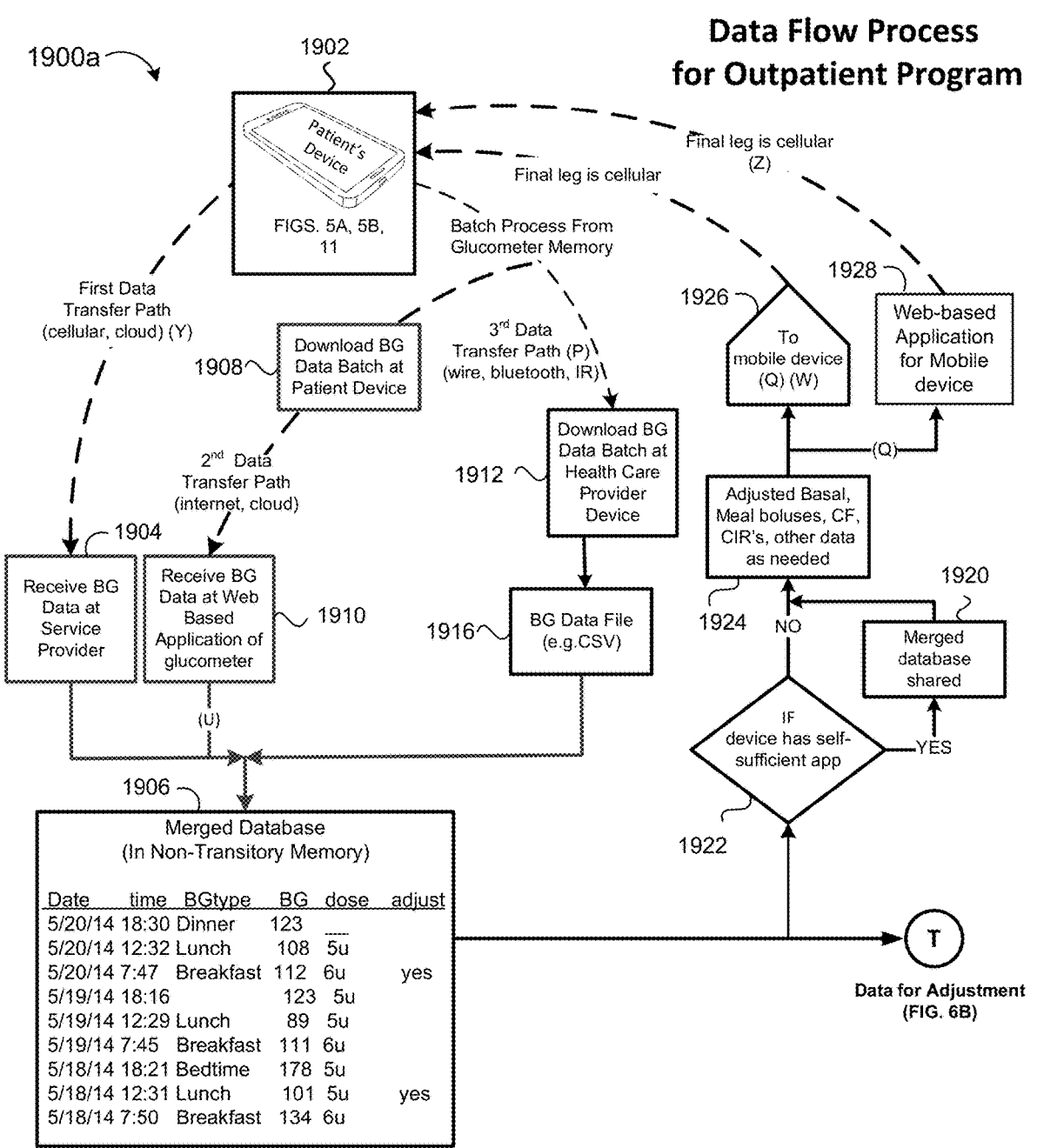
FIG. 6A is a schematic view of an example data transfer process for communicating blood glucose data measured by a patient's glucometer.

FIG. 6A shows a data flow process 1900*a* for storing blood glucose BG data from a patient's mobile device 110*a*, 110*b*, 124, 123*a*, 123*b* within the non-transitory memory 24, 134, 144 in communication with the computing device 112, 132, 142 of the dosing controller 160. The BG data may include, but is not limited to, doses of insulin administered to the patient 10, a blood glucose measurement BG, an associated BGtype, and an associated time of the blood glucose measurement BGtime, as described above with reference to block 1806 of the SubQ outpatient process 1800*a*, 1800*b*. In some implementations, the glucometer 124 syncs with the patient's mobile device 110*a*, 110*b*, 124, 123*a*, 123*b* to transfer the BG data at block 1902. In the example shown, the mobile device is the smart phone 110*b*. The data flow process 1900*a* permits the mobile device 110*b* to transmit the BG data for storage in the non-transitory memory 24, 134, 144 by using one of three data transfer paths.

In some implementations, the data flow process 1900*a* sends the BG data in real-time via a first data transfer path from the mobile device 110*b* at block 1902. The first data transfer path may always be available provided the mobile device 110*b* is able to connect to the network 20 or cellular service. In some scenarios, the data flow process 1900*a*, at block 1902, sends the BG data in real-time via the first data transfer path from the mobile device 110*b* to the computing device 192 of the service provider 130. Thereafter, the data flow process 1900*a* transmits the BG data from the first data transfer path, at block 1904, to a merged database within the non-transitory memory 24, 134, 144 at block 1906.

In other implementations, the data flow process 1900*a* executes a batch process for downloading the BG data from the memory 114*c* of the glucometer 124 at the patient device 110*a* or other computing device connecting to the network 20 at block 1908, and then, transmits the BG data from the patient device 110*a* via a second data transfer path to a web-based application 198 of the manufacturer of the glucometer 124 at block 1910. In some examples, the batch process downloads all BG data stored on the memory 114*c* of the glucometer 124 for a configurable time period. In other examples, the batch process downloads all BG data stored on the memory 114*c* of the glucometer 124 since an immediately previous download session. The web-based application 198 may format a data file (e.g., merged database) of the BG data for storage in the non-transitory memory 24, 114, 144 at block 1906.

In other implementations, the data flow process 1900*a* executes a batch process for downloading the BG data from the memory 114*c* of the glucometer 124 at the health care provider computing device 142 via a third data transfer path at block 1912. For instance, the patient 10 or health care professional 40 may connect the glucometer 124 to the computing device 142 when the patient 10 visits a clinic 42 associated with a hospital call center during a regular check-up. In some examples, the computing device 142 executes a proprietary download program 196 provided by the manufacturer of the glucometer 124 to download the BG data from the memory 114*c* of the glucometer 124. The BG data transfer may be facilitated by connecting the glucometer 124 to the computing device 142 using Bluetooth, Infrared, near field communication (NFC), USB, or serial cable, depending upon the configuration of the glucometer 124. In some examples, the BG data downloaded at block 1912 may be displayed via display 146 for the health care professional to view. The data flow process 1900*a* receives a user 40 input to load the downloaded BG data (e.g., via a button on display 146), and exports the BG data downloaded by the proprietary download program 196 as a formatted BG data file for storage within the non-transitory 24, 114, 144 at block 1916. For example, the exported BG data file may be a CVS file or JSON file. In some examples, the batch process downloads all BG data stored on the memory 114*c* of the glucometer 124 for a configurable time period. In other examples, the batch process downloads all BG data stored on the memory 114*c* of the glucometer 124 since an immediately previous download session during a previous clinic visit by the patient 10.

In some examples, the non-transitory memory 24, 114, 144 includes a database for storing the BG data of the patient 10 received from any one of the first, second, or third data transfer paths. The database may store the BG data in a designated file associated with the patient 10 and identifiable with a patient identifier associated with the patient 10. The BG data within the database of the non-transitory memory 24, 114, 144 may be retrieved by the dosing controller 160 for determining or adjusting doses of insulin for the patient 10 to administer. Block 1906 may send the data within the merged database to Entry point T for routing to other processes, including a Time Limits of Data for Adjustment process (FIG. 6B).

Moreover, block 1906 may provide the data within the merged database to the patient's mobile device 110*a*, 110*b*, 124, 123*a*, 123*b* at block 1902. For instance, block 1922 may determine if the mobile device includes a self-sufficient application capable of sharing the merged database. If block 1922 is a "YES" indicating that the mobile device includes the self-sufficient application, block 1920 provides the merged database to block 1924 for sharing with the mobile device. Thereafter, block 1924 may provide an adjusted basal dose (from process 2300 of FIG. 8), an adjusted meal dose (from process 2400 of FIG. 9), a correction factor, and/or a carbohydrate-to-insulin ratio CIR (from process 2500 of FIG. 10) over the network 20 directly to the mobile device via Entry Point W at block 1926, or through the web-based application for the mobile device via Entry Point Q at block 1928. If block 1922 is a "NO" indicating that the mobile device does not include a self-sufficient application, block 1924 may provide existing basal doses, meal doses, the correction factor, and/or the carbohydrate-to-insulin ratio over the network 20 to the mobile device at block 1902 via one of block 1926 or block 1928.

Figure 6B:
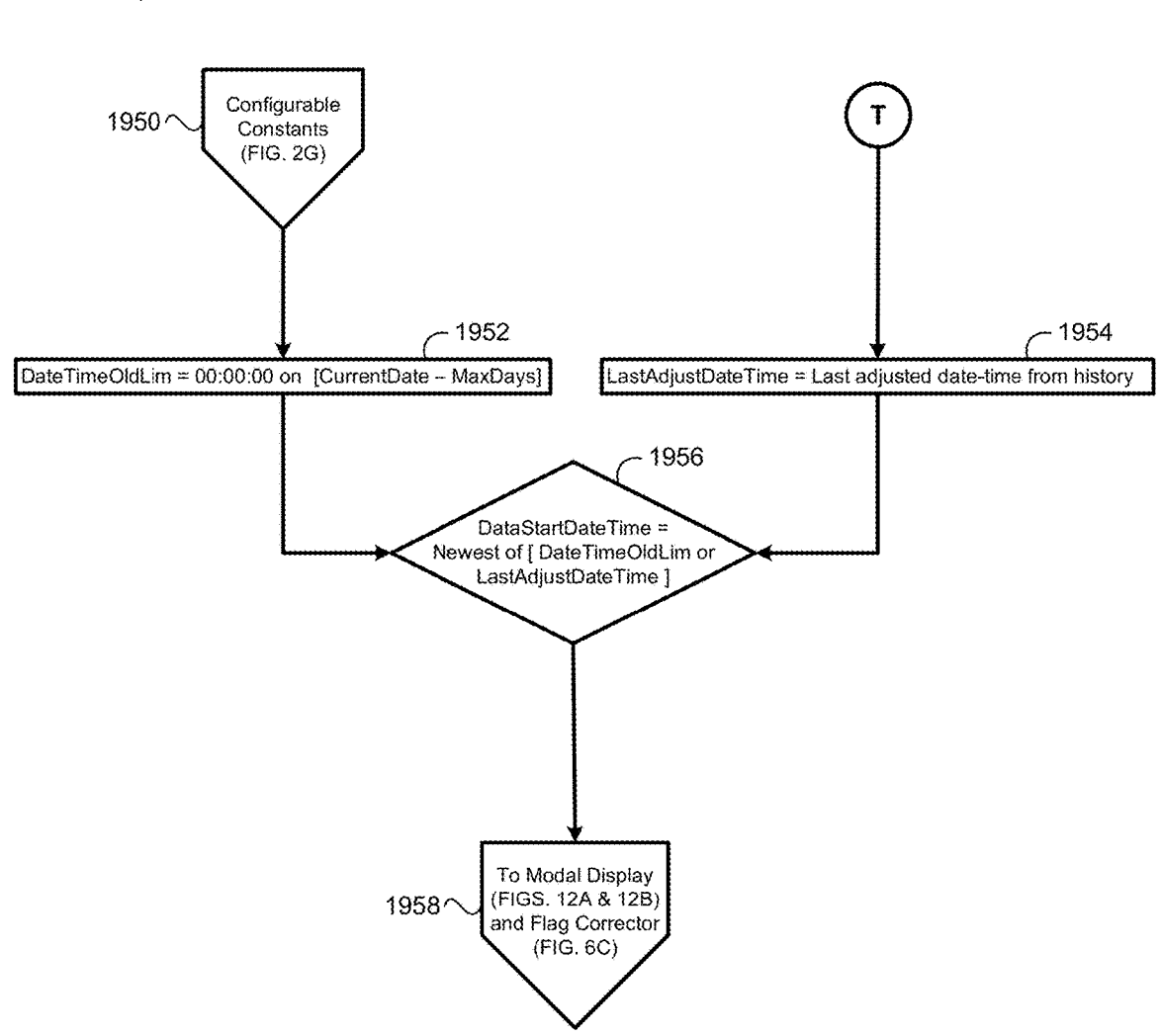
FIG. 6B is a schematic view of an example process for determining an amount of past blood glucose data for use in adjusting dosages of insulin.
Figure 12A:
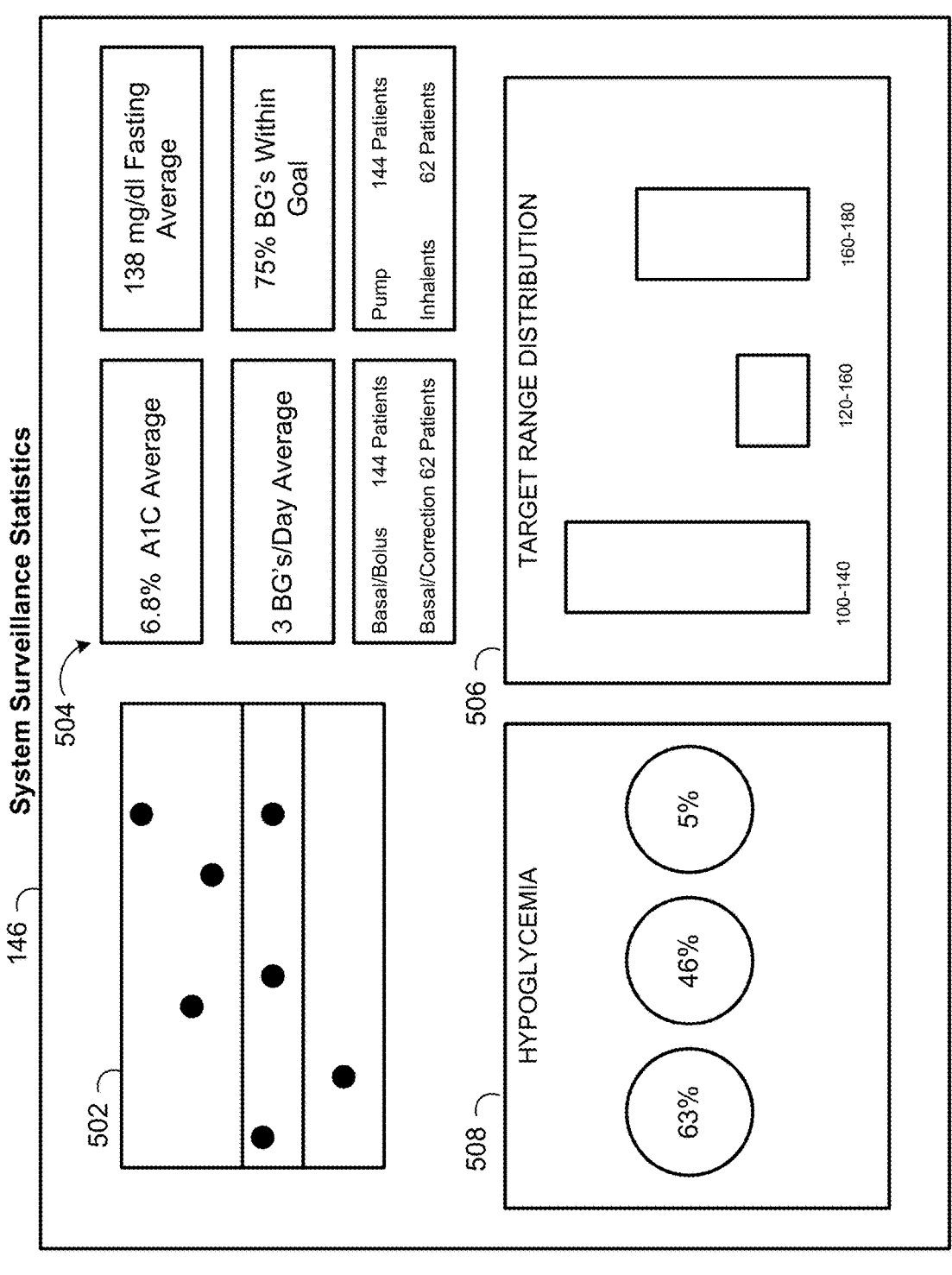
FIG. 12A is a schematic view of an example display for viewing blood glucose data.
Figure 12B:
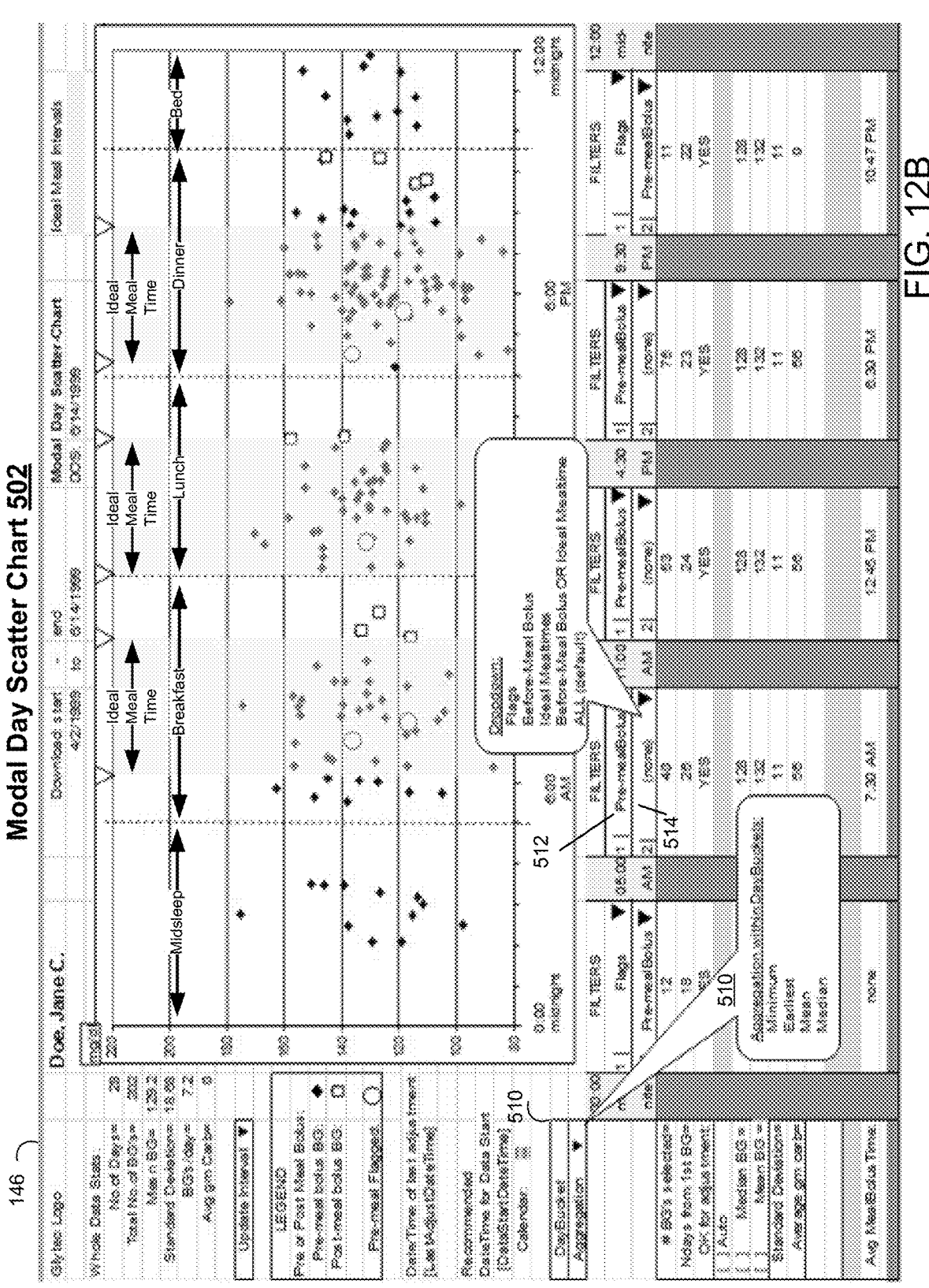
FIG. 12B is a schematic detailed view of an example modal day scatter chart for viewing blood glucose data.

Referring to FIG. 6B, in some implementations, the Limits on Age of Data for Adjustment process 1900*b* receives the data of Entry Point T from the data flow process 1900*a* of FIG. 6A. Additionally, process 1900*b* receives, at block 1950, the configurable constants input at the Healthcare Facility Input Screen 2000 of FIG. 2G, including the constant MaxDays which sets a limit on the amount of data used based on the reasoning that a patient's health can change substantially over several months. The currently configured number for MaxDays is 28 days. Block 1952 shows the oldest allowable date/time (DateTimeOldLim) is midnight (00:00) on the day given by the current date less (minus) the MaxDays. The process 1900*b* determines, at block 1954, the date/time of the last adjustment (LastAdjustDateTime) from the patient's history from Entry Point T. Thereafter, at block 1956, the process 1900*b* determines the beginning date/time for the current adjustment (DataStartDateTime) as the most recent date/time between the DateTimeOldLim (block 1952) or the LastAdjustDateTime (block 1954). The process 1900*b* may then provide the DataStartDateTime to block 1958 for routing to a Flag Corrector process 1900*c* (FIG. 6C) and to a Modal Day Scatter Chart upon the display 146 (FIGS. 12A and 12B).

Figure 6C:
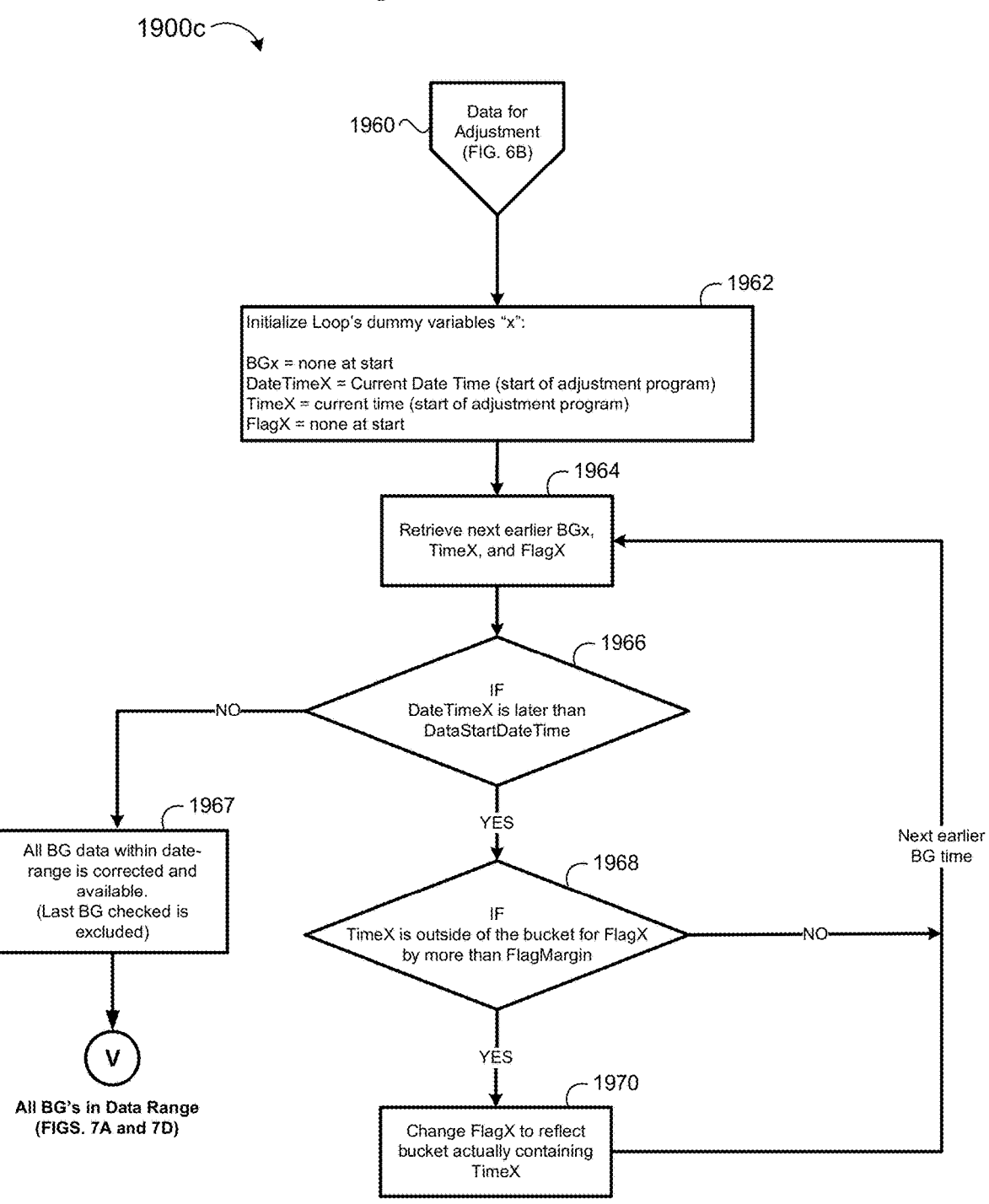
FIG. 6C is a schematic view of an example process for correcting flagged blood glucose measurements to reflect an actual time of the blood glucose measurement.

Blood glucose measurements may be aggregated or flagged according to their associated blood glucose type BGtype or blood glucose time BG time interval to determine a mean or median blood glucose value (EQ. 3) for each BGtype that may be used to determine or adjust recommended doses of insulin (e.g., bolus and/or basal). Referring to FIG. 6C, the Flag Corrector process 1900*c* receives, at block 1960, the BG data from the process 1900*b* (FIG. 6B). The glucometer 124 may include a selectable button to flag the BG measurements with a given BGtype (e.g., pre-Breakfast, pre-Lunch, Bedtime, etc), as shown at the meter screen at block 1804 of FIGS. 5A and 5B (e.g., glucometer display 116*d* (FIG. 1)). In some scenarios, patients may infrequently flag BG measurements or may flag the BG measurements incorrectly. In these scenarios, the process 1900*c* executes a loop to examine all the BG measurements within a specified date range. Prior to executing the loop, the process 1900*c*, at block 1962, initializes variables for the loop to examine all the blood glucose BG measurements in a date range. The initialized variables may be re-usable dummy variables. Thereafter, the loop starts at block 1964 by retrieving each BG measurement moving backward in time. Block 1966 determines whether the date/time of the analyzed BG measurement is later than the DataStartDateTime. If block 1966 determines that the date/time of the BG measurement is not later than the DataStartDateTime (e.g., block 1966 is "NO"), then the loop stops at block 1967. Here, all the BG measurements in the date-range have now been checked and incorrect flags have been corrected; however, the last BG measurement checked/analyzed was not in the date-range and is therefore excluded from routing to Entry Point V. The process 1900*c* routes the corrected data through entry point V, whereby the analyzed BG measurements are selected and provided to either the Typical Non-Meal Bucket process 2200*a* (FIG. 7A) or the Typical Meal Bucket process 2200*b* (FIG. 7D). If, on the other hand, block 1966 determines that the date/time of the BG measurement is not later than the DataStartDateTime (e.g., block 1966 is "YES"), then the analyzed BG measurement is checked at block 1968 to determine whether the BG measurement is outside of the bucket for which it is flagged. For instance, if the time of a BG measurement is outside of a bucket indicated by an associated flag by more than a configurable margin (FlagMargin), then the loop changes the flag to reflect the BGtype indicated by the actual time of the BG measurement. The process 1900*c* then reverts back to block 1964 and retrieves the next earlier BG measurement in time. The process 1900*c* ends executing the loop when block 1970 determines a BG is found earlier than the DataStartDateTime, and all the data in the acceptable date-range is provided to Entry Point V for routing to a BG aggregation process 2200 (FIGS. 7A-7F).

If the time of a BG is outside of the bucket indicated by its flag by more than a configurable margin (FlagMargin) then the flag is changed to reflect the BGtype indicated by the actual time of the BG. The loop uses some dummy variables that are re-used, so they are initialized at the start at 2904. The start of the loop at 2906 starts at the present and retrieves each BG moving backward in time. If the date/time of the BG being checked at 2908 is earlier than the DataStartDateTime, then the loop is stopped, if not then the time of the BG is checked at 2912 to see if it is outside the bucket for which it is flagged. If so then the flag is changed at 2914 to indicate the bucket actually inhabited by the BG. The loop ends when a BG is found earlier than the DataStarteDateTime, and all the data in the acceptable date-time range are sent to Entry Point V for use by the BG aggregation processes 2200*a*, 2200*b*.

FIGS. 7A-7F show the blood glucose BG aggregation process 2200 for aggregating blood glucose BG measurements for a patient 10 according to the times at which the blood glucose measurements are measured. The aggregation process 2200*a*, 2200 of FIGS. 7A-7C aggregates BG measurements that are not associated with times when the patient 10 is not consuming meals, while the aggregation process 2200, 2200*b* of FIGS. 7D-7F aggregates BG measurements associated with times when the patient 10 is consuming meals.

In some examples, the BG measurements are transmitted from the patient's portable device 110*a*, 110*b*, 124, 123*a*, 123*b* and stored within the non-transitory memory 24, 134, 144. For instance, the BG measurements obtained by the glucometer 124 may be communicated and stored within the non-transitory memory 24, 134, 144 by using the data flow process 1900*a*, as described above with reference to FIG. 6A. In some implementations, the BG aggregation process 2200 divides a day into five time intervals corresponding to the five BG types: Midsleep, Breakfast, Lunch, Dinner, and Bedtime. As used herein, the term "time buckets" is used to refer to these time intervals corresponding to the five BG types. The Modal Day Scatter Chart 502 of FIG. 12B shows the time buckets as intervals between the dotted lines. Each bucket is associated with a corresponding time boundary that does not overlap the other time boundaries associated with the other buckets.

Figure 2H:
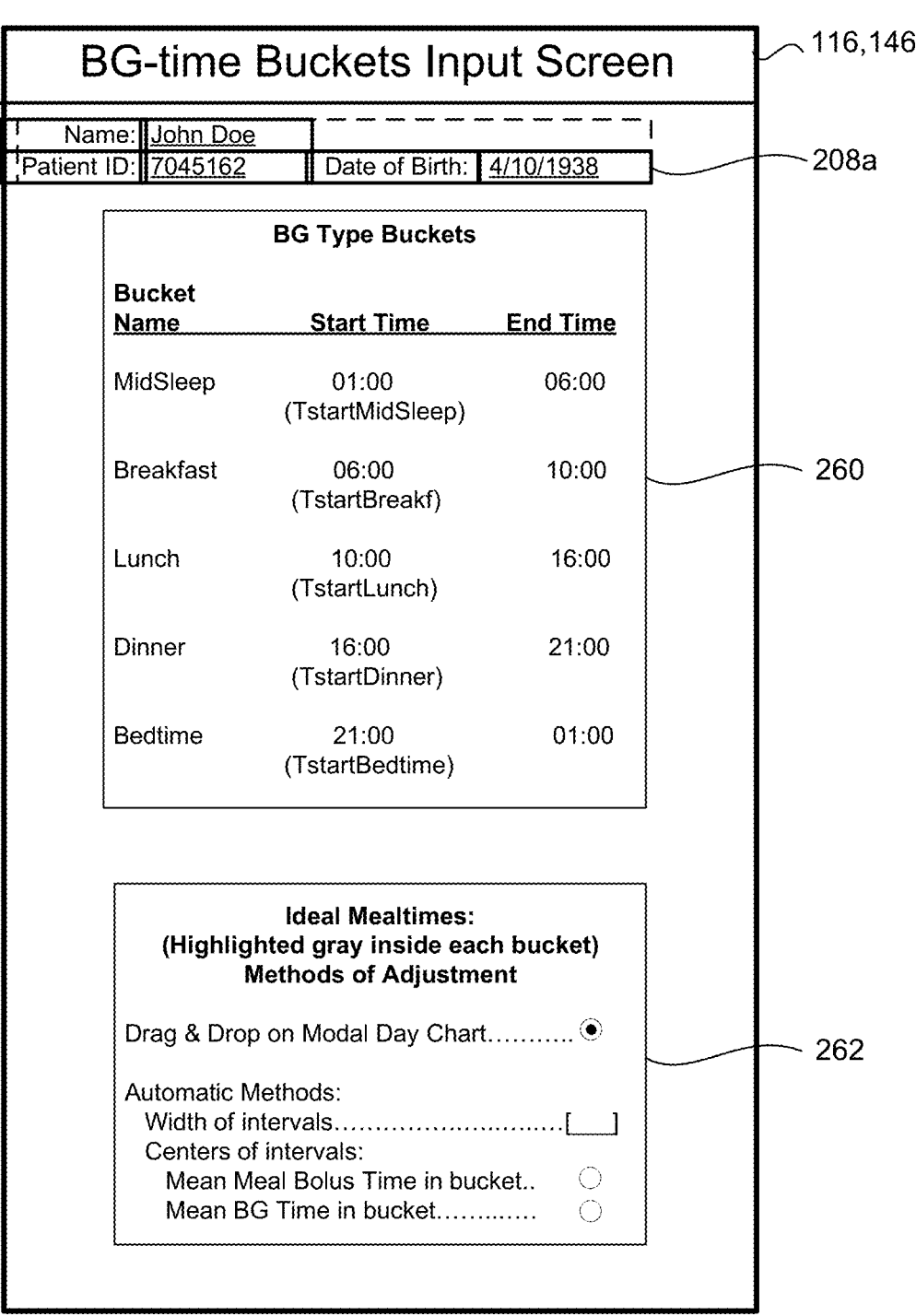
FIG. 2H is a schematic view of an example input screen for inputting time-boundaries for intervals within a day.

Referring to FIG. 2H, in some examples, a BG Time-Bucket input screen permits the user 40 (or patient 10) to adjust the time-boundary associated with each time bucket via the display 116, 146. The BG Time-Bucket input screen displays the patient information 208a and allows the user 40 to input BG Time-Bucket Information 260 and Ideal Meal-time information 262. For instance, the BG Time-Bucket Information 260 includes a bucket name (e.g., MidSleep, Breakfast, Lunch, Dinner, Bedtime) and associated start and end times for each BG time-bucket. Based upon the BG Time-Bucket Information 260 and the Ideal Mealtime infor-mation 262 input to the BG Time-Bucket input screen (FIG. 2H), the BG aggregation process 2200a (FIGS. 7A-7C) may associate the BG time-buckets for MidSleep and Bedtime with time intervals when the patient 10 does not consume meals and the BG aggregation process 2200b (FIGS. 7D-7F) may associate the BG time-buckets for Breakfast, Lunch and Dinner with time intervals when the patient 10 consumes meals.

Referring back to FIG. 12B, the Modal Day Scatter Chart 502 applies a DayBucket to an interval of time within a time-bucket on a specific day. Thus, each time-bucket may include one or more DayBuckets. The user 40 may select an Aggregation Method (AgMeth) for use within each of the DayBuckets from an Aggregation Menu 510 upon the Modal Day Scatter Chart via the display 146. For example, the user 40 may select an AgMeth from the Aggregation Menu 510 that includes one of Minimum Earliest, Mean, or Median for the BG measurements in the associated DayBucket. Accord-ingly, the AgMeth selected by the user results in a single value representing the BG measurements associated with the DayBucket. The BG measurements aggregated by the AgMeth may belong to a union of 1 or more subsets denoted by the symbol "U". These values are further aggregated for each BG Bucket over the days in the updated data. The Modal Day Scatter Chart 502 of FIG. 12B shows the aggregation methods available for this aggregation are mean and median and are governed by the variable (MMtype).

Referring to FIG. 7A, the BG aggregation process 2200a aggregates the BG measurements of the BG time-buckets (e.g., MidSleep and Bedtime) for time intervals when the patient 10 does not consume meals. While FIG. 7A shows the BG aggregation process 2200a aggregating BG mea-surements for the Bedtime BG time-bucket, the BG aggre-gation process 2200a similarly aggregates BG measure-ments for the Midsleep BG time-bucket. The aggregation process 2200a provides the DataStartDataTime (FIG. 6C) via Entry Point V to block 2202 for determining a Nday-sBedtime (or NdaysMidSleep) that counts the number of DayBuckets within the associated bucket (e.g., Bedtime BG time-bucket) from the current date/time backward to an earliest permissible date/time DataStartDateTime. As used herein, the "earliest date" refers to the earliest one of a previous dosing adjustment or the preconfigured MaxDays (FIG. 6B) into the past. The "earliest date" is operative as a safeguard against a patient returning to the healthcare facil-ity after a year, and receiving a subsequent 365 day adjust-ment. Additionally, the aggregation process 2200a deter-mines, at block 2202, a NDayBucketsWBG that counts the number of the DayBuckets containing at least one BG measurement.

At block 2204, the aggregation process 2200a determines a ratio of the DayBuckets containing BG measurements to DayBuckets in the associated bucket (e.g., NDayBuck-etsWBG/NdaysBedtime) and compares the ratio to a con-figurable set point (Kndays). The value of Kndays is pres-ently configured at 0.5. If the ratio is less than Kndays, the aggregation process 2200a prevents, at block 2206, the dosing controller 160 from adjusting the dose governed by the associated time-bucket (e.g., Bedtime BG time-bucket). For example, when the aggregation process 2200a aggre-gates BG measurements for the Bedtime BG time-bucket, block 2206 prevents the adjustment of the Dinner meal bolus when the ratio of NDayBucketsWBG/NdaysBedtime is less than Kndays indicating that the Bedtime BG time-bucket does not contain enough BG measurements. Block 2206 provides the determination that prevents adjusting the dose governed by the associated time-bucket to Entry Point S for use by processes 2300, 2400, 2500 of FIGS. 8, 9, and 10, respectively. On the other hand, if block 2204 determines that the ratio of NDayBucketsWBG/NdaysBedtime is greater than or equal to Kndays, the dosing controller 160 is permitted to adjust the dose governed by the associated time-bucket.

Figure 7B:
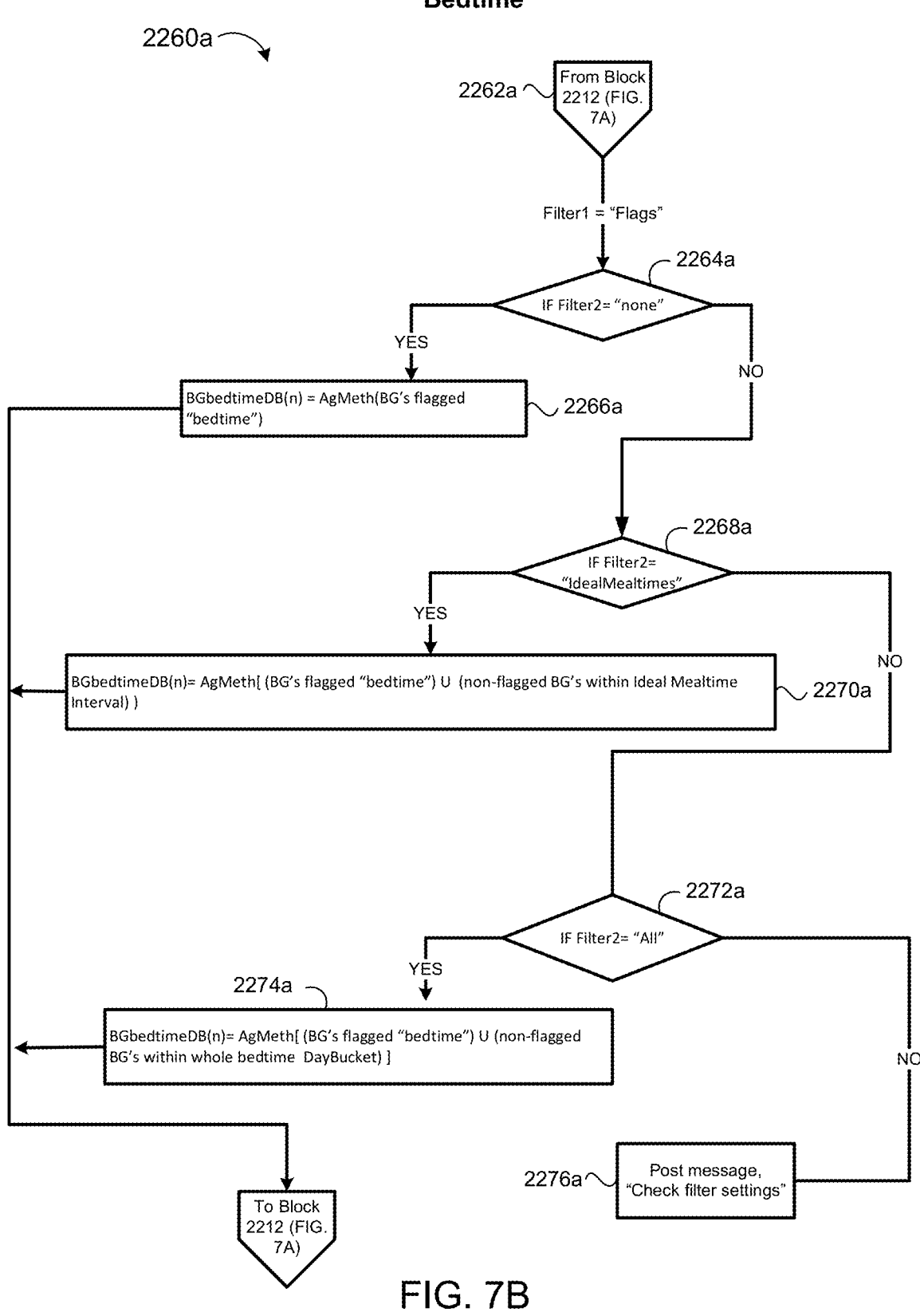

The aggregation process 2200a of FIG. 7A and the aggregation process 2200b of FIG. 7B use a system of filters to determine the best aggregate BG value to represent the associated time-bucket. There are two dropdown filter selec-tions (Filter1 512 and Filter2 514) that the user 40 may select from the Modal Day Scatter Chart 502 of FIG. 12B. Each of the dropdown filter selections 512, 514 allow the user 40 to select from the following selections:

Flags: Uses the flags entered by the patient 10 on the glucometer 124 at test time and corrected as needed by the Flag Corrector Process 1900c (FIG. 6C).

Pre-Meal Bolus: Uses BG Measurements within the bucket that occur earlier than the time of the Meal Bolus (not available for non-meal buckets).

Ideal Meal Time: Shaded areas of the Modal Day Scatter Chart 502 (FIG. 12B) within each associated bucket. Each Ideal Meal Time having boundaries adjustable using drag-and-drop methods by user inputs upon the Modal Day Scatter Chart (FIG. 12B) or via inputs to the Ideal Mealtime information 262 at the BG-time Buckets Input Screen (FIG. 2H).

Both Pre-Meal-bolus OR Ideal Mealtimes: Uses the union of the sets of BG Measurements associated with both the Pre-Meal Bolus and the Ideal Meal Time filters.

All: Uses all the BG measurements within the associated bucket.

None: does not apply a filter.

Figure 7C:
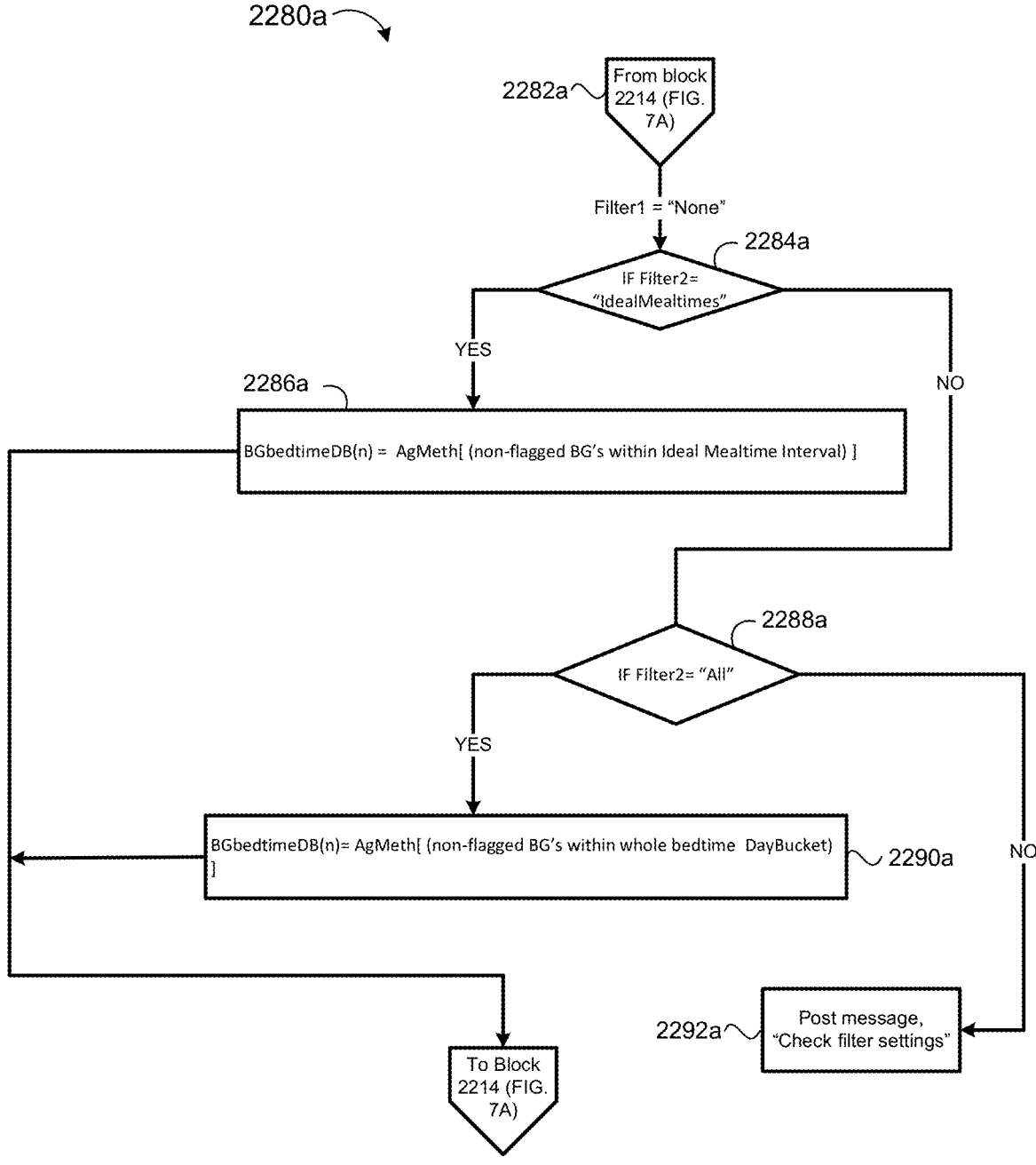
Figure 7D:
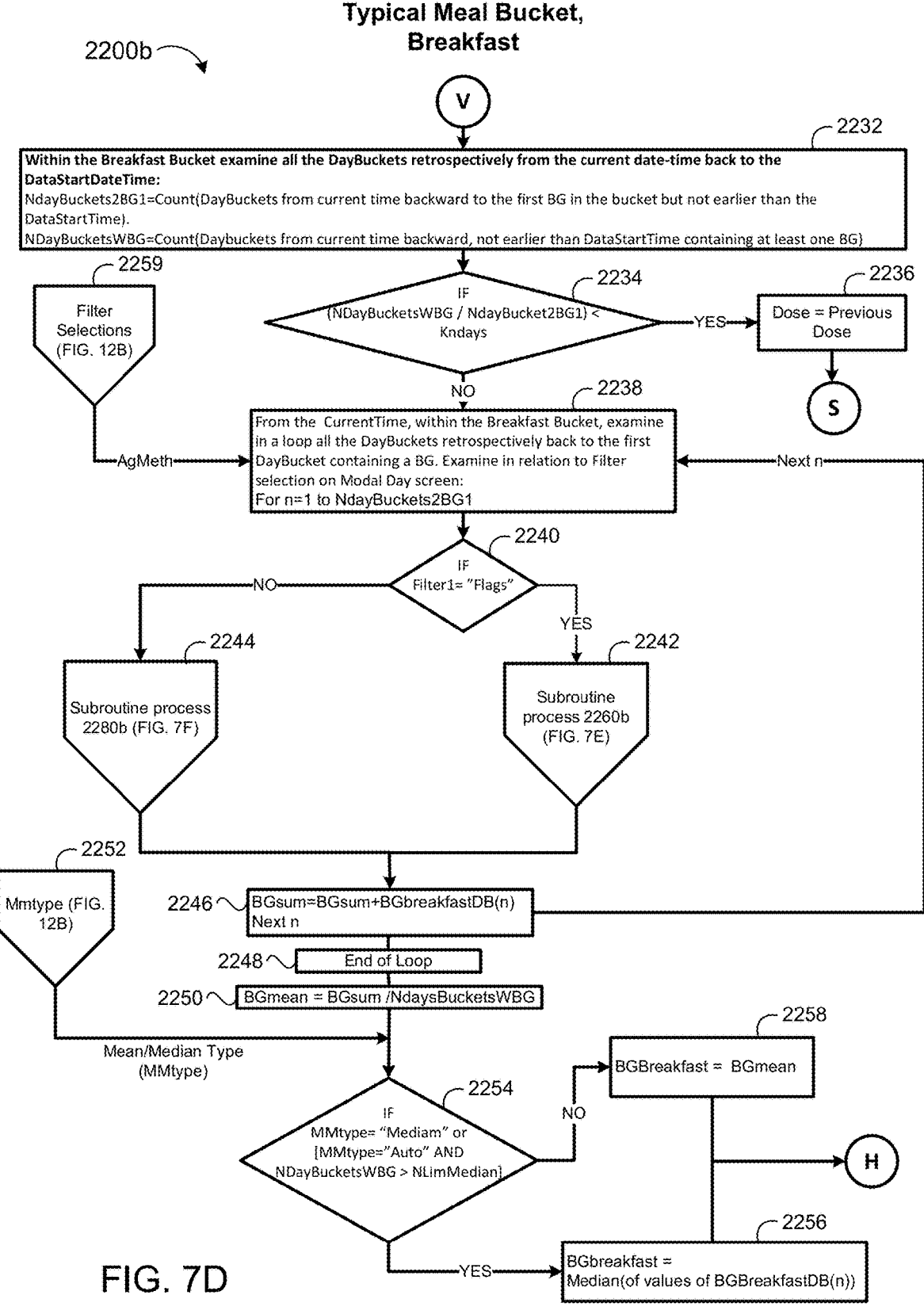

Referring back to FIG. 7A, the aggregation process 2200a for the non-meal BG time-buckets (e.g., MidSleep and Bedtime) executes a loop at block 2208 when block 2204 determines that the ratio of NDayBucketsWBG/NdaysBed-time is greater than or equal to Kndays. Specifically, the aggregation process 2200a examines, at block 2208, all the DayBuckets in the associated time-bucket (e.g., Bedtime BG time-bucket) back to the DataStartDateTime based on the filter selections 512, 514 of the Modal Day Scatter Chart 502 (FIG. 12B) received via block 2230. At block 2210, the aggregation process 2200a examines whether or not Filter1 512 includes "Flags". If the Filter1 512 includes "Flags" (e.g., block 2210 is "YES"), the aggregation process 2200a proceeds to block 2212 for executing subroutine process 2260a (FIG. 7B). On the other hand, if the Filter1 512 does not include "Flags" (e.g., block 2210 is "NO"), the aggre-gation process 2200a proceeds to block 2214 for executing subroutine process 2280a (FIG. 7C). The two subroutine processes 2260a, 2280a aggregate the BG measurements to a single BG value in each associated DayBucket or none if the associated DayBuckets are empty. The outputs determined by the two subroutine processes 2260a, 2280a are provided back to the aggregation process 2200a (FIG. 7A), and at block 2216, the aggregation process 2200a determines a running sum BGsum of the filtered BG measurements. At block 2218, the loop ends and the aggregation process 2200a determines, at block 2220, a mean of the filtered BG measurements BGmean as the sum of the filtered BG measurements (BGsum) divided by the number of DayBuckets with at least one BG inside, (NdayBucketsWBG). In other configurations, the BGmean may be determined by other methods.

The parameter MMtype is associated with a "mean or median type" that controls a choice of the aggregation method applied to the results of the DayBucket aggregations, i.e. mean or median. The Modal Day Scatter Chart 502 (FIG. 12B) may include a selector for choosing the MMtype input to block 2222 for routing to block 2224 of the aggregation process 2200a. At block 2224, the aggregation process 2200a determines if the NDayBucketsWBG (e.g., the number of filtered BG measurements within the associated time-bucket) is greater than a minimum number of BG measurements required for determining a median value (NLimMedian). If the NDayBucketsWBG is greater than the NLimMedian or if the user 40 manually selects "median" as the MMtype (e.g., block 2224 is "YES"), then the aggregation process 2200a proceeds to block 2226 for calculating the BGbedtime using the median value of NDayBucketsWBG within the time-bucket associated with the Bedtime BG time-bucket. If, however, the NDayBucketsWBG is equal to or less than the NLimMedian (e.g., block 2224 is "NO"), then the aggregation process 2200a proceeds to block 2228 for calculating the BGbedtime using the mean value (BGmean) of NDayBucketsWBG within the time-bucket associated with the Bedtime BG time-bucket. Thereafter, the aggregation process 2200a routes the BGbedtime value (or BGMidsleep value) calculated using the median (block 2226) or the BGmean (block 2228) to Entry Point G for use by processes 2300, 2400, 2500 of FIGS. 8, 9, and 10, respectively.

Referring to FIG. 7B, the subroutine process 2260a executes when the aggregation process 2200a (FIG. 7A) determines that the Filter1 512 includes "Flags" (e.g., block 2210 is "YES"). At block 2262a, the subroutine process 2260a provides the determination that Filter1 512 includes "Flags" from block 2212 of the aggregation process (FIG. 7A) to block 2264a, and block 2264a determines whether or not a filter2 514 applies a filter for the associated time-bucket (e.g., Bedtime BG time-bucket). If filter2 514 is not applying any filters to the Bedtime BG time-bucket (e.g., block 2264a is "YES"), then the subroutine process 2260a sets the BG value in the nth DayBucket, BGbedtimeDB(n) equal to the selected aggregate method AgMeth, at block 2266a to all BG measurements flagged "bedtime" in the DayBucket. The subroutine process 2260a routes BGbedtimeDB(n) back to block 2212 of the aggregation process 2200a (FIG. 7A), where each BG measurement representing a DayBucket "n" BGbedtimeDB(n) within the aggregation process 2200a loop is added to a running sum at block 2216 in preparation for calculating the mean.

If, however, block 2264a determines that filter2 514 is applying a filter to the Bedtime BG time-bucket (e.g., block 2264a is "NO"), then the subroutine process 2260a determines, at block 2268a, whether the selected filter applied by filter2 514 includes the "Ideal Mealtimes" filter. If filter 2 514 is applying the "Ideal Mealtimes" filter (e.g., block 2268a is "YES"), then the subroutine process 2260a sets the BG value in the nth DayBucket, BGbedtimeDB(n) equal to the selected aggregate method AgMeth applied, at block 2270a to the union of all BG measurements flagged "bedtime" in the DayBucket together with all non-flagged BG measurements within the Ideal Mealtimes filter. Thereafter, the subroutine process 2260a routes BGbedtimeDB(n) back to block 2212 of the aggregation process 2200a (FIG. 7A), whereby each BG measurement representing a BGbedtimeDB(n) within the aggregation process 2200a loop is added to a running sum at block 2216 in preparation for calculating the mean.

On the other hand, if filter2 514 is not applying the "Ideal Mealtimes" filter (e.g., block 2268a is "NO"), then the subroutine process 2260a determines, at block 2272a, whether the selected filter applied by filter2 514 includes the "All" filter corresponding to the use of all BG measurements within the associated time-bucket (e.g., Bedtime BG time-bucket). When filter2 514 includes the "All" filter (e.g., block 2272a is "YES"), the subroutine process 2260a sets the BG value in the nth DayBucket, BGbedtimeDB(n) equal to the selected aggregate method AgMeth applied at block 2274a to the union of all BG measurements flagged "bedtime" in the DayBucket together with all non-flagged BG measurements within the entire Bedtime DayBucket. Thereafter, the subroutine process 2260a routes the BGbedtimeDB(n) back to block 2212 of the aggregation process 2200a (FIG. 7A), whereby each BG measurement(s) representing the BGbedtimeDB(n) within the aggregation process 2200a loop is added to a running sum at block 2216 in preparation for calculating the mean. The value of BGbedtimeDB(n) routed back to Block 2212 of the aggregation process 2200a from one of blocks 2270a, 2274a fills the nth iteration of the loop. If, however, filter2 514 does not include the "All" filter (e.g., block 2272a is "NO"), then the aggregation process 2200a proceeds to block 2276a and posts message: "Check filter settings" upon the display 116, 146.

Referring to FIG. 7C, the subroutine process 2280a executes when the aggregation process 2200a (FIG. 7A) determines that the Filter1 512 does not include "Flags" (e.g., block 2210 is "NO"). At block 2282a, the subroutine process 2280a provides the determination that Filter1 512 does not include "Flags" from block 2214 of the aggregation process (FIG. 7A) to block 2284a, and block 2284a determines whether or not the selected filter applied by filter2 514 includes the "Ideal Mealtimes" filter. If filter2 514 is applying the "Ideal Mealtimes" filter (e.g., block 2284a is "YES"), then the subroutine process 2280a sets, at block 2286a, the BG value in the nth DayBucket, BGbedtimeDB(n) equal to the selected aggregate method AgMeth applied to all non-flagged BG measurements within the time interval filtered by the Ideal Mealtimes. Thereafter, the subroutine process 2280a routes BGbedtimeDB(n) back to block 2214 of the aggregation process 2200a (FIG. 7A), where each BG measurement representing BGbedtimeDB(n) within the aggregation process 2200a loop is added to a running sum at block 2216 in preparation for calculating the mean.

On the other hand, if filter2 514 is not applying the "Ideal Mealtimes" filter (e.g., block 2284a is "NO"), then the subroutine process 2280a determines, at block 2288a, whether the selected filter applied by filter2 514 includes the "All" filter corresponding to the use of all BG measurements within the associated time-bucket (e.g., Bedtime BG time-bucket). If filter2 514 is applying the "All" filter (e.g., block 2288a is "YES"), then the subroutine process 2280a sets, at block 2290*a*, the BG value in the nth DayBucket, BGbedtimeDB(n) equal to the selected aggregate method AgMeth applied to all non-flagged BG measurements within the "bedtime" DayBucket. Thereafter, the subroutine process 2280*a* routes the BGbedtimeDB(n) back to block 2214 of the aggregation process 2200*a* (FIG. 7A), where each BG measurement(s) representing BGbedtimeDB(n) within the aggregation process 2200*a* loop is added to a running sum at block 2216 in preparation for calculating the mean. The value routed back to Block 2214 of the aggregation process 2200*a* from one of blocks 2286*a*, 2290*a* fills the nth iteration of the loop. If, however, the filter2 514 is not applying the "All" filter (e.g., block 2288*a* is "NO"), then at block 2292*a*, the subroutine process 2280*a* posts message: "Check filter settings" upon the display 116, 146.

Referring to FIG. 7D, the BG aggregation process 2200*b* aggregates the BG measurements of the BG time-buckets (e.g., Breakfast, Lunch, and Dinner) for time intervals when the patient 10 consumes meals. While FIG. 7D shows the BG aggregation process 2200*b* aggregating BG measurements for the Breakfast time-bucket, the BG aggregation process 2200*a* similarly aggregates BG measurements for the Lunch and Dinner BG time-buckets. The aggregation process 2200*b* provides the DataStartDataTime (FIG. 6) via Entry Point V to block 2232 for determining a NdaysBreakfast (or NdaysLunch or NdaysDinner) that counts the number of DayBuckets within the associated bucket (e.g., Breakfast BG time-bucket) from the current date/time backward to an earliest permissible date/time DataStartDateTime. Additionally, the aggregation process 2200*b* determines, at block 2232, an NDayBucketsWBG that counts the number of the DayBuckets containing at least one BG measurement.

At block 2234, the aggregation process 2200*b* determines a ratio of the DayBuckets containing BG measurements to DayBuckets in the associated bucket (e.g., NDayBucketsWBG/NdaysBreakfast) and compares the ratio to a configurable set point (Kndays). The value of Kndays is presently configured at 0.5. If the ratio is less than Kndays, the aggregation process 2200*b* prevents, at block 2236, the dosing controller 160 from adjusting the dose governed by the associated time-bucket (e.g., Breakfast BG time-bucket). For example, when the aggregation process 2200*b* aggregates BG measurements for the Breakfast BG time-bucket, block 2236 prevents the adjustment of the basal dose when the ratio of NDayBucketsWBG/NdaysBreakfast is less than Kndays indicating that the Breakfast BG time-bucket does not contain enough BG measurements. With respect to the Lunch BG time-bucket, block 2236 would prevent the adjustment of the Breakfast meal bolus when the ratio of NDayBucketsWBG/NdaysLunch is less than Kndays. Similarly, when the ratio of NDayBucketsWBG/NdaysDinner is less than Kndays, block 2236 would prevent the adjustment of the Lunch meal bolus. Block 2236 provides the determination that prevents adjusting the dose governed by the associated time-bucket to Entry Point S for use by processes 2300, 2400, 2500 of FIGS. 8, 9, and 10, respectively. On the other hand, if block 2234 determines that the ratio of NDayBucketsWBG/NdaysBreakfast is greater than or equal to Kndays, the dosing controller 160 is permitted to adjust the dose governed by the associated time-bucket.

Figure 7E:
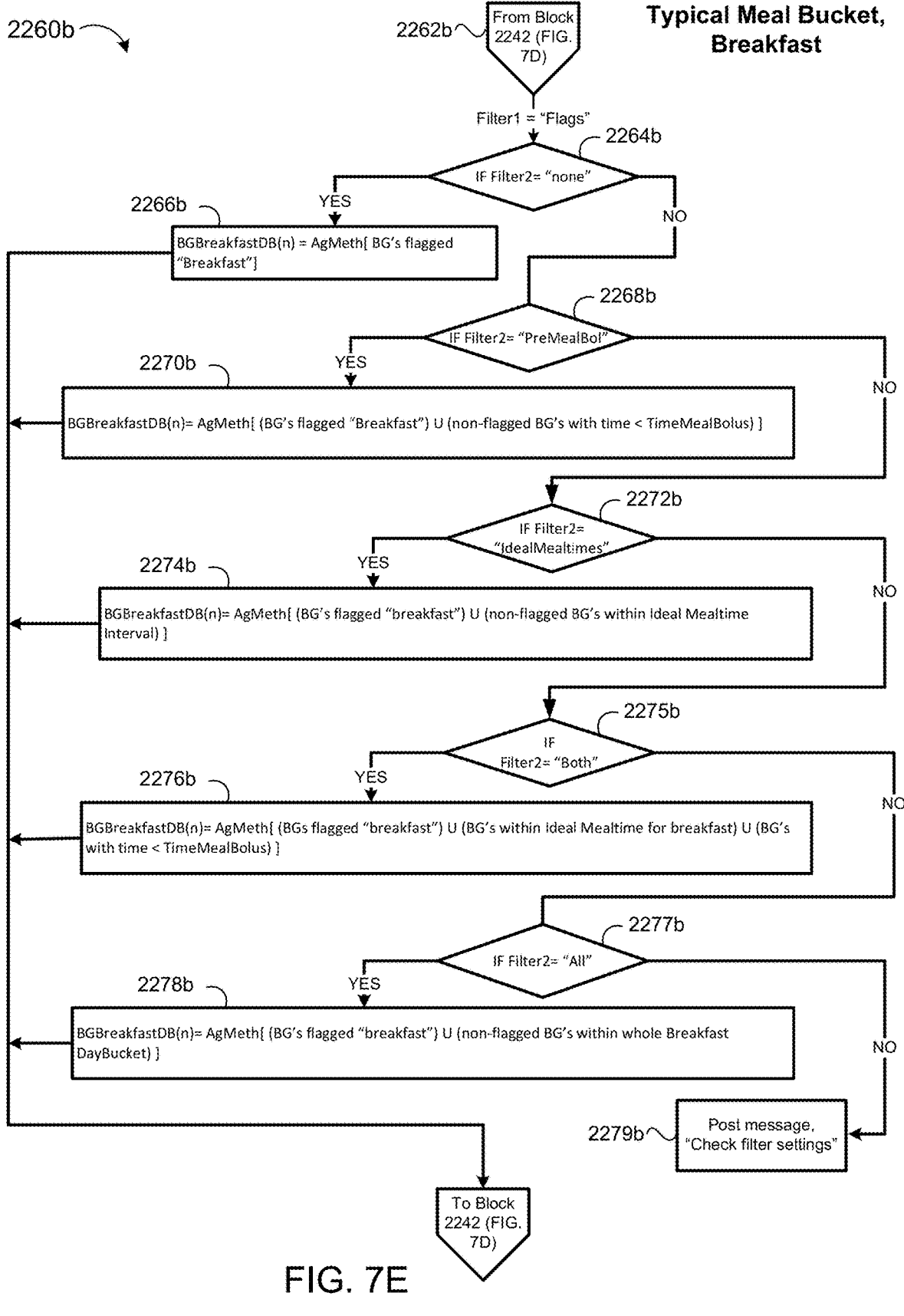

The aggregation process 2200*b* for the meal BG time-buckets (e.g., Breakfast, Lunch, and Dinner) executes a loop at block 2238 when block 2234 determines that the ratio of NDayBucketsWBG/NdaysBreakfast is greater than or equal to Kndays. Specifically, the aggregation process 2200*b* examines, at block 2238, all the DayBuckets in the associated time-bucket (e.g., Breakfast BG time-bucket) back to the DataStartDateTime based on the filter selections 512, 514 of the Modal Day Scatter Chart (FIG. 12B) received via block 2259. At block 2240, the aggregation process 2200*b* examines whether or not Filter1 512 includes "Flags". If the Filter1 512 includes "Flags" (e.g., block 2240 is "YES"), the aggregation process 2200*b* proceeds to block 2242 for executing subroutine process 2260*b* (FIG. 7E). On the other hand, if the Filter1 512 does not include "Flags" (e.g., block 2240 is "NO"), the aggregation process 2200*b* proceeds to block 2244 for executing subroutine process 2280*b* (FIG. 7F). The two subroutine processes 2260*b*, 2280*b* aggregate the BG measurements to a single BG value in each associated DayBucket or none if the associated DayBuckets are empty. The outputs determined by the two subroutine processes 2260*b*, 2280*b* are provided back to the aggregation process 2200*b* (FIG. 7D), and at block 2246, the aggregation process 2200*b* determines a running sum BGsum of the filtered BG measurements. At block 2248, the loop ends and the aggregation process 2200*a* determines, at block 2250, a mean of the filtered BG measurements BGmean as the sum of the filtered BG measurements (BGsum) divided by the number of DayBuckets with at least one BG (NdayBucketsWBG). In other configurations, the BGmean may be determined by other methods.

As set forth above in the aggregation process 2200*a* (FIG. 7A), the parameter MMtype is associated with a "mean or median type" that controls the choice of the aggregation method applied to the results of the DayBucket aggregations, i.e. mean or median. Here, the selector of the Modal Day Scatter Chart 502 (FIG. 12B) chooses the MMtype input to block 2252 for routing to block 2254 of the aggregation process 2200*b*. At block 2254, the aggregation process 2200*b* determines if the NDayBucketsWBG (e.g., the number of filtered BG measurements within the associated time-bucket) is greater than a minimum number of BG measurements required for determining a median value (NLimMedian). If the NDayBucketsWBG is greater than the NLimMedian or if the user 40 manually selects "median" as the MMtype (e.g., block 2254 is "YES"), then the aggregation process 2200*b* proceeds to block 2256 for calculating the BGBreakfast using the median value of NDayBucketsWBG within the time-bucket associated with the Breakfast BG time-bucket. If, however, the NDayBucketsWBG is equal to or less than the NLimMedian (e.g., block 2254 is "NO"), then the aggregation process 2200*b* proceeds to block 2258 for calculating the BGBreakfast using the mean value (BGmean) of NDayBucketsWBG within the time-bucket associated with the Breakfast BG time-bucket. Thereafter, the aggregation process 2200*b* routes the BGBreakfast value (or BGLunch or BGDinner values) calculated using the median (block 2256) or the BGmean (block 2258) to Entry Point H for use by processes 2300, 2400, 2500 of FIGS. 8, 9, and 10, respectively.

Referring to FIG. 7E, the subroutine process 2260*b* executes when the aggregation process 2200*b* (FIG. 7D) determines that the Filter1 512 includes "Flags" (e.g., block 2240 is "YES"). At block 2262*b*, the subroutine process 2260*b* provides the determination that Filter1 512 includes "Flags" from block 2242 of the aggregation process 2200*b* (FIG. 7D) to block 2264*b*, and block 2264*b* determines whether or not a filter2 514 applies a filter for the associated time-bucket (e.g., Breakfast BG time-bucket). If filter2 514 is not applying any filters to the Breakfast BG time-bucket (e.g., block 2264*b* is "YES"), then the subroutine process 2260*b* at block 2266*b*, sets the aggregate value of the BG's in the nth DayBucket of the Breakfast bucket, BGBreakfastDB(n) to the selected aggregate method AgMeth applied to all BG measurements flagged "Breakfast" in the Day-Bucket. The subroutine process 2260b routes BGBreakfastDB(n) back to block 2242 of the aggregation process 2200b (FIG. 7D), where each BG measurement representing DayBucket "n", BGBreakfastDB(n) within the aggregation process 2200b loop is added at block 2246 to a running sum in preparation for calculating a mean.

If, however, block 2264b determines that filter2 514 is applying a filter to the Breakfast BG time-bucket (e.g., block 2264b is "NO"), then the subroutine process 2260b determines, at block 2268b, whether the selected filter applied by filter 2 514 includes the Pre-Meal Bolus "PreMealBol" filter. If filter 2 514 is applying the "Pre-Meal Bolus" filter (e.g., block 2268b is "YES"), then the subroutine process 2260a at block 2270b, sets the aggregate value of the BG's in the nth DayBucket of the Breakfast bucket, BGBreakfastDB(n) to the selected aggregate method AgMeth applied to the union of the set of BG measurements flagged "breakfast" in the DayBucket together with the set of all non-flagged BG measurements having times earlier than a time of the breakfast meal bolus (TimeMealBolus). Thereafter, the subroutine process 2260b routes BGBreakfastDB(n) back to block 2242 of the aggregation process 2200b (FIG. 7D), where each BG measurement representing BGBreakfastDB(n) within the aggregation process 2200b loop is added at block 2246 to a running sum in preparation for calculation of a mean. When the subroutine process 2260b determines, at block 2268b, that filter2 514 is not applying the Pre-Meal Bolus filter (e.g., block 2268b is "NO"), the subroutine process 2260b proceeds to block 2272b.

At block 2272b, the subroutine process 2260b determines whether the selected filter applied by filter2 514 includes the "Ideal Mealtimes" filter. If filter2 514 is applying the "Ideal Mealtimes" filter (e.g., block 2272b is "YES"), then the subroutine process 2260b at block 2274b, sets BGBreakfastDB(n) to the selected aggregate method AgMeth applied to the union of the set of BG measurements flagged "breakfast" in the DayBucket together with the set of non-flagged BG measurements within the Ideal Mealtimes filter for breakfast. Thereafter, the subroutine process 2260b routes BGBreakfastDB(n) back to block 2242 of the aggregation process 2200b (FIG. 7D), where each BG measurement representing BGBreakfastDB(n) within the aggregation process 2200b loop is added at block 2246 to a running sum in preparation for calculation of a mean.

On the other hand, if filter2 514 is not applying the "Ideal Mealtimes" filter (e.g., block 2272b is "NO"), then the subroutine process 2260b determines, at block 2275b, whether the selected filter applied by filter2 514 includes the "Pre-MealBolus OR IdealMealtime" filter, which passes a union of the sets of BG's that meet the Pre-Meal Bolus filter criteria or Ideal Mealtimes filter criteria. If filter2 514 is applying the "Pre-MealBolus OR IdealMealtime" filter (e.g., block 2275b is "YES"), then the subroutine process 2260b, at block 2276b, sets BGBreakfastDB(n) to the selected aggregate method AgMeth applied to the union of the set of BG measurements flagged "breakfast" in the DayBucket together with the set of all non-flagged BG measurements having times earlier than TimeMealBolus for breakfast together with the set of non-flagged BG measurements within the Ideal Mealtime interval for breakfast. Thereafter, the subroutine process 2260b routes BGBreakfastDB(n) back to block 2242 of the aggregation process 2200b (FIG. 7D), where each BG measurement representing BGBreakfastDB(n) within the aggregation process 2200b loop is added at block 2246 to a running sum in preparation for calculation of a mean. When the subroutine process 2260b determines, at block 2275b, that filter2 514 is not applying the "Pre-MealBolus OR IdealMealtime" filter (e.g., block 2275b is "NO"), the subroutine process 2260b proceeds to block 2277b.

At block 2277b, the subroutine process 2260b determines whether the selected filter applied by filter2 514 includes the "All" filter corresponding to the use of all BG measurements within the associated time-bucket (e.g., Breakfast BG time-bucket). At block 2278b, the subroutine process 2260b sets BGBreakfastDB(n) to the the selected aggregate method AGMeth applied to the union of the set of BG measurements flagged "breakfast" in the DayBucket together with the set of all non-flagged BG measurements within the entire Breakfast Daybucket. Thereafter, the subroutine process 2260b routes BGBreakfastDB(n) back to block 2242 of the aggregation process 2200b (FIG. 7D), where each BG measurement representing the BGBreakfastDB(n) within the aggregation process 2200b loop is added at block 2246 to a running sum in preparation to calculation of a mean. The value routed back to Block 2242 of the aggregation process 2200b from one of blocks 2266b, 2270b, 2274b, 2276b, 2278b fills the nth iteration of the loop. If, however, the filter2 514 is not applying the "All" filter (e.g., block 2277b is "NO"), then at block 2279b, the subroutine process 2260b posts message: "Check filter settings" upon the display 116, 146.

Referring to FIG. 7F, the subroutine process 2280b executes when the aggregation process 2200b (FIG. 7D) determines that the Filter1 512 does not include "Flags" (e.g., block 2240 is "NO"). At block 2282b, the subroutine process 2280b provides the determination that Filter1 512 does not include "Flags" from block 2244 of the aggregation process 2200b (FIG. 7D) to block 2284b, and block 2284b determines whether or not the selected filter applied by filter2 514 includes the "Pre-Meal Bolus" filter. If filter 2 514 is applying the "Pre Meal Bolus" filter (e.g., block 2284b is "YES"), then the subroutine process 2280b, at block 2286b, sets BGBreakfastDB(n) to the selected aggregate method AgMeth applied to all BG measurements having times earlier than the time of the associated breakfast meal bolus (TimeMealBolus). Thereafter, the subroutine process 2280b routes BGBreakfastDB(n) back to block 2244 of the aggregation process 2200b (FIG. 7D), where each BG measurement representing BGBreakfastDB(n) within the aggregation process 2200b loop is added at block 2246 to a running sum in preparation for calculating a mean. When the subroutine process 2260b determines, at block 2284b, that filter2 514 is not applying the Pre Meal Bolus filter (e.g., block 2284b is "NO"), the subroutine process 2280b proceeds to block 2288b.

At block 2288b, the subroutine process 2280b determines whether the selected filter applied by filter2 514 includes the "Ideal Mealtimes" filter. If filter2 514 is applying the "Ideal Mealtimes" filter (e.g., block 2288b is "YES"), then the subroutine process 2280b, at block 2290b, sets BGBreakfastDB(n) to the selected aggregate method AgMeth applied to all BG measurements within the Ideal Mealtimes interval (e.g., ideal time filter) for breakfast. Thereafter, the subroutine process 2280b routes BGBreakfastDB(n) back to block 2244 of the aggregation process 2200b (FIG. 7D), where each BG measurement(s) representing BGBreakfastDB(n) within the aggregation process 2200b loop is added at block 2246 to a running sum in preparation for calculating a mean.

On the other hand, if filter2 514 is not applying the "Ideal Mealtimes" filter (e.g., block 2288b is "NO"), then the subroutine process 2280b determines, at block 2292b, whether the selected filter applied by filter2 514 includes the "Pre-MealBolus OR Ideal Mealtimes" filter, which passes the BG's that pass either the Pre Meal Bolus filter or the Ideal Mealtimes filter. If filter2 514 is applying the "Both" filter (e.g., block 2292b is "YES"), then the subroutine process 2280b, at block 2294b, sets BGBreakfastDB(n) to the selected aggregate method AgMeth applied to the union of the set of all BG measurements having times earlier than TimeMealBolus for breakfast together with the set of all BG measurements within the Ideal Mealtime interval for breakfast. Thereafter, the subroutine process 2280b routes BGBreakfastDB(n) back to block 2244 of the aggregation process 2200b (FIG. 7D), where each BG measurement representing BGBreakfastDB(n) within the aggregation process 2200b loop is added at block 2246 to a running sum in preparation for calculating a mean. When the subroutine process 2280b determines, at block 2292b, that filter2 514 is not applying the "Both" filter (e.g., block 2292b is "NO"), the subroutine process 2280b proceeds to block 2296b.

At block 2296b, the subroutine process 2280b determines whether the selected filter applied by filter2 514 includes the "All" filter corresponding to the use of all BG measurements within the associated time-bucket (e.g., Breakfast BG time-bucket). At block 2298b, the subroutine process 2280b sets BGBreakfastDB(n) to the selected aggregate method AGMeth applied to all BG measurements within the entire Breakfast DayBucket. Thereafter, the subroutine process 2280b routes BGBreakfastDB(n) back to block 2244 of the aggregation process 2200b (FIG. 7D), where each BG measurement representing the BGBreakfastDB(n) within the aggregation process 2200b loop is added at block 2246 to a running sum in preparation for calculating a mean. The value routed back to Block 2244 of the aggregation process 2200b from one of blocks 2286b, 2290b, 2294b, 2298b fills the nth iteration of the loop. If, however, the filter2 514 is not applying the "All" filter (e.g., block 2296b is "NO"), then at block 2299b, the subroutine process 2280b posts message: "Check filter settings" upon the display 116, 146.

Figure 8:
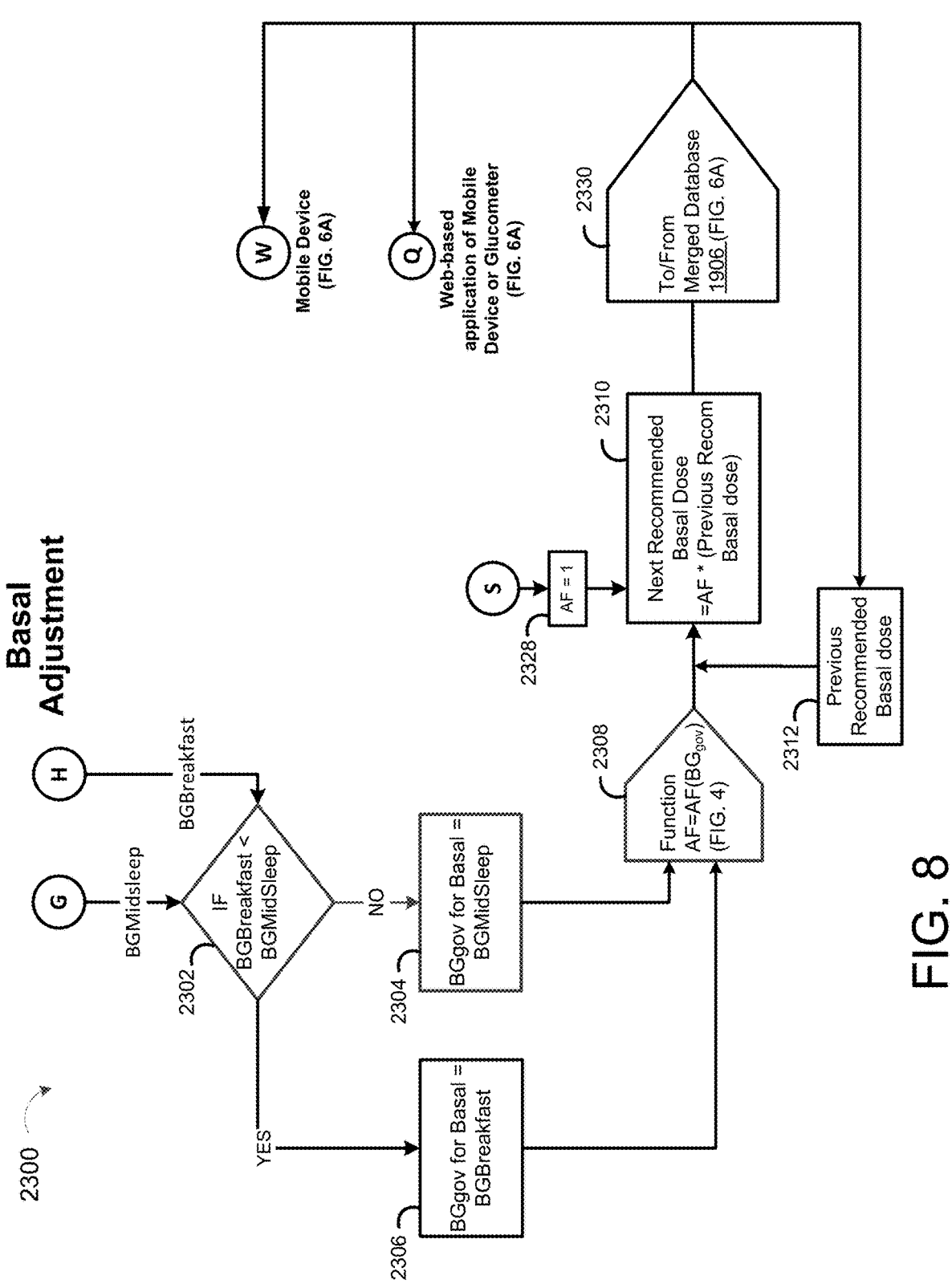
FIG. 8 is a schematic view of an example basal adjustment process
Figure 9:
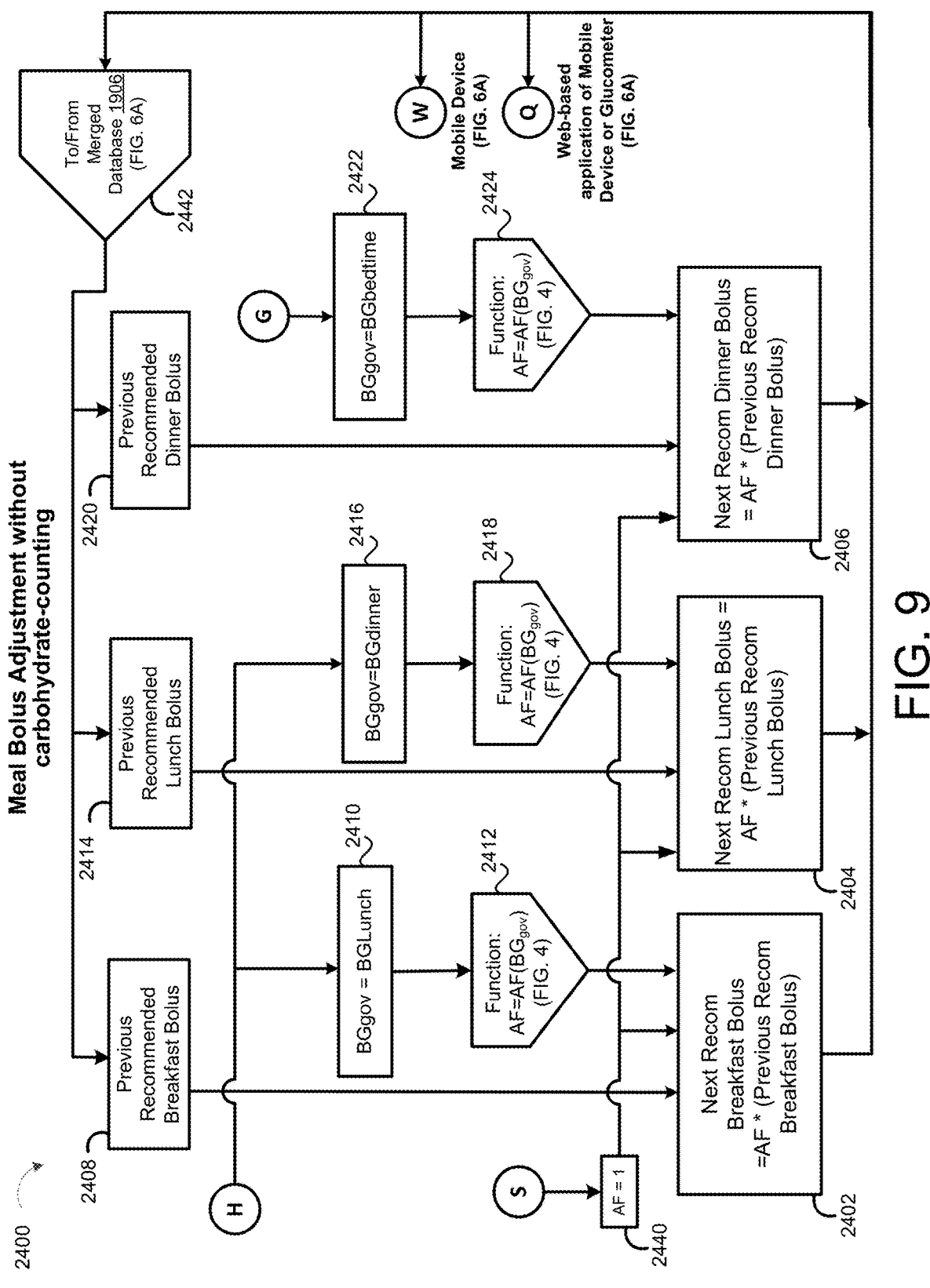
FIG. 9 is a schematic view of an example meal bolus adjustment process.

FIG. 8 shows a basal adjustment process 2300 where block 2302 receives the BGBreakfast from Entry Point H (FIG. 7D) and the BGmidsleep (or from Entry Point G (FIG. 7A). In some implementations, process 2300 determines whether or not the BGBreakfast is less than BGmidsleep. The basal adjustment process 2300, at block 2304, selects the BGbreakfast as the governing blood glucose BGgov for a basal adjustment when BG breakfast is not less than BGmidsleep, and block 2306 selects the BGmidsleep as the governing blood glucose BGgov for the basal adjustment when BG breakfast is less than BGmidsleep. The basal adjustment process 2300 applies an adjustment factor (AF) function (FIG. 4) at block 2308 using the BGgov selected from one of blocks 2304 or 2306. Specifically, the basal adjustment process 2300 determines the adjustment factor AF at block 2308 as a function of the governing blood glucose BGgov. In scenarios when there are an insufficient number of BG measurements for the Midsleep BG time-bucket, i.e., when block 2204 (FIG. 7A) of aggregation processes 2200a is "YES", the basal adjustment process 2300, sets, at block 2328, the Adjustment Factor AF equal to 1. The basal adjustment process 2300 receives, at block 2328, the indication of insufficient BG data, i.e., preventing adjustment of the governing dose, from processes 2200a via Entry Point S. At block 2310, the basal adjustment process 2300 determines the adjustment to the patient's insulin dose by the following equation:

$$RecomBasal=(previous\ RecomBasal)*AF \qquad (12)$$

wherein the previous RecomBasal is provided from block 2312. The basal adjustment process 2300 transmits, at block 2310, the next recommended basal adjustment RecomBasal to the web-based application 198 of the manufacturer of the glucometer 124 or mobile device 110b via Entry Point Q of the SubQ outpatient process 1800 (FIG. 5A or FIG. 5B). In some implementations, the basal adjustment process 2300 uses the data flow process 1900a (FIG. 6A) to transmit the next recommended basal adjustment RecomBasal directly to the mobile device 110b via Entry Point W (FIG. 6A). In other implementations, the basal adjustment process 2300 uses the data flow process 1900a (FIG. 6A) to transmit the next recommended basal adjustment RecomBasal to the web-based application 198 of the mobile device 110b or the glucometer 124 via Entry Point Q (FIG. 6A). Additionally, the basal adjustment process 2300 provides, at block 2330, the RecomBasal to the merged database 1906 (FIG. 6A) within the non-transitory memory 24, 134, 144.

Referring to FIG. 9, a meal bolus adjustment (without carbohydrate-counting) process 2400 shows blocks 2402, 2404, 2406 calculating next recommended meal boluses for scheduled meal boluses of breakfast, lunch, and dinner, respectively. The next recommended meal bolus for each scheduled meal bolus is based on the blood glucose BG measurement that occurs after the meal bolus being adjusted.

For calculating the next recommended breakfast bolus (block 2402), the meal bolus adjustment process 2400 receives, at block 2410, the BG measurement (e.g., BGlunch) that occurs after the breakfast meal bolus via Entry Point H of the aggregation process 2200b (FIG. 7D), and sets the BGlunch as a governing blood glucose BGgov. The meal bolus adjustment process 2400 applies an adjustment factor (AF) function (FIG. 4) at block 2412 using BGlunch as the BGgov. Specifically, the meal bolus adjustment process 2400 determines the adjustment factor AF at block 2412 as function of the governing blood glucose BGgov (e.g., BGlunch). In scenarios when there are an insufficient number of BG measurements for the Lunch BG time-bucket, i.e., when block 2234 (FIG. 7D) of aggregation processes 2200b is "YES", the meal adjustment process 2400, sets, at block 2440, the Adjustment Factor AF equal to 1. The meal bolus adjustment process 2400 receives, at block 2440, the indication of insufficient BG data, i.e., preventing adjustment of the governing dose, from the aggregation process 2200b via Entry Point S. At block 2402, the meal bolus adjustment process 2400 determines the adjustment to the patient's breakfast meal bolus by the following equation:

$$RecomBreakBol=(previous\ RecomBreakBol)*AF \qquad (15A)$$

wherein the previous RecomBreakBol is provided from block 2408. Block 2408 may obtain the previous RecomBreakBol from block 2442 associated with the merged database 1906 (FIG. 6A) within the non-transitory memory 24, 134, 144. Thereafter, the meal bolus adjustment process 2400 uses the data flow process 1900a (FIG. 6A) to transmit the next recommended breakfast bolus to the web-based application 198 of the mobile device 110b or the glucometer 124 via Entry Point Q (FIG. 6A), or directly to the mobile device 110b via Entry Point W (FIG. 6A).

For calculating the next recommended lunch bolus (block 2404), the meal bolus adjustment process 2400 receives, at block 2416, the BG measurement (e.g., BGdinner) that occurs after the lunch meal bolus via Entry Point H of the aggregation process 2200b (FIG. 7D), and sets the BGdinner as a governing blood glucose BGgov. The meal bolus adjustment process 2400 applies an adjustment factor (AF) function (FIG. 4) at block 2418 using BGdinner as the BGgov. Specifically, the meal bolus adjustment process 2400 determines the adjustment factor AF at block 2418 as a function of the governing blood glucose BGgov (e.g., BGdinner). In scenarios when there are an insufficient number of BG measurements for the Dinner BG time-bucket, i.e., when block 2234 (FIG. 7D) of aggregation processes 2200b is "YES", the meal adjustment process 2400, sets, at block 2440, the Adjustment Factor AF equal to 1. The meal bolus adjustment process 2400 receives, at block 2440, the indication of insufficient BG data, i.e., preventing adjustment of the governing dose, from the aggregation process 2200b via Entry Point S. At block 2404, the meal bolus adjustment process 2400 determines the adjustment to the patient's lunch meal bolus by the following equation:

$$\text{RecomLunchBol} = (\text{previous RecomLunchBol}) * \text{AF} \tag{15B}$$

wherein the previous RecomLunchBol is provided from block 2414. Block 2414 may obtain the previous RecomLunchBol from block 2442 associated with the merged database 1906 (FIG. 6A) within the non-transitory memory 24, 134, 144. Thereafter, the meal bolus adjustment process 2400 uses the data flow process 1900a (FIG. 6A) to transmit the next recommended lunch bolus to the web-based application 198 of the mobile device 110b or the glucometer 124 via Entry Point Q (FIG. 6A), or directly to the mobile device 110b via Entry Point W (FIG. 6A).

For calculating the next recommended dinner bolus (block 2406), the meal bolus adjustment process 2400 receives, at block 2422, the blood glucose (BG) measurement (e.g., BGbedtime) that occurs after the dinner meal bolus via Entry Point G of the non-meal aggregation process 2200a (FIG. 7A), and sets BGbedtime as a governing blood glucose BGgov. The meal bolus adjustment process 2400 applies an adjustment factor (AF) function (FIG. 4) at block 2424 using BGbedtime as the BGgov. Specifically, the meal bolus adjustment process 2400 determines the adjustment factor AF at block 2424 as a function of the governing blood glucose BGgov (e.g., BGbedtime). In scenarios when there are an insufficient number of BG measurements for the Bedtime BG time-bucket, i.e., when block 2204 (FIG. 7A) of aggregation process 2200a is "YES", the meal bolus adjustment process 2400, sets, at block 2440, the Adjustment Factor AF equal to 1. The meal bolus adjustment process 2400 receives, at block 2440, the indication of insufficient BG data, i.e., preventing adjustment of the governing dose, from the aggregation process 2200a via Entry Point S. At block 2406, the meal bolus adjustment process 2400 determines the adjustment to the patient's next dinner meal bolus by the following equation:

$$\text{RecomDinnerBol} = (\text{previous RecomDinnerBol}) * \text{AF}, \tag{15C}$$

wherein the previous RecomDinnerBol is provided from block 2420. Block 2420 may obtain the previous RecomDinnerBol from block 2442 associated with the merged database 1906 (FIG. 6A) within the non-transitory memory 24, 134, 144. Thereafter, the meal bolus adjustment process 2400 uses the data flow process 1900a (FIG. 6A) to transmit the next recommended dinner bolus to the web-based application 198 of the mobile device 110b or the glucometer 124 via Entry Point Q (FIG. 6A), or directly to the mobile device 110b via Entry Point W (FIG. 6A).

In some implementations, the adjusted meal boluses set forth above may be calculated using the grams of carbohydrate consumed by the patient 10 and the Carbohydrate-to-Insulin Ratio CIR where the Recommended Breakfast, Lunch and Dinner Boluses may be calculated as follows:

$$\text{RecomLunchBolus} = (\text{Carbohydrate gms in Lunch})/\text{CIR} \tag{16A}$$

$$\text{RecomDinnerBol} = (\text{Carbohydrate gms in Dinner})/\text{CIR} \tag{16B}$$

$$\text{RecBreakfastBol} = (\text{Carbohydrate gms in Breakfast})/\text{CIR} \tag{16C}$$

Referring to FIG. 10, a carbohydrate-insulin-ratio (CIR) adjustment process 2500 shows blocks 2502, 2504, 2506 calculating next recommended CIRs for scheduled meal boluses of breakfast, lunch and dinner, respectively. The next recommended CIR for each scheduled meal bolus is based on the blood glucose BG measurement that occurs after the meal bolus associated with the CIR being adjusted.

For calculating the next recommended breakfast CIR (block 2502), the CIR adjustment process 2500 receives, at block 2510, the BG measurement (e.g., BGlunch) that occurs after the breakfast meal bolus via Entry Point H of the aggregation process 2200b (FIG. 7D), and sets the BGlunch as a governing blood glucose BGgov. The CIR adjustment process 2500 applies an adjustment factor (AF) function (FIG. 4) at block 2512 using BGlunch as the BGgov. Specifically, CIR adjustment process 2500 determines the adjustment factor AF at block 2512 as a function of the governing blood glucose BGgov (e.g., BGlunch). In scenarios when there are an insufficient number of BG measurements for the Lunch BG time-bucket, i.e., when block 2234 (FIG. 7D) of aggregation processes 2200b is "YES", the CIR adjustment process 2500, sets, at block 2540, the Adjustment Factor AF equal to 1. The CIR adjustment process 2500 receives, at block 2540, the indication of insufficient BG data, i.e., preventing adjustment of the governing dose, from the aggregation process 2200b via Entry Point S. At block 2502, the CIR adjustment process 2500 determines the adjustment to the patient's breakfast CIR by the following equation:

$$\text{RecomBreakCIR} = (\text{previous RecomBreakCIR})/\text{AF}, \tag{17A}$$

wherein the previous RecomBreakCIR is provided from block 2508. Block 2508 may obtain the previous RecomBreakCIR from block 2542 associated with the merged database 1906 (FIG. 6A) within the non-transitory memory 24, 134, 144. Thereafter, the CIR adjustment process 2500 uses the data flow process 1900a (FIG. 6A) to transmit the next recommended breakfast CIR to the web-based application 198 of the mobile device 110b or the glucometer 124 via Entry Point Q (FIG. 6A), or directly to the mobile device 110b via Entry Point W (FIG. 6A).

For calculating the next recommended lunch CIR (block 2504), the CIR adjustment process 2500 receives, at block 2516, the BG measurement (e.g., BGdinner) that occurs after the lunch meal bolus via Entry Point H of the aggregation process 2200b (FIG. 7D), and sets the BGdinner as a governing blood glucose BGgov. The CIR adjustment process 2500 applies an adjustment factor (AF) function (FIG. 4) at block 2518 using BGdinner as the BGgov. Specifically, the CIR adjustment process 2500 determines the adjustment factor AF at block 2518 as a function of the governing blood glucose BGgov (e.g., BGdinner). In scenarios when there are an insufficient number of BG measurements for the Dinner BG time-bucket, i.e., when block 2234 (FIG. 7D) of aggregation processes 2200b is "YES", the CIR adjustment process 2500, sets, at block 2540, the Adjustment Factor AF equal to 1. The CIR adjustment process 2500 receives, at block 2540, the indication of insufficient BG data, i.e., preventing adjustment of the governing dose, from the aggregation process 2200b via Entry Point S. At block 2504, the CIR adjustment process 2500 determines the adjustment to the patient's lunch CIR by the following equation:

$$\text{RecomLunchCIR}=(\text{previous RecomLunchCIR})/\text{AF}, \qquad (17\text{B})$$

wherein the previous RecomLunchCIR is provided from block 2514. Block 2514 may obtain the previous RecomLunchCIR from block 2542 associated with the merged database 1906 (FIG. 6A) within the non-transitory memory 24, 134, 144. Thereafter, the CIR adjustment process 2500 uses the data flow process 1900a (FIG. 6A) to transmit the next recommended breakfastCIR to the web-based application 198 of the mobile device 110b or the glucometer 124 via Entry Point Q (FIG. 6A), or directly to the mobile device 110b via Entry Point W (FIG. 6A).

For calculating the next recommended CIR dinner bolus (block 2506), the CIR adjustment process 2500 receives, at block 2522, the blood glucose (BG) measurement (e.g., BGbedtime) that occurs after the dinner meal bolus via Entry Point G of the non-meal aggregation process 2200a (FIG. 7A), and sets BGbedtime as a governing blood glucose BGgov. The CIR adjustment process 2500 applies an adjustment factor (AF) function (FIG. 4) at block 2524 using BGbedtime as the BGgov. Specifically, the CIR adjustment process 2500 determines the adjustment factor AF at block 2524 as a function of the governing blood glucose BGgov (e.g., BGbedtime). In scenarios when there are an insufficient number of BG measurements for the Bedtime BG time-bucket, i.e., when block 2204 (FIG. 7A) of aggregation process 2200a is "YES", the CIR adjustment process 2500, sets, at block 2540, the Adjustment Factor AF equal to 1. The CIR adjustment process 2500 receives, at block 2540, the indication of insufficient BG data, i.e., preventing adjustment of the governing dose, from the aggregation process 2200a via Entry Point S. At block 2506, the CIR adjustment process 2500 determines the adjustment to the patient's next dinner CIR by the following equation:

$$\text{RecomDinnerCIR}=(\text{previous RecomDinnerCIR})/\text{AF} \qquad (17\text{C})$$

wherein the previous RecomDinnerCIR is provided from block 2520. Block 2520 may obtain the previous RecomDinnerCIR from block 2542 associated with the merged database 1906 (FIG. 6A) within the non-transitory memory 24, 134, 144. Thereafter, the CIR adjustment process 2500 uses the data flow process 1900a (FIG. 6A) to transmit the next recommended dinner CIR to the web-based application 198 of the mobile device 110b or the glucometer 124 via Entry Point Q (FIG. 6A), or directly to the mobile device 110b via Entry Point W (FIG. 6A).

Figure 11:
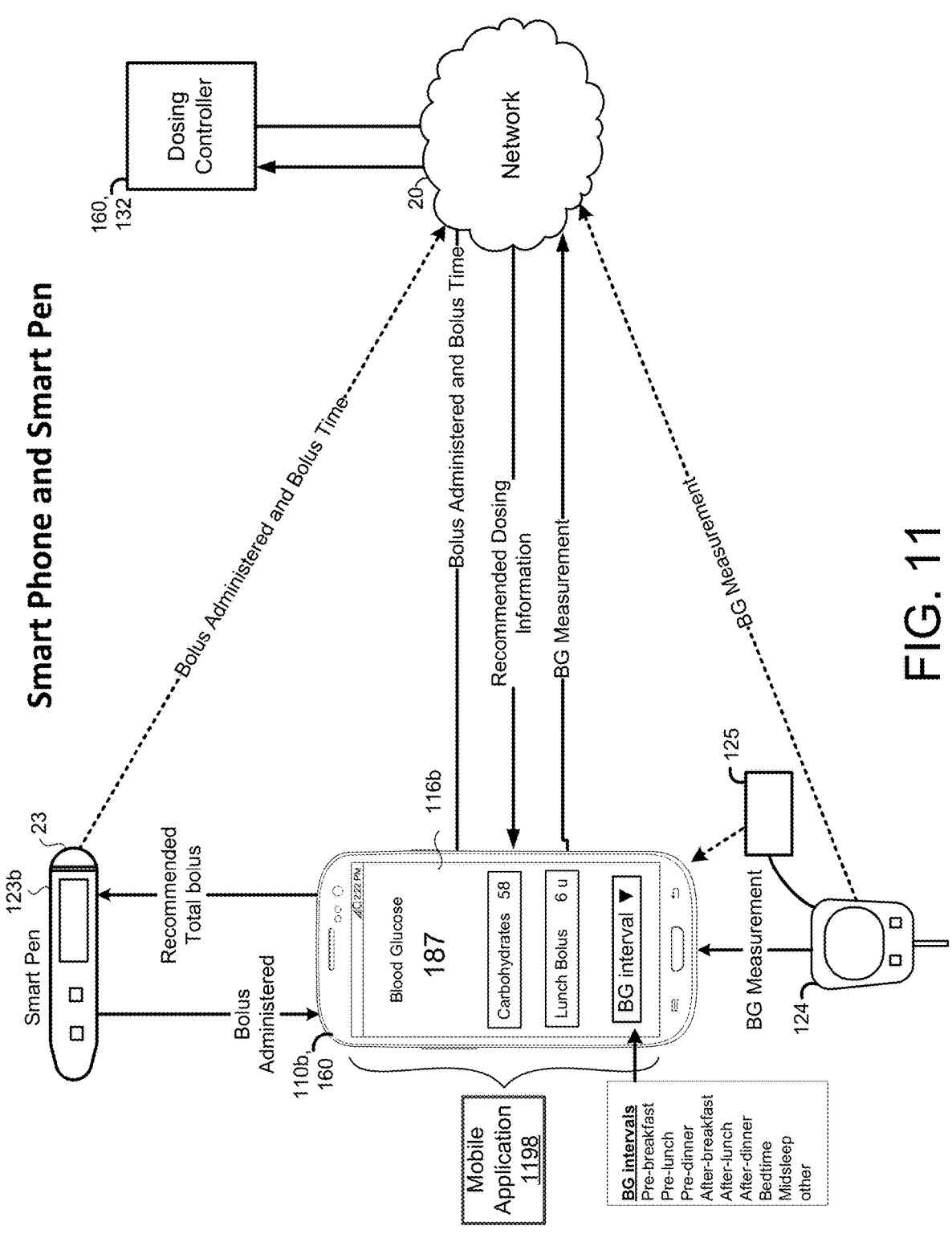
FIG. 11 is a schematic view of example components of the system of FIGS. 1A-1C.

FIG. 11 is a schematic view of exemplary components of the system of FIGS. 1A-1C. FIG. 11 may be described with reference to the SubQ outpatient process 1800b of FIG. 5B. In some implementations, the insulin administration device 123 associated with the patient 10 includes a smart pump 123a or a smart pen 123b that is capable of communicating (e.g., syncing) with a patient device 110 such as a smart phone 110b. In the example shown, the smart pen 123b communicates with the smart phone 110b via Bluetooth, however, other wireless or wired communications are possible. The smart pen 123b may include an associated smart pen cap 23 that removably attaches to the smart pen 123b to enclose and protect the doser 223b when not being used to administer insulin. The cap 23 may be removed from the pen 123b to expose the doser 223b when the patient 10 is administering insulin. In some implementations, the smart pen cap 23 implements some or all of the functionality of the smart pen 123b. For instance, the smart pen cap 23 may include the processor 112e, the non-transitory memory 114e, and/or the display 116e instead of the smart pen 123b, or the pen 123b and cap 23 may each implement at least one of the processor 112e, the non-transitory memory 114e, and/or display 116. Accordingly, the smart pen cap 23 may communicate with the patient device 110 (e.g., smart phone 110b) via Bluetooth or through other wireless or wired communications. Likewise, in some implementations, the glucometer 124 associated with the patient 10 is capable of communicating blood glucose measurements to the smart phone 110b. The glucometer 124 and smart phone 110b may communicate via Bluetooth, infrared, cable, or any other communications. In some examples, the glucometer 124 communicates with a data translator 125, and the data translator 125 provides the blood glucose measurements from the glucometer 124 to the smart phone 110b. The computing device 112b of the smart phone 110b may execute a mobile application 1198 for communicating with the dosing controller 160 such that information can be communicated over the network 20 between the dosing controller 160 and each of the smart pen 123b (and/or cap 23) and the glucometer 124. For example, dosing parameters (recommended dosing information) adjusted by the dosing controller 160 may be transmitted to the smart phone 110b and stored within memory 114b (FIG. 1B). The dosing parameters may include, but are not limited to: TargetBG, Correction Factor (CF), CIR for all day, CIR's for each meal, Remaining Insulin $I_{Rem}$, Recommended Breakfast Bolus, Recommended Lunch Bolus, Recommended Dinner Bolus, Recommended Basal doses, number of Basal doses per day, and Basal dose scheduled times. As described above with reference to the data flow process 1900a-c of FIGS. 6A-6C, the dosing parameters may be adjusted automatically or manually initiated by the user 40 or patient 10.

In some implementations, upon the glucometer 124 determining a blood glucose measurement, the glucometer 124 transmits the blood glucose measurement to the smart phone 110b. The smart phone 110b may render the blood glucose measurement upon the display 116b and permit the patient 10 to select the BGtype associated with the blood glucose measurement (e.g., blocks 1804 and 1806 of FIG. 5B). The BGtype or BG Interval corresponds to a label or tag chosen by the patient 10 from a dropdown list upon the display 116b of the smart phone 110b. Alternatively, the patient 10 may select the BG Interval from a dropdown list displayed on the display 116c of the glucometer. The smart phone 110b may transmit the BG measurement and the BG type to the dosing controller 160 via the network 20. In some examples, the glucometer 124 is configured to transmit the BG measurement and/or BG type directly to the dosing controller 160 via the network 20. In some implementations, the mobile application 1198 executing on the smart phone 110b calculates a correction bolus (CB) using EQ. 2 based upon the current correction factor (CF) and Target BG stored within the memory 114b. In other implementations, the correction bolus (CB) is calculated using EQ. 10 (block 714 of FIG. 3) by deducting from previously administered doses of insulin that are still active. The CF and Target BG may be provided when a previous dosing parameter adjustment was transmitted to the smart phone 110b from the dosing controller 160.

In some implementations, recommended meal boluses may be determined by the dosing controller 160 and sent to the smart phone 110b during each adjustment transmission and stored within the memory 114b. For example, upon the patient 10 selecting the BG type for a given blood glucose measurement, the mobile application 1198 executing on the smartphone may determine the meal bolus (e.g., breakfast, lunch, or dinner) based upon the BG type without using carb counting for the current meal. In some configurations, the mobile application 1198 executing on the smart phone 110*b* executes all functionality of the dosing controller 160, thereby eliminating the need for communications over the network. For instance, the processor 112*b* and non-transitory memory 114*b* of the smart phone 110*b* may execute the mobile application 1198 with full functionality of the dosing controller 160 to allow the smart phone 110*b*, the smart pen 123*b*, and the glucometer 124 to function autonomously when a network connection is unavailable. Here, the mobile application 1198 may set time limits for the autonomous usage to allow for backup, billing, and/or checking-in with the HCP 40.

In some examples, when the BG measurement requires the correction bolus, the mobile application 1198 calculates a total bolus (e.g., meal bolus+correction bolus) and transmits the total bolus to the smart pen 123*b*. In some implementations, the meal bolus corresponds to a previously calculated meal bolus that the mobile application 1198 waits to transmit to the smart pen 123*b* until the appropriate dosage time. The total bolus may also include a calculated basal dose for the patient. In some configurations, the patient 10 includes a separate smart pen 123*b* for the basal dose due to the basal dose corresponding to a different insulin type (long-acting) than the insulin type (fast acting) associated with the recommended meal and correction doses. In these configurations, the mobile application 1198 may send the appropriate number of doses of insulin to each of the smart pens 123*b*. In some examples, the smart pen 123*b* (using the administration computing device 112*e*) automatically dials in the total bolus for the doser 223*b* to administer. In some examples, the smart pen 123*b* receives a recommended total bolus dose from the smart phone 110*b* transmitted from the computing device 142 of the dosing controller 160 via the network 20. The patient 10 may interact with the smart pen 123*b* (or cap 23) to accept the recommended insulin dose displayed upon the display 116*e* or manually change the recommended insulin dose. The doser 223*b* of the smart pen 123*b* may include an electro-mechanical stop that actuates a plunger to only administer the recommended dosage of insulin accepted by the patient 10 or dosage of insulin manually entered by the patient 10. In some examples, upon administration of an insulin dose by the smart pen 123*b*, the smart pen 123*b* transmits the value of the administered dose and the time of the administered dose to the smart phone 110*b* for storage within memory 114*b* along with the associated BG measurement. Additionally, the smart phone 110*b* may transmit the bolus administered and the time of the administered dose to the dosing controller 160 via the network 20. In some configurations, the smart pen 123*b* (or cap 23) forms a direct communication link with the dosing controller 160 via the network 20 for receiving the recommended dosing information and/or transmitting the administered dose and the time of the administered dose to the dosing controller 160.

In some examples, the patient 10 may enter a number of carbohydrates for a current meal into the glucometer 124 for transmission to the smart phone 110*b* or directly into the smart phone 110*b* when a blood glucose measurement is received. For instance, upon receiving the blood glucose measurement from the glucometer 124, the smart phone 110*b* may render an interactive graphic upon the display 116*b* that enables the patient to enter the number of carbohydrate grams the patient 10 plans to ingest. Using a carbohydrate-to-insulin ratio (CIR) transmitted from the dosing controller 160 to the smart phone 110*b*, the mobile application 1198 executing on the smart phone 110*b* may calculate the recommended meal bolus (e.g., breakfast, lunch or dinner) using one of the EQ. 16A-16C. In some examples, the CIR and CF are adjusted each time a BG measurement is received at the dosing controller 160 from the glucometer 124 using the smart phone 110*b* to facilitate the transmission thru the network 20. In other examples, the CIR and CF are adjusted when all the dosing parameters are adjusted (e.g., via the batch download process) and transmitted to the smart phone 110*b* for storage within the memory 114*b*.

FIG. 12A shows the display 146 of the health care provider computing system 140 displaying blood glucose data. A plot 502 depicts a modal day scatter chart of blood glucose measurements over a period of time along the x-axis and blood glucose value along the y-axis. In the example shown, a target blood glucose range is depicted in the plot. Computational Information 504 depicts an average for patients' A1C value (6.8%), an average fasting blood glucose value (e.g., 138 mg/dl), an average BGs per day, a percent of BGs Within the target, a total number of patients using basal bolus therapy, a total number of patients using basal/correction therapy, a total number of patients using a pump, and a total number of patients using inhalants. Bar graph 506 depicts a distribution of blood glucose measurements in the target range and pie chart 508 depicts a percentage of patients experiencing varying degrees of hypoglycemia.

FIG. 13 is a schematic view of an exemplary Carbohydrate-Insulin-Ratio (CIR) Adjustment in a Meal-by-Meal process 2600. There is a single variable for CIR. Blocks 2604, 2608, 2610, 2614, 2616 determine whether or not a given meal type is associated with a BGtype for Breakfast, Lunch, Dinner, Bedtime, or MidSleep/Miscellaneous, respectively. For a given meal, e.g. Lunch, the process obtains the CIR, at block 2628 from the previous meal calculations e.g. Breakfast, associated with block 2624 (a few hours previous). The current BG is identified as the Lunch BG at block 2608. The Lunch BG may be only seconds old. The Lunch BG is sent to block 2618 as a governing blood glucose value BGgov for determining an Adjustment Factor AF using the Adjustment Factor Function. Accordingly, at block 2628, the process 2600 calculates the CIR for Lunch by dividing the previous CIR for Breakfast by the AF determined at block 2618. Block 2628 provides the CIR for Lunch to block 2640 for calculating the recommended lunch bolus by dividing an estimated number of carbohydrates to be consumed by the patient by the CIR for lunch. For calculating the CIR for Dinner, block 2632 may use the CIR for Lunch calculated at block 2628. Process 2600 repeats, meal-by-meal, with the exception of the logic flow between Bedtime and Breakfast, whereat the Bedtime BG is ideally placed after Dinner to govern an adjustment to the current CIR. Therefore, the Bedtime BG at block 2614 is the governing BG fed to the AF function at block 2622, and the resulting AF is sent to block 2634. Also the current CIR arrives at 2634 from the CIR for Dinner calculated at block 2632. The calculation at block 2634 involves dividing the current CIR by the AF to obtain a newly adjusted value of the CIR. In some implementations, a Bedtime snack is allowed, using this value of the CTR. This value of the CIR (governed by the Bedtime BG) is passed without further adjustment to the Breakfast calculations the next day. In some implementations, an additional CIR adjustment may be governed by the MidSleep BG.

Figure 14:
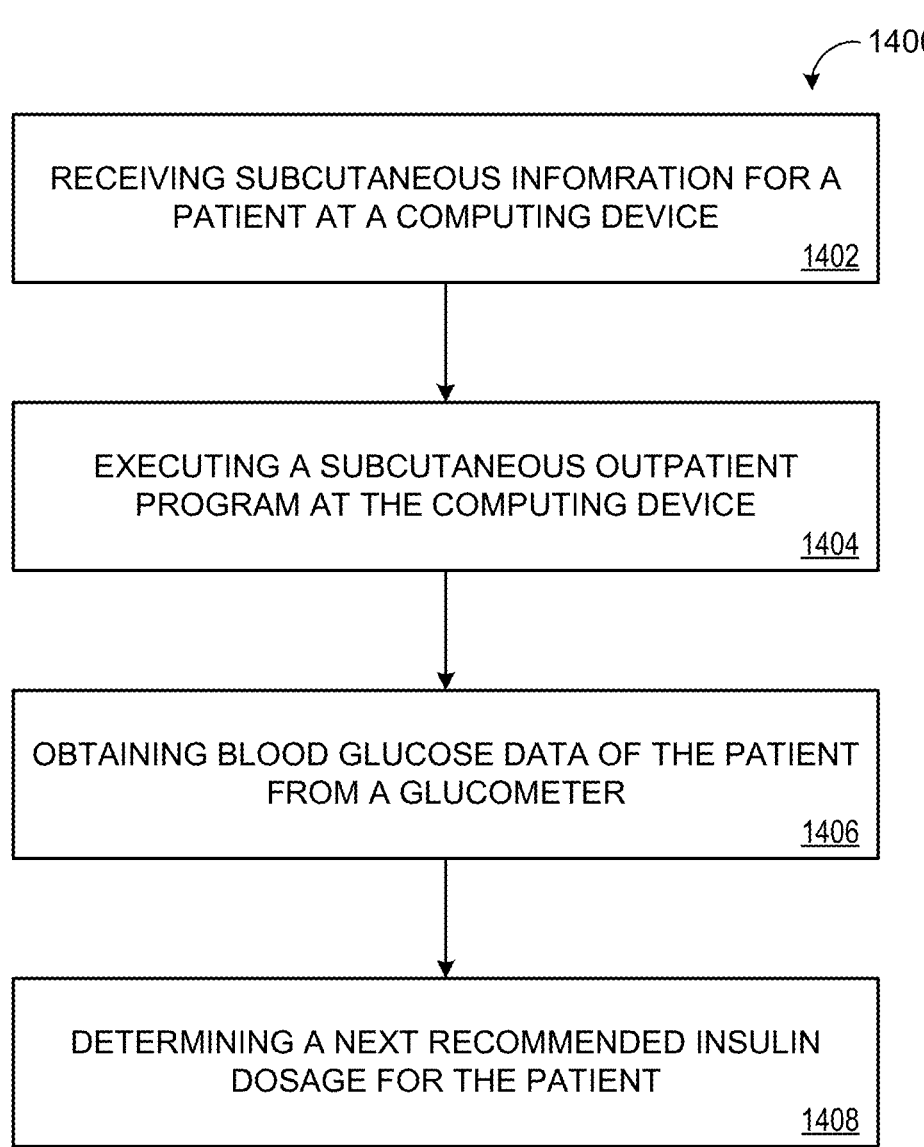
FIG. 14 is an exemplary arrangement of operations for administering insulin.

Referring to FIG. 14, a method 1400 of administering insulin using a subcutaneous (SubQ) outpatient process 1800 includes receiving 1402 subcutaneous information 216 for a patient 10 at a computing device 112, 132, 142. The method 1400 executes 1404 the SubQ outpatient process 1800. The method 1400 includes obtaining 1406 blood glucose data of the patient 124 from a glucometer 124 in communication with the computing device 112, 132, 142. The blood glucose data includes blood glucose measurements of the patient 10 and/or doses of insulin administered by the patient 10 associated with each blood glucose measurement. The method 1400 includes the computing device 112, 132, 142 determining 1408 a next recommended insulin dosage for the patient 10 based on the obtained blood glucose data and the subcutaneous information 216*a*. The method further includes 1400 the computing device 112, 132, 142 transmitting the next recommended insulin dosage to a portable device associated with the patient 10. The portable device 110*a-e* displays the next recommended insulin dose.

In some implementations, a BG filtering process 1500 (FIG. 15) includes a collection of filters 1600 (FIG. 15) for identifying BG measurements for use by a BG aggregation process 1700 (FIG. 17A) in determining a best aggregate BG value to represent an associated time-bucket. In these implementations, the BG aggregation process 1700 is used instead of the aggregation process 2200*a*, 2200*b* of FIGS. 7A-7F. Accordingly, the BG aggregation process 1700 may rely on a more robust set of BG measurements for determining aggregate BG values for each of the time-buckets through the use of multiple filters 1600 that accurately differentiate between BG measurements that are usable for use in adjusting doses of insulin versus BG measurements that are unusable. The BG filtering process 1500 uses the tag chosen by the patient 10 for each BG measurement. For instance, the tag may be selected using the glucometer (e.g., block 1806 of FIGS. 5A and 5B) or a dropdown list upon the display 116*b* of the smart phone 110*b*. The tag, i.e., meter tag, may include a format based on the brand of the glucometer or other device, and therefore may require translation into a standard format (StandardTag). Standard-Tags may be associated with time-buckets, such as pre-breakfast, pre-lunch, pre-dinner, bedtime and midsleep, and may be collectively referred to as "Usable", and may be referred to as "Usable Standard Tags" or "Usable BG measurements". A StandardTag corresponding to a given BG measurement may change several times as the BG measurement proceeds through the collection of filters 1600. Accordingly, any BG measurements remaining after the filters are complete will be associated with Usable Standard-Tags for use by the BG aggregation process 1700 (FIG. 17A) in determining a best aggregate BG value to represent the associated time-bucket. A redundant system assigns a Boolean value to a parameter (Use) 1508 associated with these BG's. Thus Use=1 also signifies that the BG aggregation process 1700 will use corresponding BG measurement in determining the best aggregate BG value.

Referring to FIG. 2I, in some examples, a BG Update Interval input screen on the display 116, 146 permits the user 40 (or patient 10) to limit the number of BG measurements included in an update, define acceptable margins for including BG measurements within a designated BG time-bucket, and set calendar-intervals for updating the BG measurements. The BG Update Interval input screen allows the user 40 to input MaxDays information 360 to limit the number of BG measurements by setting the MaxDays into the past that are allowed in the update. In some examples, the number of MaxDays is configured for 28 days. The BG Update Interval input screen also allows the user 40 to input BG Time-Bucket margins (BucketMargin) 362 that permit a BG measurement having a time that is outside of a time interval associated with a given bucket to still be included in that bucket. For instance, the user 40 may input the BucketMargin 362 for each bucket such that if a BG is outside of the corresponding bucket, but within the BucketMargin 362, the BG will be included within the bucket. For instance, the BucketMargin 362 allows for a flag or tag-corrector that permits a given BG measurement outside of a Lunch bucket, but within the acceptable time defined by the BucketMargin 362, to be included within the BG time-bucket for pre-Lunch. In some examples, the BucketMargin 362 is equal to 2 hours. The user 40 may also input one or more standard update intervals 364 using the BG Update Interval input screen on the display 116, 146. In some implementations, the BG Update Interval input screen allows the user 40 to input the configurable set point (Kndays) 366 to a positive value less than one. Generally, the Kndays defines a minimum allowable fraction of (number of Daybucket Aggregates in the associated time-bucket)/(number of DayBuckets since the earliest BG in the associated time-bucket). Here, the number of DayBuckets since the earliest BG may refer to a number of "available" DayBuckets since the start of the data included in the bucket. In some examples, Kndays is equal to 0.5.

Figure 15:
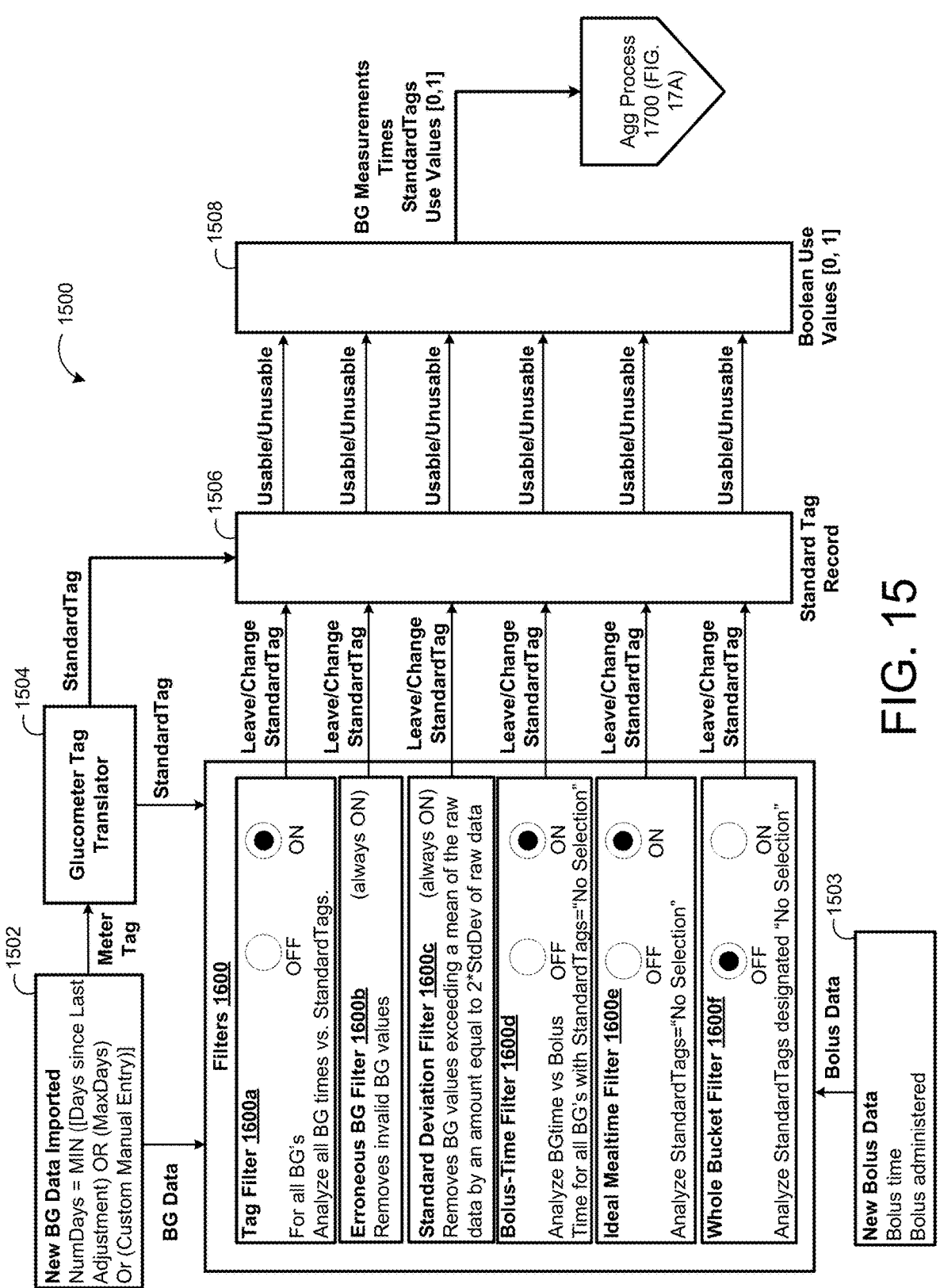
FIG. 15 is a schematic view of an example blood glucose filtering process for identifying past blood glucose measurements for use in determining aggregate blood glucose values.

Referring to FIG. 15, the BG filtering process 1500 uses the collection of filters 1600, 1600*a-e* to filter out BG data for use by the BG aggregation process 1700 in determining the best aggregate BG value to represent an associated time-bucket. The dosing controller 160 may execute the BG filtering process 1500 and the patient device 110 may execute the functionality of the dosing controller 160 thereon. At block 1502, the BG filtering process 1500 imports new BG data. For instance, the process 1500 may receive BG data during a batch download process directly from the memory 114*c* of the glucometer 124 or from the web-based application 198 of the manufacturer of the glucometer 124, as described above in the data flow process 1900*a* of FIG. 6A. The BG data may include BG measurements, date-times associated with the BG measurements, and/or meter tags assigned to the BG measurements by the patient 10. For instance, the patient 10 may select the meter tag for each BG measurement from the dropdown list displayed on one of the portable devices 110, 124 (e.g., block 1806 of FIG. 5B or the dropdown list upon the display 116*b* of the smart phone 110*b* FIG. 11). In some examples, the glucometer 124 automatically tags each BG measurement based on a time (BGtime) of the BG measurement. At block 1503, the BG filtering process 1500 imports new bolus data. For instance, the process 1500 may receive bolus data including a dose of an administered bolus and a time of the administered bolus from the administration device 123 (e.g., smart pen 123*b*) directly or by way of the user device 110 (e.g., smart phone 110*b*), as described above with reference to FIG. 11.

The newly imported BG data may be associated with a date-range from the current date-time to a DataStartDate-Time that includes the lesser one of the number of days since a last adjustment ('Days since Last Adjustment'), MaxDays (e.g., a recommended value of 28 days), or a Custom Manual entry of the DataStartDateTime input by the user 40 (e.g., HCP 40). The MaxDays includes a date-time into the past from the current date-time and may include a configurable constant input as MaxDays information 360 by the user 40 via the BG Update Interval input screen of FIG. 2I. The user 40 may also use a Custom Manual entry to provide a DataStartDateTime. As used herein, the Days since Last Adjustment refers to a number of days since a last dosing adjustment and/or a number of days since the BG data was last imported.

The meter tags associated with the BG measurements and selected by the patient 10 may be different depending upon the manufacturer of the glucometer 124. For instance, a "pre-Lunch" tag field and a "Before Lunch" tag field may refer to the same BGtype or StandardTag. Accordingly, after importing the BG data at block 1502, the BG filtering process 1500 sends the meter tag to block 1504, and applies a meter tag translator (also referred to as a glucometer tag translator) to convert the meter tag included in the imported BG data into a standard tag format (StandardTag). In some examples, tags of the StandardTag format include Before Breakfast, Before Lunch, Before Dinner, Bedtime, Midsleep, No Selection, Other, and Invalid. In these examples, the Before Breakfast, Before Lunch, Before Dinner, Bedtime, and Midsleep tags are collectively referred to as and correspond to usable StandardTags, i.e., each is associated with a corresponding time-bucket. The StandardTag can be changed more than once and may serve as a record of the status of each BG measurement as it proceeds through the filter sequence. The StandardTags for each BG measurement of the imported BG data is input to both the collection of filters 1600 and a StandardTag record 1506 that saves each StandardTag and BG measurement pair from the imported BG data.

The collection of filters 1600 receives the imported BG data from block 1502 and the StandardTags applied by the glucometer tag translator from block 1504. The collection of filters 1600 includes, but is not limited to, a Tag filter 1600a, an Erroneous BG filter 1600b, a Standard Deviation filter 1600c, a Bolus-Time filter 1600d, an Ideal Mealtime filter 1600e, and a Whole Bucket filter 1600f. Referring to FIG. 2J, in some examples, a BG Filtering and Aggregation Options input screen on the display 116, 146 permits the user 40 (or patient 10) to enable or disable specific ones of the filters 1600, select a DayBucket Aggregation Method, and select a Bucket Aggregation method. For instance, a filter selector 370 allows the user 40 to enable/disable corresponding ones of the Tag filter 1600a, the Bolus-time filter 1600d, the Ideal Mealtime filter 1600e, and the Whole Bucket filter 1600f in ON/OFF states. The erroneous BG filter 1600b and the Standard Deviation filter 1600c may be automatically enabled in the ON state without the option for disablement. When the user 40 (or patient 10) enables the Bolus-time filter 1600d in the ON state, the Bolus-time filter 1600d may detect a meal bolus time (TimeMealBolus) in the Daybucket associated with the scheduled blood glucose time interval of the corresponding BG measurement. Conversely, disabling the Bolus-time filter 1600d in the OFF state results in the corresponding BG measurement passing on to which ever one of the Ideal-Mealtime filter 1600e or the Whole-Bucket filter 1600f is enabled by the user 40 in the ON state. Thus, the user 40 enabling one of the Ideal Mealtime and Whole Bucket filters 1600e, 1600f in the ON state, causes the BG filter process 1500 to automatically disable the other one of the filters 1600e, 1600f in the OFF state. FIG. 2J shows the Tag filter 1600a, the Bolus-Time filter 1600d, and the Ideal Mealtime filter 1600e enabled in the ON state via an input by the user 40.

For aggregating DayBuckets, a DayBucket Aggregation Method selector 372 allows the user 40 to select one of a Minimum of filtered BG measurements in the DayBucket, an Earliest of filtered BG measurements in a DayBucket, a Mean of filtered BG measurements in the DayBucket, or a Median of filtered BG measurements in the DayBucket. FIG. 2J shows the Minimum of filtered BG measurements selected via an input by the user 40. Moreover, for aggregating Buckets, a Bucket Aggregation Method selector 374 allows the user 40 to select one of a Mean of DayBucket Aggregates for the associated time-bucket, a Median of DayBucket Aggregates for the associated time-bucket, or an Automatic Mean or Median of DayBucket Aggregates for the associated time-bucket. In some examples, the Median of DayBucket Aggregates is not available when the update interval selected is the three-day update interval (e.g., via the standard update intervals 364 of the input screen of FIG. 2I). The Median of DayBucket Aggregates may not be available when the three-day update interval does not contain enough data for an accurate determination of the median. In some configurations, the Bucket Aggregation Method selector 374 allows the user 40 to select whether or not the selected Bucket Aggregation Method will use a Fewest & Lowest Aggregation that aggregates based on the minimum required number of DayBucket Aggregates that increments upward from a DayBucket Aggregate having a lowest value. FIG. 2J shows the Automatic Mean or Median of DayBucket Aggregates selected as the Bucket Aggregation Method for use by the aggregation process 1700 of FIG. 17A.

In some implementations, for selecting a value of the meal bolus time (TimeMealBolus) for use by the Bolus-time filter 1600d, a TimeMealBolus selector 376 allows the user 40 to select the value of TimeMealBolus as either a time of an earliest bolus in the associated DayBucket or a time of a largest bolus in the associated DayBucket. Selection of the earliest bolus may correspond to a Boolean parameter (BolTimeType) having a value equal to zero while selection of the largest bolus may correspond to the BolTimeType having a value equal to one. The BolTimeType is provided to the Bolus Time Filter 1600d of FIG. 16D. Alternatively, the BolTimeType may be provided to the TimeMealBolus selection process 300 FIG. 2K.

Figure 2K:
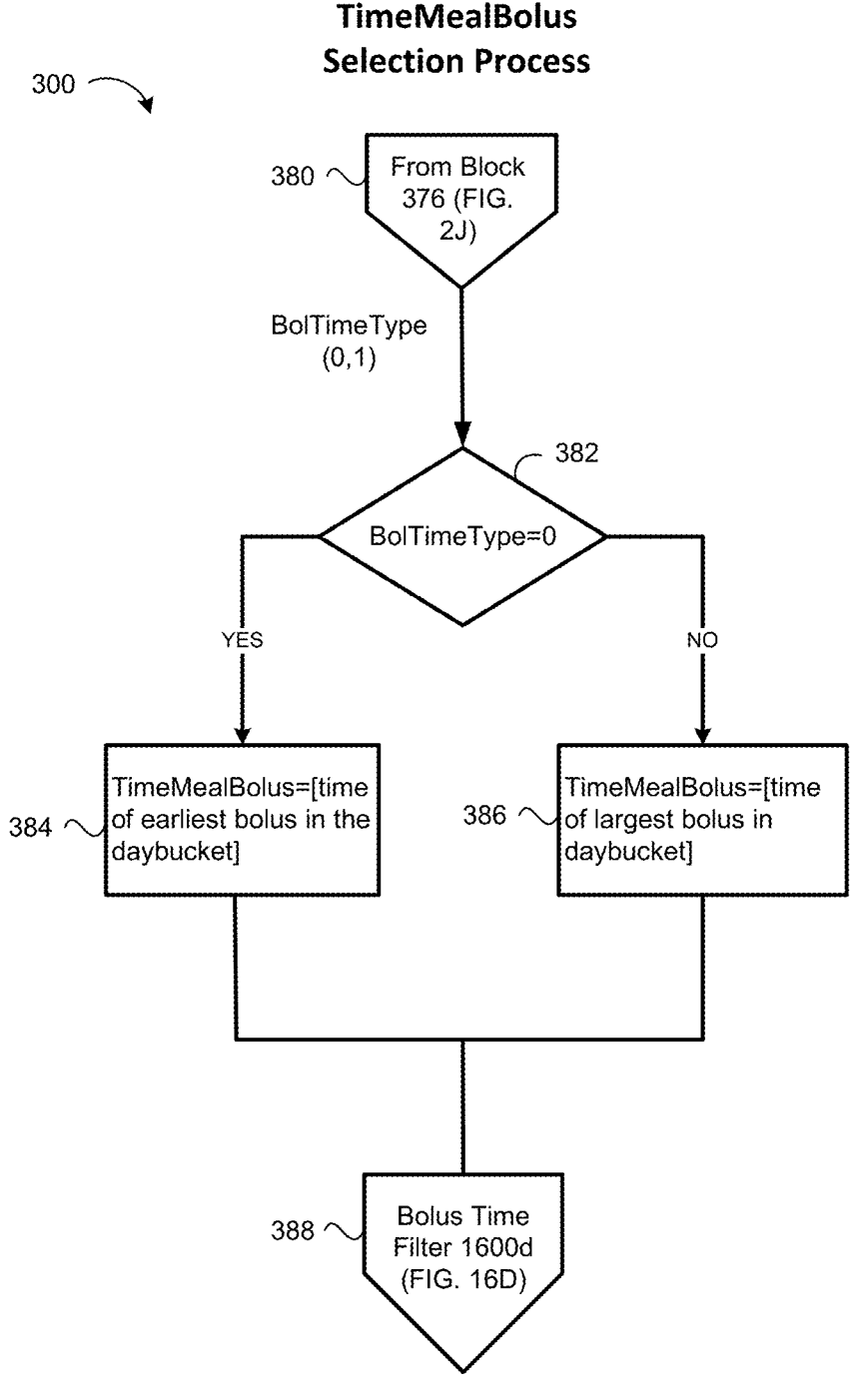
FIG. 2K is a schematic view of an example meal bolus time selection process.

Referring to FIG. 2K, a meal bolus time (TimeMealBolus) selection process 300 receives, at block 380, the selection by the user 40 from the TimeMealBolus selector 376 of FIG. 2J having a value of the BolTimeType equal to zero or one, and at decision block 382, determines whether or not the value of BolTimeType is equal to zero. When the BolTimeType is equal to zero (i.e., decision block 382 is "YES"), the TimeMealBolus selection process 300 sets, at block 384, the TimeMealBolus to the value equal to the time of the earliest meal bolus in the associated DayBucket. On the other hand, when the BolTimeType is equal to one (i.e., decision block 382 is "NO"), the TimeMealBolus selection process 300 sets, at block 386, the TimeMealBolus to the value equal to the time of the largest meal bolus in the associated Day-Bucket. At block 388, the TimeMealBolus selection process 300 provides the value for the TimeMealBolus set by one of blocks 384, 386 to the Bolus-time filter 1600d of FIG. 16D.

Referring back to FIG. 15, the collection of filters 1600 includes the Tag filter 1600a, the Bolus-Time filter 1600d, and the Ideal Mealtime filter 1600e enabled in the ON state, and the Whole Bucket filter 1600f disabled in the OFF state. The Erroneous BG filter 1600b and the Standard Deviation filter 1600c are always enabled in the ON state to filter out erroneous BG measurements as well as BG measurements exceeding a mean of raw data (e.g., imported BG measurements) by an amount equal to two times a standard deviation of the raw data. For each BG measurement contained in the imported BG data, each filter 1600a-f (when enabled in the ON state) is operative to one of leave the StandardTag input to the StandardTag Record 1506 unchanged or change the StandardTag input to the StandardTag Record 1506. Once the filtering of the BG measurements by the filters 1600 enabled in the ON state is complete, the Standard Tag Record 1506 of the BG filtering process 1500 may include StandardTags deemed usable or unusable. For instance, the StandardTag Record may include multiple StandardTags changed by one or more of the filters 1600 since the beginning of the BG filtering process 1500, whereby some of the StandardTags will be usable StandardTags (e.g., associated with buckets). A Boolean operator 1508 may assign a Boolean parameter (Use) as Use=1 to each usable StandardTag in the StandardTag Record 1506. Designating/ identifying a StandardTag as usable and assigning the Boolean parameter Use=1 provides redundancy to the BG filtering process 1500 for selecting a corresponding BG measurement from the imported BG data for use by Aggregation Process 1700 of FIG. 17A. After the filters have run, the BG filtering process 1500 sends all the BG measurements associated with Usable StandardTags and Boolean parameter (Use) as Use=1 to the Aggregation Process 1700 of FIG. 17A. In other configurations, the BG filtering process 1500 completes first, and then the Boolean parameter Use=1 is applied to all remaining BG measurements with Usable StandardTags. In the example shown, all of the filters 1600 run in order, with each filter 1600 examining all of the imported BG measurements. In some implementations, the Tag filter 1600a is required to run first by examining all of the imported BG measurements and the Erroneous BG filter 1600b runs second while any of the remaining filters 1600c-1600f may run in any order. In these implementations, each of the remaining filters 1600c-1600f may analyze the BG measurements on an individual basis or all of the BG measurements may filter through one filter 1600c-1600f and the next filter may filter out the remaining BG measurements.

Figure 16A:
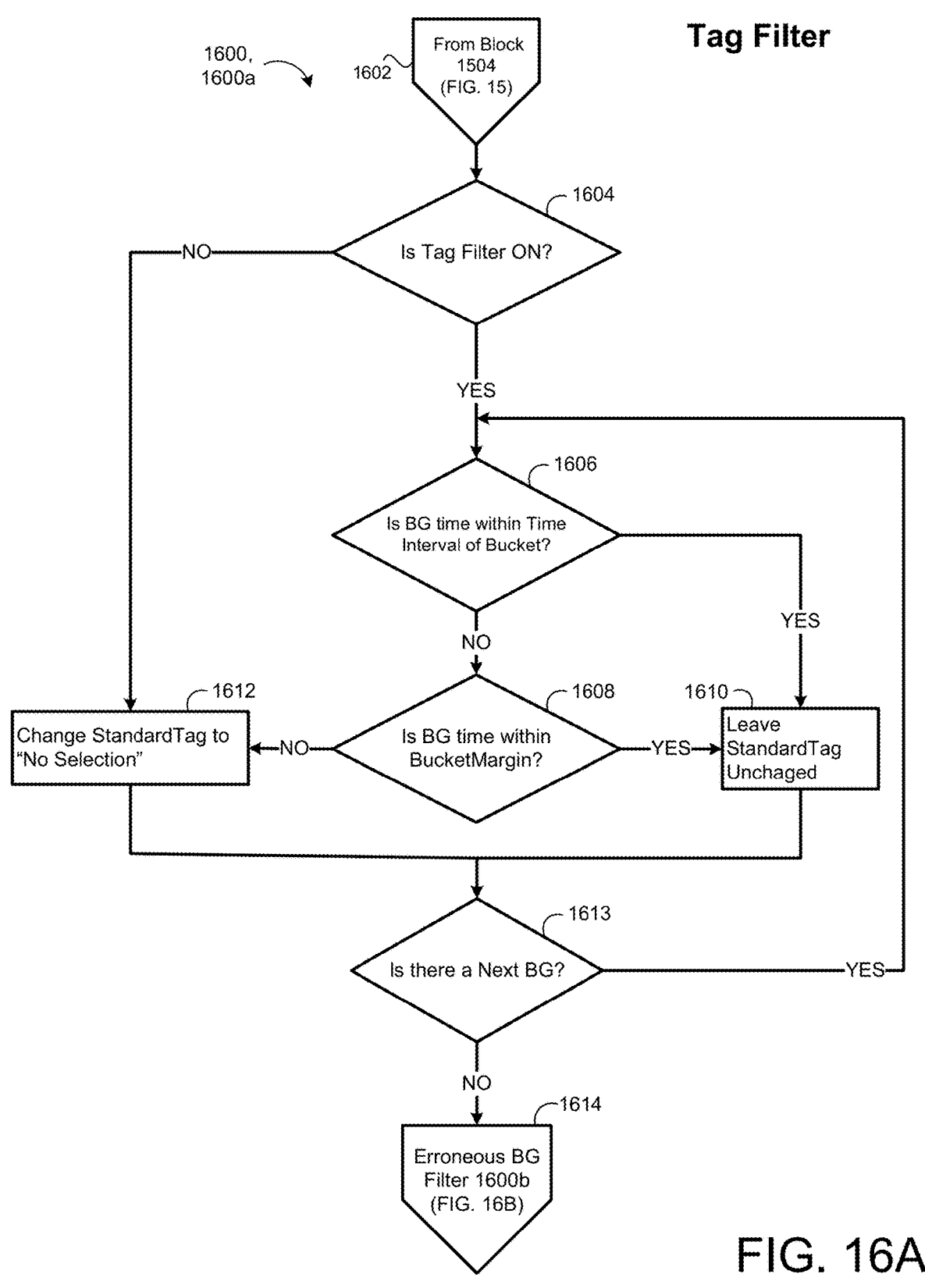

Referring to FIG. 16A, the Tag filter 1600a receives, at block 1602, each usable StandardTag from block 1504 of the BG filtering process 1500 and determines, at decision block 1604, whether or not the tag filter is ON. The usable StandardTags collectively refer to, or designate, the Before Breakfast, Before Lunch, Before Dinner, Bedtime, and Midsleep StandardTags. If the tag filter is OFF, i.e., decision block 1604 is "NO", then the tag filter 1600a proceeds to block 1612 and changes all of the StandardTags to "No Selection". Advantageously, it may be desirable to disable the tag filter 1600a in the OFF state when analyzing the BG data for a poorly-compliant patient 10 whose StandardTag selection is inaccurate and results in noise. By disabling the tag filter 1600a, the noise is removed and a determination of the tag is left to one or more of the other filters 1600b-f.

Conversely, if decision block 1604 determines the tag filter is ON, i.e., decision block 1604 is "YES", then the tag filter 1600a proceeds to decision block 1606 and determines if the BG time associated with each StandardTag is within a time interval of the associated time-bucket for one of Before Breakfast, Before Lunch, Before Dinner, Bedtime, and Midsleep. To put another away, decision block 1606 is determining whether or not the StandardTag associated with each BG measurement includes a usable StandardTag. As used herein, a usable StandardTag collectively refers to a StandardTag belonging to time-buckets for Before Breakfast, Before Lunch, Before Dinner, Bedtime, and Midsleep. If decision block 1606 determines the BGtime associated with the StandardTag is within the associated time interval of the associated bucket, i.e., decision block 1606 is "YES", then the tag filter 1600a proceeds to block 1610 and leaves the applied StandardTag unchanged. Thus, the StandardTag associated with the BG measurement is a usable Standard-Tag when decision block 1606 is "YES".

However, if decision block 1606 determines the BGtime associated with the StandardTag is outside the time interval, i.e., decision block 1606 is "NO", then the tag filter 1600a proceeds to decision block 1608 and determines if the BGtime associated with the StandardTag is within the Buck-etMargin for the given bucket. Here, the BucketMargin may include a value (e.g., 2 hours) input to the BG Update Interval input screen of FIG. 2I by the user 40 that permits a BG measurement having a StandardTag with a time that is outside of the time interval of the associated bucket to still be included in that bucket. Accordingly, if decision block 1608 determines the time of the StandardTag is within the BucketMargin, i.e., decision block 1608 is "YES", then the tag filter 1600 proceeds to block 1610 and leaves the applied StandardTag unchanged. Otherwise, the tag filter 1600a proceeds to block 1612 and changes the StandardTag to "No Selection" since the time of the StandardTag is outside the time interval of the associated time-bucket by an amount greater than the BucketMargin.

After the Tag Filter 1600a analyzes each usable Standard-Tag and either leaves the StandardTag unchanged (block 1610) or changes the StandardTag to "No Selection" (block 1612), the tag filter 1600a determines, at decision block 1613, if there is a Next BG measurement (e.g., a second BG measurement). If there is a next BG measurement, i.e., decision block 1613 is "YES", then the tag filter 1600a reverts back to decision block 1606 to determine if the BGtime associated with the Next BG measurement is within the time interval of the associated time-bucket. After analyzing each BG measurement, the tag filter 1600a exits to the Erroneous BG filter 1600b of FIG. 16B at block 1614.

Figure 16B:
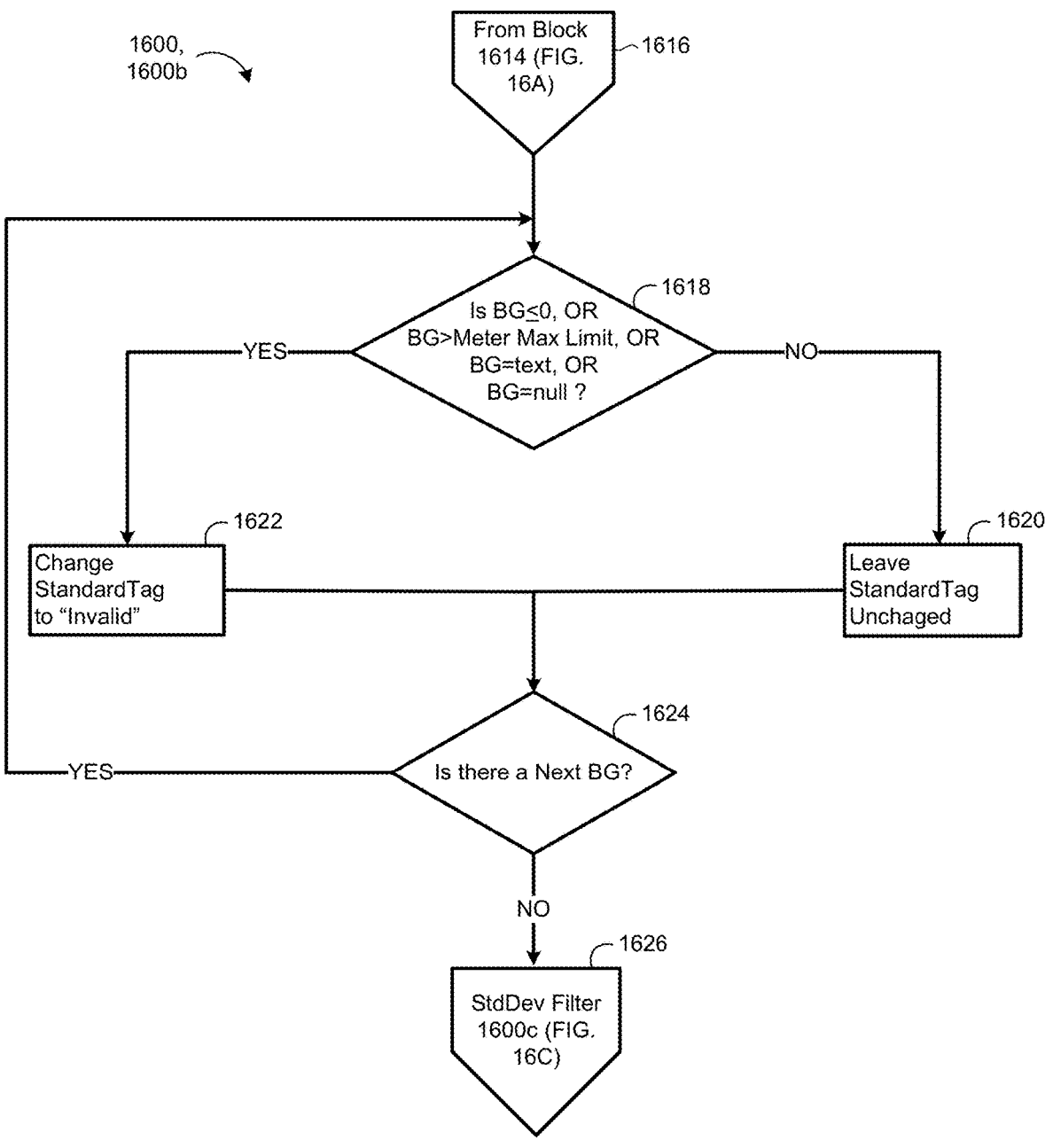

Referring to FIG. 16B, the Erroneous BG filter 1600b commences at block 1616 after completion of the tag filter 1600a at block 1614 of FIG. 16A, and analyzes each BG measurement imported to the BG filtering process 1500 at block 1502 of FIG. 15 to determine whether each corresponding BG measurement is valid or invalid. For a first BG measurement, the Erroneous BG filter 1600b determines, at decision block 1618, whether the BG measurement corresponds to one of a numerical value less than or equal to zero, a numerical value greater than or equal to a maximum limit (Max Limit) for the glucometer 124, a null, or text. If the first BG measurement is a positive integer less than the Max Limit, i.e., decision block 1618 is a "NO", the Erroneous BG filter 1600b proceeds to block 1620 and leaves the Stan-dardTag associated with the first BG measurement unchanged. Accordingly, the Erroneous BG filter 1600b determines that a BG measurement is valid when decision block 1618 is a "NO".

On the other hand, if the first BG measurement is text, a negative integer, a null, or a positive integer greater than or equal to the Max Limit, i.e., decision block 1618 is a "YES", the Erroneous BG filter 1600b proceeds to block 1622 and changes the StandardTag associated with the first BG measurement to "Invalid". Advantageously, decision block 1618 identifies imported BG values that are invalid as a result of meter malfunction or the patient 10 incorrectly inputting the associated BG measurement to the patient device 110. For instance, it is not possible for the patient 10 to have a BG measurement that is less than zero nor can the glucometer 124 output BG measurements that exceed the glucometer's 124 Max Limit. In some configurations, the Max Limit for the glucometer is 450 mg/dl. In other configurations, the Max Limit for the glucometer is less than or greater than 450 mg/dl. Moreover, any updated BG measurement that includes text is clearly filtered out as invalid. Accordingly, the Erroneous BG filter 1600*b* determines that a BG measurement is invalid when decision block 1618 is a "YES".

Upon one of the Erroneous BG filter 1600*b* leaving the StandardTag associated with the first BG measurement unchanged (block 1620) or changing the StandardTag to "Invalid" (block 1622), the Erroneous BG filter 1600*b* determines, at decision block 1624, if there is a Next BG measurement (e.g., a second BG measurement). If there is a Next BG measurement, i.e., decision block 1624 is "YES", then the Erroneous BG filter 1600*b* determines, at decision block 1618, if the Next BG measurement is valid or invalid as discussed above. After analyzing each BG measurement imported to the BG filter process 1500 as corresponding to one of a valid BG measurement or an invalid BG measurement, i.e., decision block 1624 is "NO", then the Erroneous BG filter 1600*b* ends at block 1626 and the BG filter process 1500 proceeds to the Standard Deviation Filter 1600*c* of FIG. 16C.

Referring to FIG. 16C, the Standard Deviation (StdDev) filter 1600*c* commences at block 1628 after completion of the Erroneous BG filter 1600*b* at block 1626 of FIG. 16B, and analyzes each BG measurement having a valid StandardTag to determine whether the StandardTag associated with the corresponding BG measurement should be left unchanged or changed to "Other". As used herein, each BG measurement having a "valid" StandardTag refers to the BG measurements having StandardTags that were not changed to "invalid" by block 1622 of the Erroneous BG filter 1600*b* of FIG. 16B. The StdDev filter 1600*c* calculates, at decision block 1630, a mean (BGmean) and standard deviation (StdDev) of all BG measurements not having StandardTags equal to "Invalid". Thereafter, for a first BG measurement having a valid StandardTag, the StdDev filter 1600*c* determines, at decision block 1632, whether the first BG measurement is greater than a value equal to a sum of the BGmean and 2*StdDev (BGmean+2*StdDev) calculated in block 1630. If the first BG measurement is not greater than BGmean+2*StdDev, i.e., decision block 1632 is a "NO", the StdDev filter 1600*c* proceeds to block 1634 and leaves the StandardTag associated with the first BG measurement unchanged.

On the other hand, if the first BG measurement is greater than BGmean+2*StdDev, i.e., decision block 1632 is a "YES", the StdDev filter 1600*c* proceeds to block 1636 and changes the StandardTag associated with the first BG measurement to "Other". Advantageously, decision block 1632 identifies imported BG values that are not invalid but are deemed not usable for the reasoning that they may correspond to abnormally high values that only occur intermittently or infrequently compared to the values of all the BG measurements contained in the imported BG data. For example, a BG measurement for the patient 10 that includes a value greater than BGmean+2*StdDev may occur after the patient 10 consumes a soft drink in which the patient 10 was under the belief contained zero carbohydrates, but in fact, contained a high number of carbohydrates. Under this scenario, the patient 10 may have not administered any insulin after consuming the soft drink, and as a result, the patient's 10 blood glucose elevated to a high value. Since such abnormally high BG values generally have no correlation to insulin dosing parameters, such as an insulin to carbohydrate ratio, the StdDev filter 1600*c* may filter them out so they are not used by the BG aggregation process 4400 (FIG. 17A). In fact, if such abnormally high BG values were used in determining adjustments to insulin dosing parameters, the patient 10 may be at risk of incurring hypoglycemic episodes after administering the insulin doses.

Upon one of the StdDev filter 1600*c* leaving the StandardTag associated with the first BG measurement unchanged (block 1634) or changing the StandardTag to "Other" (block 1636), the StdDev filter 1600*c* determines, at decision block 1638, if there is a Next BG measurement (e.g., a second BG measurement). If there is a Next BG measurement, i.e., decision block 1638 is "YES", then the StdDev filter 1600*c* determines, at decision block 1632, if the StandardTag of the Next BG measurement should be left unchanged or should be changed to "Other". When decision block 1638 is "NO", i.e., after analyzing each BG measurement deemed valid by the Erroneous BG filter 1600*b*, then the StdDev filter 1600*c* ends at block 1640 and the BG filter process 1500 proceeds to the Bolus-Time filter 1600*d* of FIG. 16D.

Figure 18A:
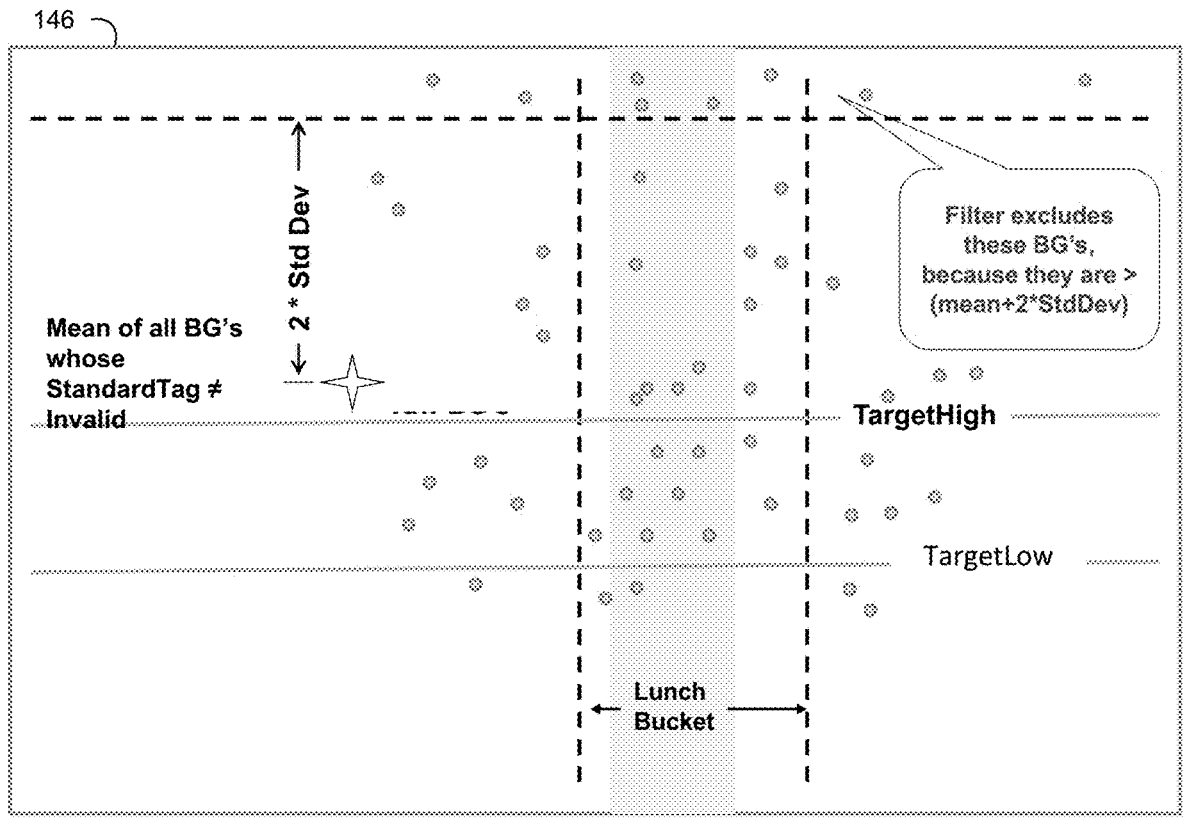
FIG. 18A is a schematic view of an exemplary standard deviation filter chart for viewing imported blood glucose measurements filtered by a standard deviation filter.

Referring to FIG. 18A, a schematic view of an exemplary Standard Deviation Filter Chart 503 for viewing imported BG measurements having a valid StandardTag that the StdDev filter 1600*c* leaves unchanged (block 1634 of FIG. 16C) or changes to "Other" (block 1636 of FIG. 16C). The standard Deviation Filter Chart 503 may display upon the display 146 when the StdDev filter 1600*c* is in use. FIG. 18A shows the dashed vertical lines defining the time interval associated with the Lunch Bucket and the blood glucose target range BGrR is defined by a lower limit, i.e., a low target $BG_{TRL}$, and an upper limit, i.e., a high target BCrRH, as similarly shown in the Modal Day Scatter Chart 502 (FIG. 12B). The Standard Deviation Filter Chart 503 includes a dashed horizontal line associated with the value equal to BGmean+2*StdDev as calculated by block 1630 of FIG. 16C. Here, the StdDev filter 1600*c* excludes each BG measurement that exceeds the threshold value equal to BGmean+2*StdDev (i.e., decision block 1632 is "YES") by changing the StandardTag to "Other" (block 1636).

Figure 16D:
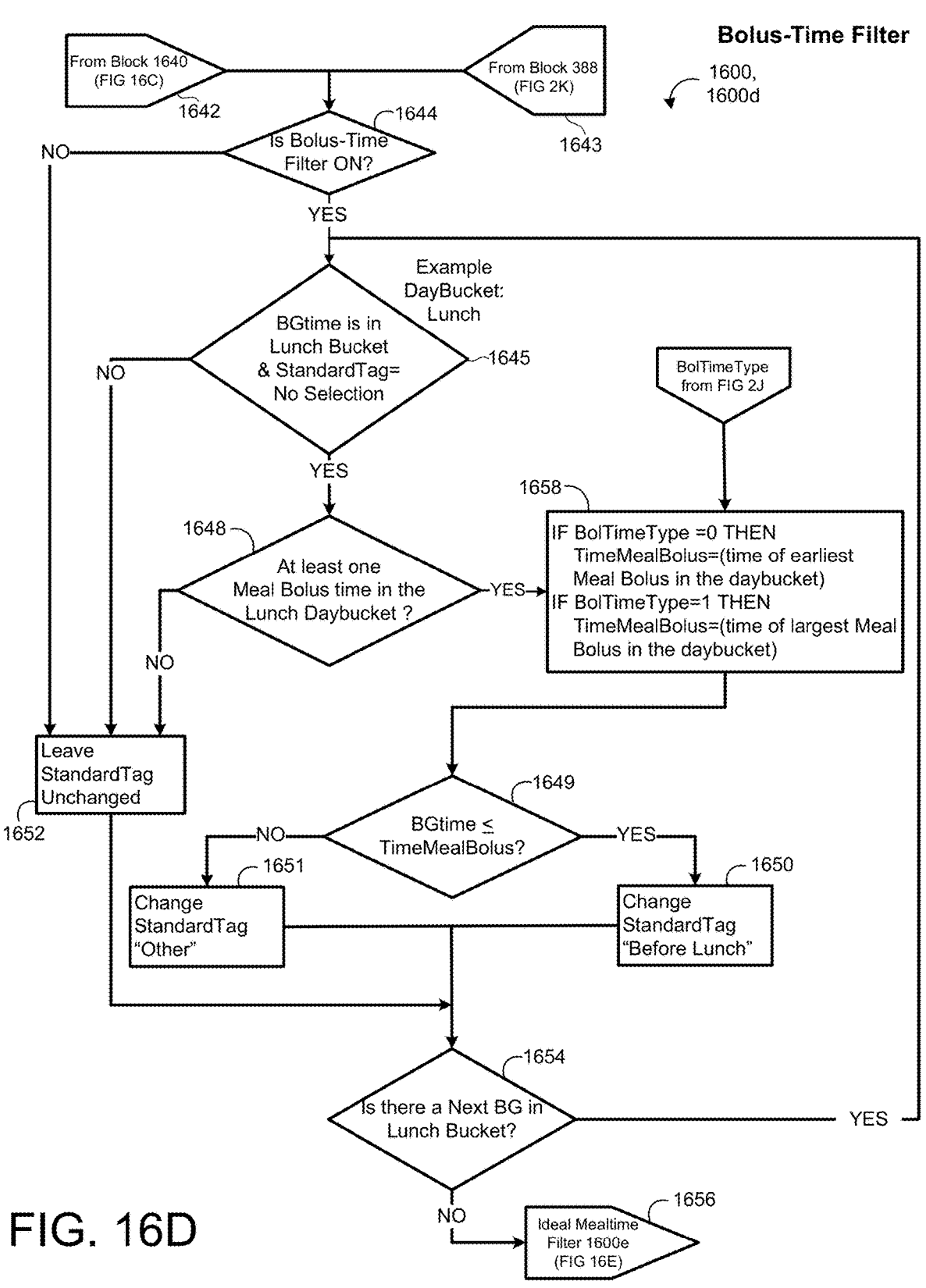

Referring to FIG. 16D, the Bolus-Time filter 1600*d* commences at block 1642 after completion of the StdDev filter 1600*c* at block 1640 of FIG. 16C, and analyzes each BG measurement having a StandardTag designated as "No Selection". In some examples, the Bolus-time filter 1600*d* only analyzes the BG measurements for the BG timebuckets (e.g., Breakfast, Lunch, and Dinner) associated with time intervals when the patient 10 is consuming meals. All StandardTags designated as "No Selection" correspond to BG measurements in which the patient 10 did not assign a tag, or optionally, the tag filter 1600*a* of FIG. 16A was turned OFF or changed the StandardTag previously assigned by the patient 10 to "No Selection" at block 1612 of FIG. 16A. While FIG. 16D shows the Bolus-Time filter 1600*d* filtering BG measurements having StandardTags designated as "No Selection" for the Lunch time-bucket, the Bolus-Time filter 1600*d* similarly filters BG measurements for the Breakfast and Dinner time-buckets. Additionally or alternatively, the Bolus-Time filter 1600*d* may analyze the BG measurements within time-buckets (e.g., Bedtime and/or Midsleep) when the patient 10 is not consuming meals. The Bolus-Time filter 1600*d* additionally receives, at block 1643, the value of the TimeMealBolus after completion of the TimeMealBolus selection process 300 at block 388 of FIG. 2K.

The Bolus-Time filter 1600*d* determines, at block 1644, whether or not the Bolus-Time filter is ON and available. When the Bolus-Time filter 1600*d* is OFF (e.g., unavailable), i.e., decision block 1644 is "NO", then the Bolus-Time filter 1600*d* proceeds to block 1652 and leaves the StandardTag unchanged, thereby allowing the BG measurement associated with the unchanged StandardTag tag to be screened by an enabled one of the Ideal Mealtime filter 1600e or the Whole Bucket filter 1600f at block 1656. The user 40 may switch the Bolus-Time filter 1600d between the ON and OFF states via the filter selector 370 of FIG. 2J. In some examples, enabling one of the Ideal Mealtime filter 1600e or the Whole Bucket filter 1600f in the ON state disables the other one of the Ideal filter 1600e or the Whole Bucket filter 1600f to the OFF state.

When the Bolus-Time filter 1600d is ON (e.g., available), i.e., decision block 1644 is "YES", then the Bolus-Time filter 1600d determines, at block 1645, whether a first BG measurement has a StandardTag of "No Selection" and if the BGtime is in the associated time-bucket (e.g., Lunch Bucket). If the first BG measurement does not include the StandardTag of "No Selection" and/or the first BG measurement is not in the associated time-bucket (e.g., Lunch Bucket), i.e., decision block 1645 is "NO", then the Bolus-Time filter 1600d proceeds to block 1652 and leaves the StandardTag unchanged. On the other hand, if first BG measurement includes the StandardTag of "No Selection" and the BGtime is in the associated time-bucket (e.g., Lunch Bucket), i.e., decision block 1645 is "Yes", then the Bolus-Time filter 1600d determines, at decision block 1648 if the associated DayBucket (e.g., Lunch Daybucket) has at least one lunch meal bolus value. If there is no value for the time of the meal bolus for the corresponding DayBucket (e.g., Lunch), i.e., decision block 1648 is "NO", then the Bolus-Time filter 1600d proceeds to block 1652 and leaves the StandardTag unchanged. Conversely, if there is a value for the time of the meal bolus for the corresponding DayBucket (e.g., Lunch), i.e., decision block 1648 is "YES", then the Bolus-Time filter 1600d proceeds to block 1658 to determine which bolus time among one or more possible bolus times to use as the TimeMealBolus. Block 1658 is provided with BolTimeType from the selector 376 in FIG. 2J. If BolTimeType is zero (0) then the earliest bolus time is chosen as the TimeMealBolus, but if BolTimeType is one (1) then the largest bolus in the DayBucket is chosen as the TimeMealBolus. This decision is passed to block 1649 to determine whether or not the time of the BG measurement (BGtime) is at or before the time value of the lunch meal bolus time (TimeMealBolus) in the Lunch DayBucket.

If the BGtime of the first BG measurement is after the TimeMealBolus for lunch, i.e., decision block 1649 is "NO", the Bolus-Time filter 1600d proceeds to block 1651 and changes the StandardTag to "Other". Changing the StandardTag to "Other" prevents the corresponding BG measurement from further opportunities of acquiring a usable Standard Tag and obtaining the Boolean parameter (Use) as Use=1. Thus, a StandardTag designated as "Other" prevents use of the corresponding BG measurement by the Aggregation Process 1700 of FIG. 17. On the other hand, if the BGtime of the first BG measurement is at or before the TimeMealBolus for lunch, i.e., decision block 1649 is "YES", the Bolus-Time filter 1600d proceeds to block 1650 and changes the StandardTag to "Before Lunch".

Upon the Bolus-Time filter 1600d leaving the StandardTag associated with the first BG measurement unchanged (block 1652) or changing the StandardTag associated with the first BG measurement from "No Selection" to "Before Lunch" (block 1650) or "Other" (block 1651), the Bolus-Time filter 1600d determines, at decision block 1654, if there is a Next BG measurement (e.g., a second BG measurement) designated as "No Selection" for the Lunch time-bucket. If there is a Next BG measurement, i.e., decision block 1654 is "YES", then the Bolus-Time filter 1600d reverts back to decision block 1648 for determining whether the second BG measurement designated as "NO Selection" has a value for lunch meal bolus time (TimeMealBolus). When decision block 1654 is "NO", i.e., after analyzing each BG measurement designated as "No Selection" for the Lunch time-bucket, then the Bolus-Time filter 1600d ends at block 1656 and the BG filter process 1500 proceeds to the Ideal Mealtime filter process 1600e. of FIG. 16E.

Figure 16E:
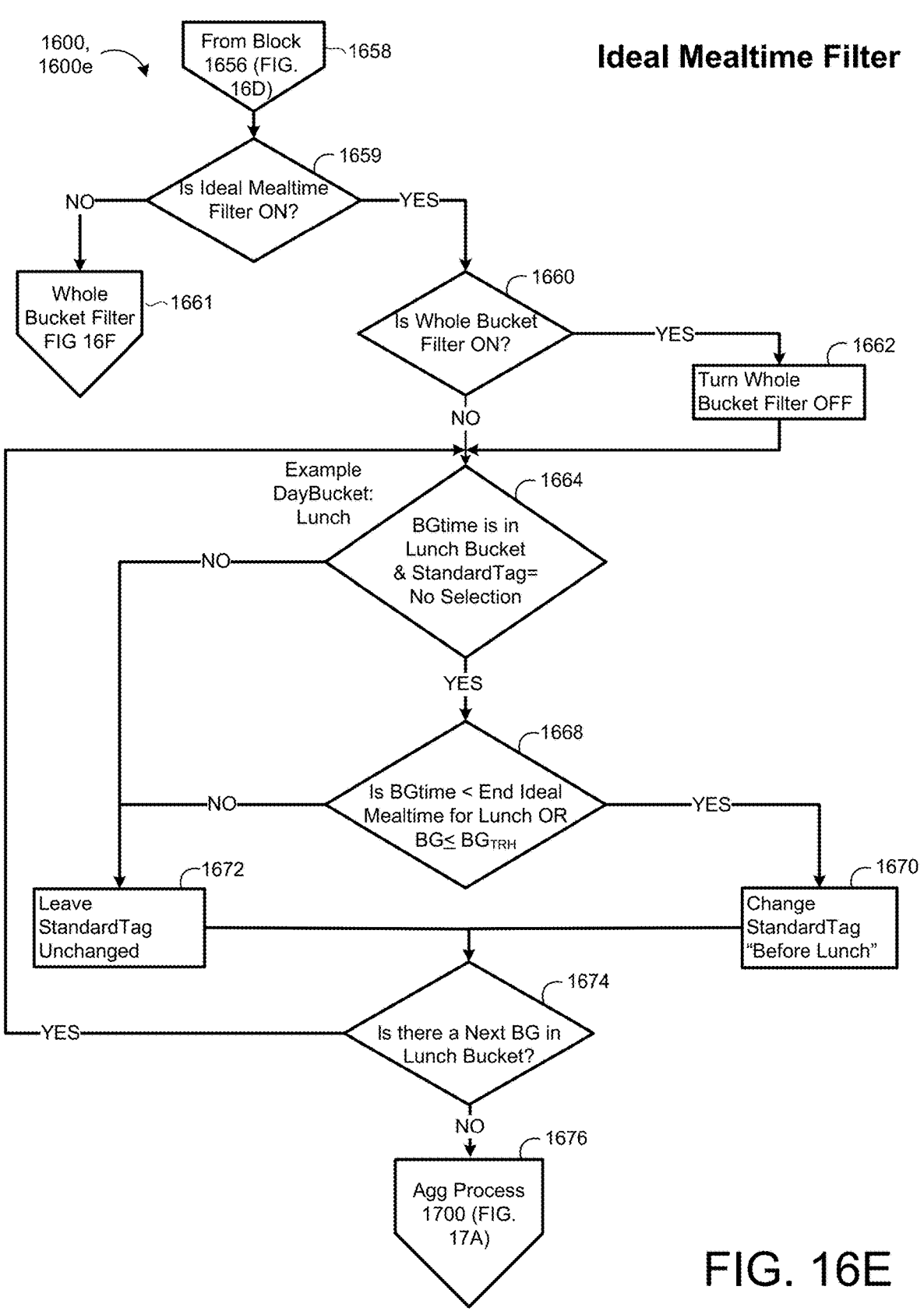

Referring to FIG. 16E, the Ideal Mealtime filter 1600e commences at block 1658 from block 1656 of FIG. 16D. In some implementations, only one of the Ideal Mealtime filter 1600e or the Whole Bucket filter 1600f is operative in the "ON" state at a time. Accordingly, only one of the filters 1600e, 1600f can be enabled in the ON state while the other one of the filters 1600e, 1600f is automatically disabled in the OFF state. As with the Bolus-Time filter 1600d of FIG. 16D, the Ideal Mealtime filter 1600e analyzes each BG measurement having a StandardTag designated as "No Selection" for the BG time-buckets (e.g., Breakfast, Lunch, and Dinner) associated time intervals when the patient 10 is consuming meals. Here, all StandardTags designated as "No Selection" correspond to BG measurements in which the patient 10 did not assign a tag, or optionally, the tag filter 1600a of FIG. 16A was turned OFF or changed the StandardTag previously assigned by the patient 10 to "No Selection" at block 1612 of FIG. 16A. While FIG. 16E shows the Ideal Mealtime filter 1600e filtering BG measurements having StandardTags designated as "No Selection" for the Lunch time-bucket, the Ideal Mealtime filter 1600e similarly aggregates BG measurements for the Breakfast and Dinner time-buckets. Additionally or alternatively, the Ideal Mealtime filter 1600e may analyze the BG measurements within time-buckets (e.g., Bedtime and/or Midsleep) when the patient 10 is not consuming meals.

The Ideal Mealtime filter 1600e determines, at decision block 1659, whether the Ideal Mealtime filter is enabled in the ON state. When the Ideal Mealtime filter is disabled in the OFF state, i.e., decision block 1659 is "NO", then the Ideal Mealtime filter 1600e ends at bock 1661 and the BG filter process 1500 proceeds to the Whole Bucket Filter 1600f of FIG. 16F. On the other hand, when the Ideal Mealtime filter is ON and available, i.e., decision block 1659 is "YES", then the Ideal Mealtimefilter 1600e proceeds to decision block 1660 to determine whether or not the Whole Bucket filter 1600f is ON and available. If the Whole Bucket 1600f is ON, i.e., decision block 1660 is "YES", then the Ideal Mealtime filter 1600e proceeds to block 1662 and instructs the filter process 1500 to turn off the Whole Bucket filter 1600f since the Ideal Mealtime filter 1600e is ON and available. Using the filter selector 370 of FIG. 2J, the Whole Bucket filter 1600f is automatically turned off at block 1662 when the Ideal Mealtime filter 1600e is enabled in the ON state.

Thereafter, the Ideal Mealtime filter 1600e determines, at block 1664, whether a first BG measurement has a StandardTag of "No Selection" and if the BGtime is in the associated time-bucket (e.g. Lunch). If the BGtime of the first BG measurement is in the Lunch time-bucket and the first BG measurement includes a StandardTag designated as "No Selection", i.e., decision block 1664 is "YES", the Ideal Mealtime filter 1600e proceeds to decision block 1668. On the other hand, if the first BG measurement does not include the StandardTag designated as "No Selection" or if the BGtime associated with the first BG measurement is not in the Lunch time-bucket, i.e., decision block 1664 is "NO", the Ideal Mealtime filter 1600e proceeds to block 1672 and leaves the StandardTag unchanged.

At decision block 1668, the Ideal Mealtime filter 1600e determines whether the first BG measurement has a time (BGtime) before the end of the Ideal Mealtime for Lunch and whether the first BG measurement is less than or equal to the upper limit of the BG target range, i.e., a high target $BG_{TRH}$. The shaded areas in the Modal Day Scatter Chart 502 (FIG. 12B) shows each Ideal Mealtime within each time-bucket and having boundaries adjustable using drag-and-drop methods by user inputs upon the Modal Day Scatter Chart (FIG. 12B) or via inputs to the Ideal Mealtime information 262 at the BG-time Buckets Input Screen (FIG. 2H). If at least one of the BGtime of the first BG measurement is before the end of the Ideal Mealtime for Lunch or the first BG measurement is less than or equal to the upper limit of the BG target range, $BG_{TRH}$, then the Ideal Mealtime filter 1600e proceeds to block 1670 and changes the StandardTag to "Before Lunch". On the other hand, if both the BGtime of the first BG measurement is at or after the end of the Ideal Mealtime for Lunch and the first BG measurement is greater than the upper limit of the BG target range, $BG_{TRH}$, then the Ideal Mealtime filter 1600e proceeds to block 1672 and leaves the StandardTag for the first BG measurement unchanged.

Upon the Ideal Mealtime filter 1600e leaving the StandardTag associated with the first BG measurement unchanged (block 1672) or changing the StandardTag from "No Selection" to "Before Lunch" (block 1670), the Ideal Mealtime filter 1600e determines, at decision block 1674, if there is a Next BG measurement (e.g., a second BG measurement) for the Lunch time-bucket, i.e., a BGtime within the time-bucket for lunch. If there is a Next BG measurement, i.e., decision block 1674 is "YES", then the Ideal Mealtime filter 1600e reverts back to decision block 1664 for determining whether the StandardTag associated with the second BG measurement is designated as "No Selection", and if so (e.g., decision block 1664 is "YES"), determines, at decision block 1668, whether the BGtime associated with the second BG measurement is before the end of the Ideal Mealtime for Lunch and whether the second BG measurement is less than or equal to the $BG_{TRH}$. When decision block 1674 is "NO", i.e., after analyzing each BG measurement designated as "NO Selection" for the Lunch time-bucket, then the Ideal Mealtime filter 1600e ends at block 1676 and the BG filter process 1500 proceeds to the Aggregation Process 1700 of FIG. 17A.

Figure 18B:
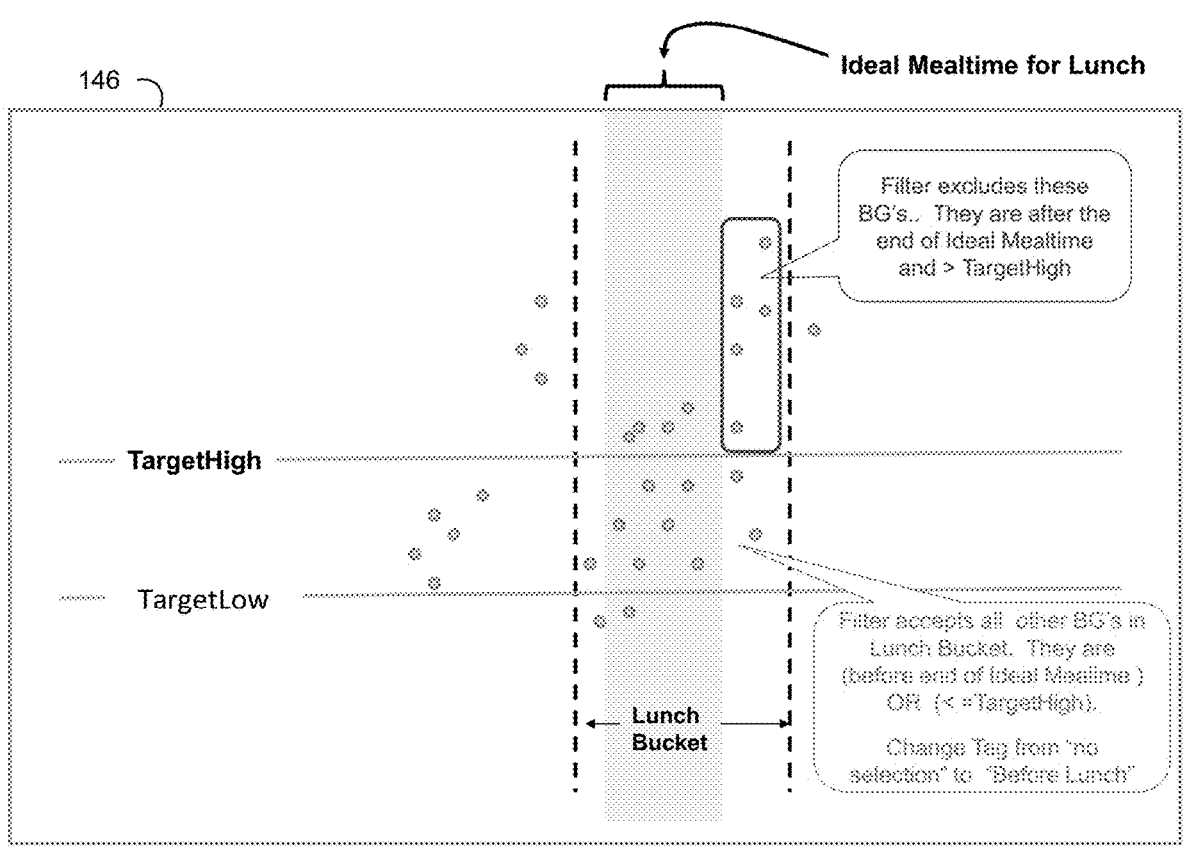
FIG. 18B is a schematic view of an example ideal mealtimes filter chart for viewing imported blood glucose measurements within an associated time-bucket that are greater than an upper limit of a blood glucose target range and have times occurring after an end of an ideal mealtime for the associated time-bucket.

Referring to FIG. 18B, a schematic view of an exemplary Ideal Mealtime Filter Chart 505 for viewing imported BG measurements each having StandardTags that the Ideal Mealtime filter 1600e leaves unchanged (block 1672 of FIG. 16E) or changes to "Before Lunch" (block 1670 of FIG. 16E). The Ideal Mealtime Filter Chart 505 may display imported BG measurements upon the display 146 when the Ideal Mealtime filter 1600e is in use. FIG. 18B shows the dashed vertical lines defining the time interval associated with the Lunch Bucket, the shaded area corresponding to the Ideal Mealtime within the Lunch Bucket, and the blood glucose target range $BG_{TR}$ is defined by a lower limit, i.e., a low target $BC_{TRL}$, and an upper limit, i.e., a high target $BC_{TRH}$, as similarly shown in the Modal Day Scatter Chart 502 (FIG. 12B). The Ideal Mealtime Filter Chart 505 shows the imported BG measurements within the Lunch Bucket that the Ideal Mealtime filter 1600e excludes, i.e., leaves the StandardTag unchanged (block 1672), due to the BG measurements associated with both values greater than $BG_{TRH}$ and BGtimes occurring after the end of the Ideal Mealtime for lunch.

Figure 16F:
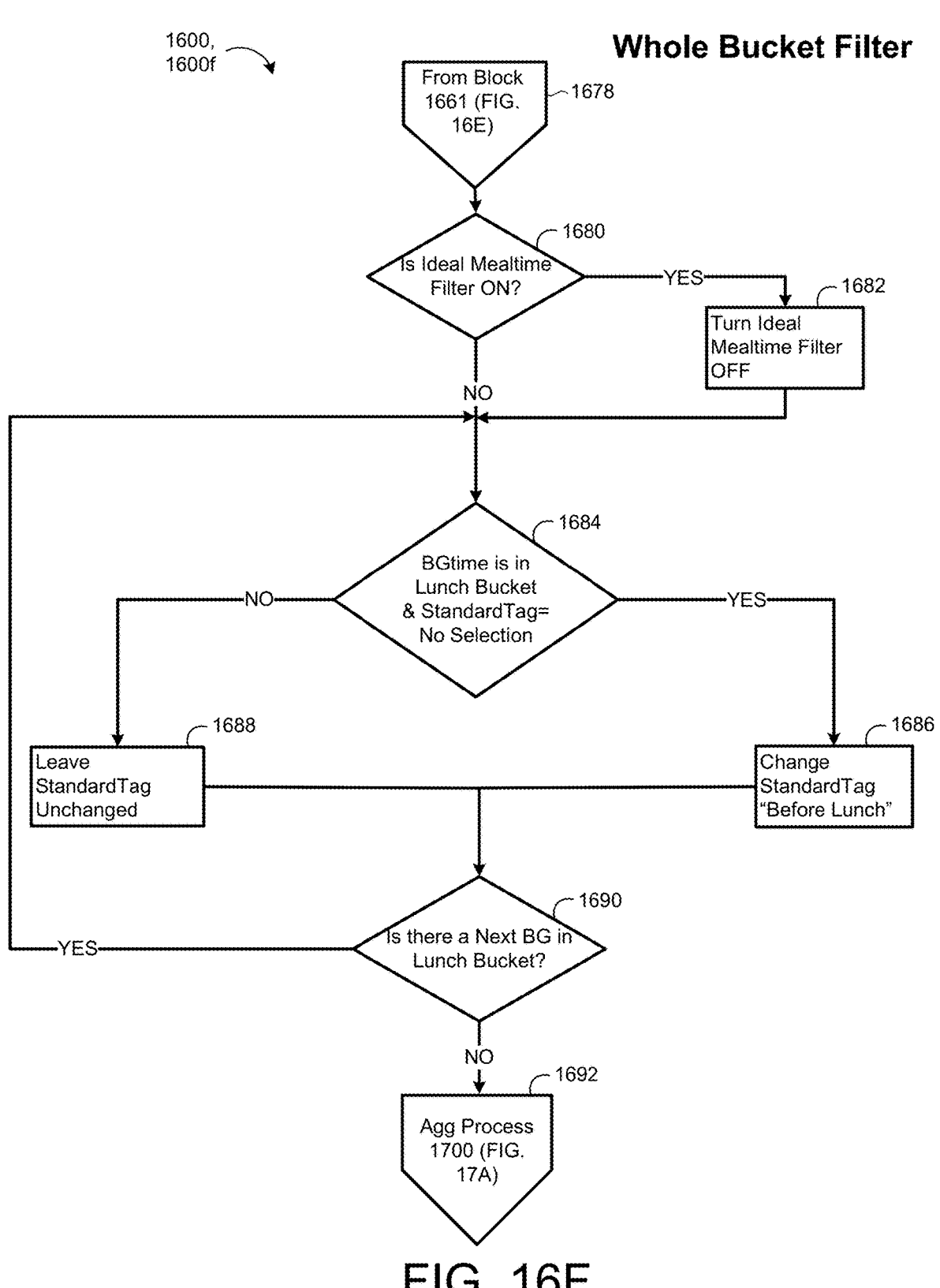

Referring to FIG. 16F, the Whole Bucket filter 1600f commences at block 1678 from block 1661 of the Ideal Mealtime filter 1600e when Ideal Mealtime filter 1600e is disabled in the OFF state. The BG filter process 1500 may alternatively proceed to the Whole Bucket filter 1600f from block 1656 of FIG. 16D of the Bolus-Time filter 1600d and then proceed to the Ideal Mealtime filter 1600e of FIG. 16E if a determination is made that the Whole Bucket filter 1600f is disabled in the OFF state. In some implementations, only one of the Ideal Mealtime filter 1600e or the Whole Bucket filter 1600f is operative in the "ON" state at a time. As with the Bolus-Time filter 1600d of FIG. 16D, the Whole Bucket filter 1600e analyzes each BG measurement having a StandardTag designated as "No Selection" for the BG time-buckets (e.g., Breakfast, Lunch, and Dinner) for time intervals when the patient 10 is consuming meals. Here, all StandardTags designated as "No Selection" correspond to BG measurements in which the patient 10 did not assign a tag, or optionally, the tag filter 1600a of FIG. 16A was turned OFF or changed the StandardTag previously assigned by the patient 10 to "No Selection" at block 1612 of FIG. 16A. While FIG. 16F shows the Whole Bucket filter 1600f filtering BG measurements having StandardTags designated as "No Selection" for the Lunch time-bucket, the Whole Bucket filter 1600f similarly aggregates BG measurements for the Breakfast and Dinner time-buckets. Additionally or alternatively, the Whole Bucket filter 1600f may analyze the BG measurements within time-buckets (e.g., Bedtime and/or Midsleep) when the patient 10 is not consuming meals.

The Whole Bucket filter 1600f determines, at block 1680, whether or not the Ideal Mealtime filter 1600e is ON and available. When the Ideal Mealtime filter 1600e is ON, i.e., decision block 1680 is "YES", then the Whole Bucket filter 1600f proceeds to block 1682 and instructs the filter process 1500 to turn off the Ideal Mealtime filter 1600e since the Whole Bucket filter 1600e is ON and available. Using the filter selector 370 of FIG. 2J, the Ideal Mealtime filter 1600f is automatically turned off at block 1682 when the Whole Bucket filter 1600f is enabled in the ON state and the Bolus-Time filter 1600d is disabled in the OFF state.

Thereafter, the Whole Bucket filter 1600f determines, at block 1684, whether a first BG measurement has a StandardTag of "No Selection" and if the BGtime of the first BG measurement is in the associated time-bucket (e.g., Lunch). If the BGtime of the first BG measurement is in the Lunch time-bucket and the first BG measurement includes a StandardTag designated as "No Selection", i.e., decision block 1684 is "YES", the Whole Bucket filter 1600f proceeds to block 1686 and changes the StandardTag to "Before Lunch". On the other hand, if the first BG measurement does not include the StandardTag designated as "No Selection" or if the BGtime associated with the first BG measurement is not in the Lunch time-bucket, i.e., decision block 1684 is "NO", the Whole Bucket filter 1600f proceeds to block 1688 and leaves the StandardTag unchanged.

Upon the Whole Bucket filter 1600f leaving the StandardTag associated with the first BG measurement unchanged (block 1688) or changing the StandardTag from "No Selection" to "Before Lunch" (block 1686), the Whole Bucket filter 1600f determines, at decision block 1690, if there is a Next BG measurement (e.g., a second BG measurement) for the Lunch time-bucket, i.e., a BGtime within the time-bucket for lunch. If there is a Next BG measurement, i.e., decision block 1690 is "YES", then the Whole Bucket filter 1600f reverts back to decision block 1684 for determining whether the StandardTag associated with the second BG measurement is designated as "No Selection". When decision block 1690 is "NO", i.e., after analyzing each BG measurement designated as "NO Selection" for the Lunch time-bucket, then the Whole Bucket filter 1600ƒ ends at block 1692 and the BG filter process 1500 proceeds to the Aggregation Process 1700 of FIG. 17A.

Referring to FIG. 17A, after the filtering process 1500 completes the filtering of the imported BG data, the aggregation process 1700 commences at block 1702, and applies, at block 1704, a DayBucket Aggregation method to determine an aggregate value for each DayBucket within an associated time-bucket under consideration. The user 40 (e.g., HCP) may select the DayBucket Aggregation method via the DayBucket Aggregation Method selector 372 of FIG. 2J. For in instance, the DayBucket aggregate value for each DayBucket may include, but is not limited to, one of the Minimum of filtered BG measurements in the DayBucket, the Earliest of filtered BG measurements in a DayBucket, the Mean of filtered BG measurements in the DayBucket, or the Median of filtered BG measurements in the DayBucket. FIG. 17A shows the DayBucket Aggregate Method of block 1704 determining, for each DayBucket within the Lunch Bucket, the minimum of all BG measurements with Usable StandardTags and Use=1. Block 1704 may output a value of "null" when the available data is insufficient for determining the DayBucket aggregate value.

Once the DayBucket aggregate value (e.g., MIN (All BG measurements in DayBucket with Usable StandardTags and Use=1)) is determined for each DayBucket within the Lunch Bucket, the aggregation process 1700 proceeds to block 1706 and calculates a NdayBucketsMin by multiplying the configurable constant Kndays (FIG. 2I) by a NdayBuckets. The NdayBuckets corresponds to a value that counts the number of DayBuckets within the associated time-bucket (e.g., Lunch BG time-bucket) from the current date/time backward to an earliest permissible date/time DataStartDateTime. As used herein, the "earliest date" refers to the earliest one of a previous dosing adjustment or the MaxDays (FIG. 2I) into the past or to a custom date range. Accordingly, when the Fewest & Lowest Aggregation is used, the NdayBuckets value may be calculated for each of the time-buckets and may be designated as corresponding ones of NdaysBreakfast, NdaysLunch, NdaysDinner, NdaysBedtime, and NdaysMidSleep. The user 40, via the BG Update Interval input screen (FIG. 2I), may set Kndays to a positive value less than one. In some examples, when Kndays is equal to 0.5, the NdayBucketsMin value is half of the NdaysBucket value for the associated time-bucket. Accordingly, the value for NdaysBucketMin is associated with a number of "available" DayBuckets for the associated time-bucket since the DataStartDateTime. Block 1706 may iteratively output values of NdayBucketsMin for each of the Usable time-buckets (e.g., Midsleep, Breakfast, Lunch, Dinner, and Bedtime) where each value over-writes the previous. In some implementations, a separate variable is used for each bucket and is named appropriately, e.g NdayBucketsMinLunch.

After determining the minimum of all BG measurements with Usable StandardTags and Use=1 for each DayBucket within the associated time-bucket (block 1704) and calculating the value of NdayBucketsMin (block 1706), the aggregation process 1700 applies a Bucket aggregation method to the associated time-bucket (e.g., Lunch). The user 40 (e.g., HCP) may use the Bucket Aggregation Method selector 374 of FIG. 2J to select the Bucket aggregation method from the one of the Mean of DayBucket Aggregates for the associated time-bucket, the Median of DayBucket Aggregates for the associated time-bucket, or the Automatic Mean or Median of DayBucket Aggregates for the associated time-bucket. Additionally, the user 40 may use the Bucket Aggregation Method selector 374 to select whether the selected bucket aggregation method will use the Fewest & Lowest number of DayBucket aggregates for the associated time-bucket. Accordingly, at decision block 1708, the aggregation process 1700 determines whether the selected bucket aggregation method uses the Fewest & Lowest Aggregation.

When the aggregation process 1700 determines the selected bucket aggregation method uses the Fewest & Lowest Aggregation, i.e., decision block 1708 is "YES", the aggregation process 1700 proceeds to block 1710 and determines the bucket aggregate value for the associated time-bucket (e.g., BGlunch) using the lowest DayBucket Aggregate values (block 1704) up until NdayBucketsMin (block 1706). For instance, if the value of NdayBucketsMin is equal to 14, then the aggregation process 1700 will use the lowest 14 DayBucket Aggregate values for determining the bucket aggregate value for the associated time-bucket. Here, if the number of DayBucket Aggregate values is equal to 18, and therefore greater than the NdayBucketsMin value of 14, then the aggregation process 1700 will not use the four (4) highest DayBucket Aggregate values when determining the bucket aggregate value at block 1710 for the associated time-bucket. In scenarios when there are fewer DayBucket Aggregate values than NdayBucketsMin for the associated time-bucket, then all of the DayBucket Aggregate values determined by the aggregation process 1700 at block 1704 will be used for determining the aggregate value. These scenarios will be screened from use by the Sufficient Data Checker FIG. 17B. Thereafter, the aggregation process 1700 proceeds to block 1716 of FIG. 17B and executes a sufficient data checker sub-routine 1701 for the associated time-bucket (e.g., Lunch). Additionally, the aggregation process 1700 provides the bucket aggregate value (e.g., BGlunch) to block 1714 for plotting upon the Modal Day Scatter Chart 502 of FIG. 12B.

Conversely, when the aggregation process 1700 determines the selected aggregation method will not use the Fewest & Lowest Aggregation, i.e., decision block 1708 is "NO", the aggregation process 1700 proceeds to block 1712 and determines the bucket aggregate value (e.g., BGlunch) for the associated time-bucket using all of the DayBucket Aggregate values (block 1704). Thereafter, the aggregation process 1700 proceeds to block 1716 of FIG. 17B and executes the sufficient data checker sub-routine 1701 for the associated time-bucket (e.g., Lunch). Additionally, the aggregation process 1700 provides the bucket aggregate value (e.g., BGlunch) to block 1714 for plotting upon the Modal Day Scatter Chart 502 of FIG. 12B.

After the bucket aggregate value (e.g., BGlunch value) for the associated time-bucket is determined by the aggregation process 1700 at one of blocks 1710 or 1712, the aggregation process 1700 reverts back to block 1704 for determining the bucket aggregate value for a next time-bucket (e.g., BGDinner) until bucket aggregate values are determined for each of the time-buckets (BGbreakfast, BGlunch, BGdinner, BGbedtime, and BGmidsleep values).

At block 1714, the aggregation process 1700 plots the bucket aggregate values for BGbreakfast, BGlunch, BGdinner, BGbedtime, and BGmidsleep and all valid BG measurements of the imported BG data in the Modal Day Scatter Chart 502 (FIG. 12B). However, the BG measurements having StandardTags designated by the Erroneous BG filter 1600b (FIG. 16B) as "Invalid", are rejected and not plotted in the Modal Day Scatter Chart 502. The Modal Day Scatter Chart 502 may use color-coordinate BG measurements to differentiate usable BG measurements from unusable BG measurements. Color coordinating may also be used to differentiate BG measurements that are hypoglycemic (e.g., exceeding BG$_{TRL}$), BG measurements within the BG target range, and/or BG measurements that are hyperglycemic (e.g., exceeding BG$_{TRH}$).

Figure 17B:
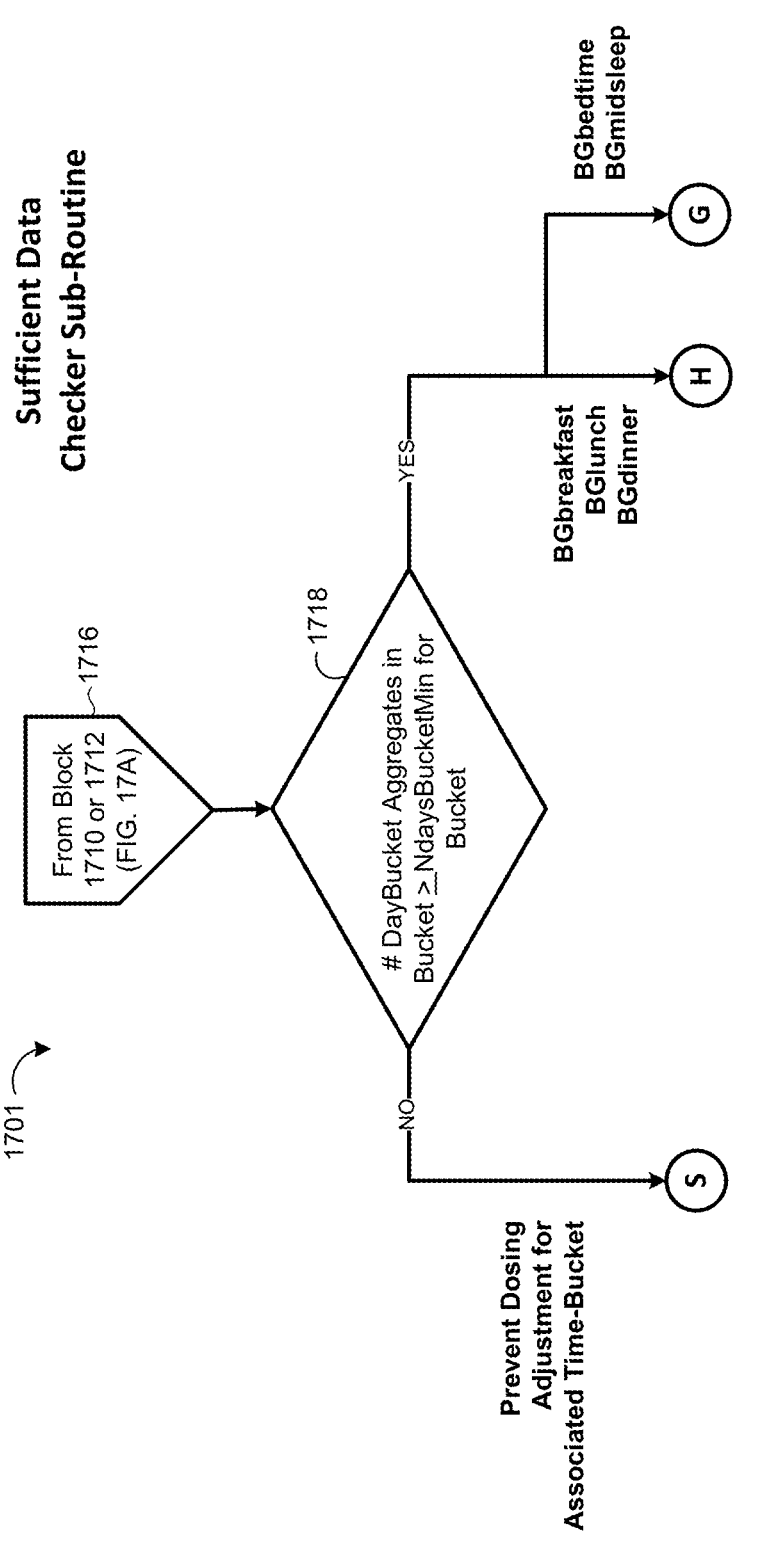
FIG. 17B is a schematic view of an example sufficient data checker sub-routine executed by the aggregation process of FIG. 17A.

Referring to FIG. 17B, the sufficient data checker sub-routine 1701 determines whether or not there is a sufficient amount of BG data associated with each corresponding bucket aggregate value output by the aggregation process 1700 at one of blocks 1710 or 1712. The sub-routine 1701 commences at block 1716 and determines, at block 1718, whether the number of DayBucket Aggregate values (# of DayBucket Aggregates) (e.g., BGlunch) is greater than or equal to the NdayBucketsMin for the associated time-bucket). When the number of DayBucket Aggregate values (block 1704 of FIG. 17A) is greater than or equal to NdayBucketsMin (block 1706 of FIG. 17A), i.e., decision block 1718 is "YES", the corresponding bucket aggregate value for the associated time-bucket is provided to a designated one of Entry Point G or Entry Point H for use by processes 2300, 2400, 2500 of FIGS. 8, 9, and 10, respectively. In other words, the BG data associated with the corresponding bucket aggregate value is sufficient for use in adjusting insulin doses governed by the associated time-bucket. Accordingly, bucket aggregate values for BGbed-time and BGmidsleep are provided to Entry Point G while bucket aggregate values for BGbreakfast, BGlunch, and BGdinner are provided to Entry Point H.

On the other hand, when the number of DayBucket Aggregate values is less than NdayBucketsMin, i.e., decision block 1718 is "YES", the corresponding bucket aggregate value for the associated time-bucket is provided to Entry Point S for use by processes 2300, 2400, 2500 of FIGS. 8, 9, and 10, respectively. Thus, the BG data associated with the corresponding bucket aggregate value is insufficient and the processes 2300, 2400, 2500 will prevent adjustment of doses governed by the associated time-bucket. For instance, from Entry Point S, the processes 2300, 2400, 2500 will apply an Adjustment Factor (AF) equal to "1" so that a previous dose governed by associated time-bucket is used.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation.

Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A computer-implemented method executed on data processing hardware that causes the data processing hardware to perform operations comprising:

identifying a scheduled glucose measurement time interval within a day for a patient having a diagnosis of diabetes, wherein the scheduled glucose measurement time interval comprises a meal insulin bolus administration time, wherein the scheduled glucose measurement time interval is one of a plurality of non-overlapping scheduled glucose measurement time intervals within the day for the patient;

obtaining glucose data of the patient from a continuous glucose monitoring system in communication with the data processing hardware, the glucose data including a plurality of glucose measurements of the patient and a plurality of glucose measurement times, wherein each glucose measurement of the plurality of glucose measurements is associated with a respective glucose measurement time of the plurality of glucose measurement times;

identifying which of the plurality of glucose measurements have a respective glucose measurement time falling within the scheduled glucose measurement time interval and are usable, wherein determining that a glucose measurement is usable comprises identifying that the glucose measurement time associated with the glucose measurement is at or before the meal insulin bolus administration time associated with the scheduled glucose measurement time interval;

processing the glucose measurements identified as having the respective glucose time falling within the scheduled glucose measurement time interval and as usable to determine a representative glucose measurement for the scheduled glucose measurement time interval by:

determining a sum of the glucose measurements identified as having the respective glucose time falling within the scheduled glucose measurement time interval and as usable; and determining a mean value for the scheduled glucose measurement time interval by dividing the sum by a total number of the glucose measurements identified as having the respective glucose time falling within the scheduled glucose measurement time interval and as usable, wherein the mean value comprises the representative glucose measurement for the scheduled glucose measurement time interval;

determining a next recommended insulin dosage for a correction dose of insulin for the patient's diagnosis of diabetes based on the representative glucose measurement;

transmitting the next recommended insulin dosage for the correction dose of insulin from the data processing hardware to a portable device associated with the patient, the portable device configured to display the next recommended insulin dosage; and administering the correction dose of insulin to the patient to treat the patient's diagnosis of diabetes by transmitting instructions comprising the next recommended insulin dosage for the correction dose of insulin to an administration device in communication with the data processing hardware, the administration device comprising:

a doser; and an administration computing device in communication with the doser, the administration computing device configured to, in response to the instructions, cause the doser to administer the correction dose of insulin to the patient.

2. The method of claim 1, wherein obtaining the glucose data comprises one or more of:

receiving the glucose data from a remote computing device in communication with the data processing hardware during a batch download process, the remote computing device executing a download program for downloading the glucose data from the continuous glucose monitoring system;

receiving the glucose data from the continuous glucose monitoring system; or receiving the glucose data from a patient device in communication with the data processing hardware and the continuous glucose monitoring system, the patient device receiving the glucose data from the continuous glucose monitoring system.

3. The method of claim 1, wherein the operations further comprise:

identifying a glucose measurement as invalid and unusable when the glucose measurement corresponds to one of a numerical value less than or equal to zero, a numerical value greater than or equal to a maximum limit associated with the continuous glucose monitoring system, or text; and identifying a glucose measurement as valid when the glucose measurement corresponds to a positive integer less than the maximum limit associated with the continuous glucose monitoring system;

determining the glucose measurement exceeds a threshold value based on a mean of the glucose measurements and a standard deviation of the glucose measurements; and based on determining the glucose measurement exceeds the threshold value based on the mean of the glucose measurements and the standard deviation of the glucose measurements, identifying the glucose measurement identified as valid as unusable.

4. The method of claim 3, wherein identifying that the glucose measurement is usable further comprises at least one of:

identifying the glucose measurement as usable when the respective glucose measurement time is at or before an end of an ideal mealtime associated with the scheduled glucose measurement time interval, or the glucose measurement is less than or equal to an upper limit of a target glucose range for the patient; or identifying the glucose measurement as usable when the respective glucose measurement time is within the scheduled glucose measurement time interval.

5. The method of claim 1, wherein the operations further comprise:

receiving a specified date range from a remote healthcare provider computing device in communication with the data processing hardware;

aggregating one or more of the glucose measurements associated with the specified date range to determine a daily aggregate glucose measurement for each day within the specified date range; and aggregating the one or more of the daily aggregate glucose measurement associated with the specified date range to determine a representative aggregate glucose measurement associated with the specified date range.

6. The method of claim 5, wherein the operations further comprise:

calculating a minimum number of available daily aggregate values by multiplying the total number of days within the specified date range by a configurable set point equal to a value between zero and one; and aggregating the daily aggregate glucose measurement associated with the lowest values up until the minimum number of available daily aggregate values to determine the representative aggregate glucose measurement associated with the specified date range.

7. The method of claim 6, wherein the operations further comprise:

determining the total number of daily aggregate values associated with the specified date range is greater than or equal to the minimum number of available daily aggregate values; and preventing adjustments to a previous recommended insulin dosage governed by the specified date range based on determining the total number of daily aggregate values associated with the specified date range is less than the minimum number of available daily aggregate values.

8. The method of claim 7, wherein the operations further comprise, based on determining the total number of daily aggregate values associated with the specified date range is greater than or equal to the minimum number of available daily aggregate values, adjusting the previous recommended insulin dosage governed by the specified date range based on the representative aggregate glucose measurement associated with the specified date range.

9. The method of claim 5, wherein the operations further comprise:

selecting a governing glucose measurement as the representative aggregate glucose measurement associated with the specified date range;

determining an adjustment factor for adjusting a next recommended meal bolus governed by the specified date range based on the selected governing glucose measurement;

obtaining a previous day recommended meal bolus governed by the specified date range; and determining the next recommended meal bolus by multiplying the adjustment factor times the previous day recommended meal bolus, wherein the specified date range includes one of a lunch glucose time interval, a dinner glucose time interval, or a bedtime glucose time interval.

10. The method of claim 1, wherein each scheduled glucose measurement time interval correlates to an associated glucose type including one of a pre-breakfast glucose measurement, a pre-lunch glucose measurement, a pre-dinner glucose measurement, a bedtime glucose measurement and a midsleep glucose measurement.

11. A dosing controller comprising:

data processing hardware; and memory hardware in communication with the data processing hardware, the memory hardware storing instructions for a subcutaneous outpatient program that, when executed on the data processing hardware, cause the data processing hardware to perform operations comprising:

identifying a scheduled glucose measurement time interval within a day for a patient having a diagnosis of diabetes, wherein the scheduled glucose measurement time interval comprises a meal insulin bolus administration time, wherein the scheduled glucose measurement time interval is one of a plurality of non-overlapping scheduled glucose measurement time intervals within the day for the patient;

obtaining glucose data of the patient from a continuous glucose monitoring system in communication with the data processing hardware, the glucose data including a plurality of glucose measurements of the patient and a plurality of glucose measurement times, wherein each glucose measurement of the plurality of glucose measurements is associated with a respective glucose measurement time of the plurality of glucose measurement times;

identifying which of the plurality of glucose measurements have a respective glucose measurement time falling within the scheduled glucose measurement time interval and are usable, wherein determining that a glucose measurement is usable comprises identifying that the glucose measurement is usable when the glucose measurement time associated with the glucose measurement is at or before the meal insulin bolus administration time associated with the scheduled glucose measurement time interval;

processing the glucose measurements identified as having the respective glucose time falling within the scheduled glucose measurement time interval and as usable to determine a representative glucose measurement for the scheduled glucose measurement time interval by:

determining a sum of the glucose measurements identified as having the respective glucose time falling within the scheduled glucose measurement time interval and as usable; and determining a mean value for the scheduled glucose measurement time interval by dividing the sum by a total number of the glucose measurements identified as having the respective glucose time falling within the scheduled glucose measurement time interval and as usable, wherein the mean value comprises the representative glucose measurement for the scheduled glucose measurement time interval;

determining a next recommended insulin dosage for a correction dose of insulin for the patient's diagnosis of diabetes based on the representative glucose measurement;

transmitting the next recommended insulin dosage for the correction dose of insulin from the data processing hardware to a portable device associated with the patient, the portable device configured to display the next recommended insulin dosage; and administering the correction dose of insulin to the patient to treat the patient's diagnosis of diabetes by transmitting instructions comprising the next recommended insulin dosage for the correction dose of insulin to an administration device in communication with the data processing hardware, the administration device comprising:

a doser; and an administration computing device in communication with the doser, the administration computing device configured to, in response to the instructions, cause the doser to administer the correction dose of insulin to the patient.

12. The dosing controller of claim 11, wherein obtaining the glucose data comprises one or more of:

receiving the glucose data from a remote computing device in communication with the dosing controller during a batch download process, the remote computing device executing a download program for downloading the glucose data from the continuous glucose monitoring system;

receiving the glucose data from the continuous glucose monitoring system; or receiving the glucose data from a patient device in communication with the dosing controller and the continuous glucose monitoring system, the patient device receiving the glucose data from the continuous glucose monitoring system.

13. The dosing controller of claim 11, wherein the operations further comprise:

identifying a glucose measurement as invalid and unusable when the glucose measurement corresponds to one of a numerical value less than or equal to zero, a numerical value greater than or equal to a maximum limit associated with the continuous glucose monitoring system, or text; and identifying a glucose measurement as valid when the glucose measurement corresponds to a positive integer less than the maximum limit associated with the continuous glucose monitoring system;

determining the glucose measurement exceeds a threshold value based on a mean of the glucose measurements and a standard deviation of the glucose measurements; and based on determining the glucose measurement exceeds the threshold value based on the mean of the glucose measurements and the standard deviation of the glucose measurements, identifying the glucose measurement identified as valid as unusable.

14. The dosing controller of claim 13, identifying that the glucose measurement is usable further comprises at least one of:

identifying the glucose measurement as usable when the respective glucose measurement time is at or before an end of an ideal mealtime associated with the scheduled glucose measurement time interval, or the glucose measurement is less than or equal to an upper limit of a target glucose range for the patient; or identifying the glucose measurement as usable when the respective glucose measurement time is within the scheduled glucose measurement time interval.

15. The dosing controller of claim 11, wherein the operations further comprise:

receiving a specified date range from a remote healthcare provider computing device in communication with the data processing hardware;

aggregating one or more of the glucose measurements associated with the specified date range to determine a daily aggregate glucose measurement for each day within the specified date range; and aggregating one or more of the daily aggregate glucose measurement associated with the specified date range to determine a representative aggregate glucose measurement associated with the specified date range.

16. The dosing controller of claim 15, wherein the operations further comprise:

calculating a minimum number of available daily aggregate values by multiplying the total number of days within the specified date range by a configurable set point equal to a value between zero and one; and aggregating the daily aggregate glucose measurement associated with the lowest values up until the minimum number of available daily aggregate values to determine the representative aggregate glucose measurement associated with the specified date range.

17. The dosing controller of claim 16, wherein the operations further comprise:

determining the total number of daily aggregate values associated with the specified date range is greater than or equal to the minimum number of available daily aggregate values; and preventing adjustments to a previous recommended insulin dosage governed by the specified date range based on determining the total number of daily aggregate values associated with the specified date range is less than the minimum number of available daily aggregate values.

18. The dosing controller of claim 17, wherein the operations further comprise, based on determining the total number of daily aggregate values associated with the specified date range is greater than or equal to the minimum number of available daily aggregate values, adjusting the previous recommended insulin dosage governed by the specified date range based on the representative aggregate glucose measurement associated with the specified date range.

19. The dosing controller of claim 15, wherein the operations further comprise:

selecting a governing glucose measurement as the representative aggregate glucose measurement associated with the specified date range;

determining an adjustment factor for adjusting a next recommended meal bolus governed by the specified date range based on the selected governing glucose measurement;

obtaining a previous day recommended meal bolus governed by the specified date range; and determining the next recommended meal bolus by multiplying the adjustment factor times the previous day recommended meal bolus, wherein the specified date range includes one of a lunch glucose time interval, a dinner glucose time interval, or a bedtime glucose time interval.

20. The dosing controller of claim 11, wherein each scheduled glucose measurement time interval correlates to an associated glucose type including one of a pre-breakfast glucose measurement, a pre-lunch glucose measurement, a pre-dinner glucose measurement, a bedtime glucose measurement and a midsleep glucose measurement.

* * * * *